US005770678A

United States Patent [19]
Drysdale et al.

[11] Patent Number: 5,770,678
[45] Date of Patent: Jun. 23, 1998

[54] POLYMERIZATION OF, AND DEPOLYMERIZATION TO, CYCLIC ETHERS USING SELECTED METAL COMPOUND CATALYSTS

[75] Inventors: Neville Everton Drysdale, Newark; Richard Edmund Bockrath, Wilmington; Norman Herron, Newark; Joel David Citron, Wilmington, all of Del.

[73] Assignee: E. I. du Pont de Nemours and Company, Wilmington, Del.

[21] Appl. No.: 762,813

[22] Filed: Dec. 9, 1996

Related U.S. Application Data

[60] Continuation of Ser. No. 424,675, Apr. 19, 1995, Pat. No. 5,635,585, which is a division of Ser. No. 283,108, Jul. 29, 1994, abandoned, which is a continuation-in-part of Ser. No. 198,024, Feb. 17, 1994, abandoned, Ser. No. 141,160, filed as PCT/US93/09808, Oct. 20, 1993, abandoned, Ser. No. 93,243, Jul. 16, 1993, abandoned, Ser. No. 93,119, Jul. 16, 1993, abandoned, Ser. No. 21,368, Feb. 23, 1996, abandoned, and Ser. No. 964,313, Oct. 21, 1992, abandoned.

[51] Int. Cl.⁶ ............................ C08G 4/00; C08G 65/20; C08G 65/26; C08G 65/16
[52] U.S. Cl. ......................... 528/233; 528/234; 528/235; 528/236; 528/237; 528/238; 528/409; 528/410; 528/411; 528/412; 528/413; 528/414; 528/416; 528/365
[58] Field of Search .................................. 528/409, 410, 528/411, 412, 413, 414, 416, 233–238, 365

[56] References Cited

U.S. PATENT DOCUMENTS

| | | | |
|---|---|---|---|
| 2,394,910 | 2/1946 | Gresham | 568/613 |
| 2,811,512 | 10/1957 | Austin et al. | 260/78.4 |
| 3,344,088 | 9/1967 | Miller | 260/2 |
| 3,464,958 | 9/1969 | Matsuura et al. | 260/78.4 |
| 3,842,019 | 10/1974 | Kropp | 528/410 |
| 3,864,287 | 2/1975 | Matsuda et al. | 568/617 |
| 3,907,706 | 9/1975 | Robins | 252/431 |
| 4,115,408 | 9/1978 | Baker | 260/346.11 |
| 4,153,786 | 5/1979 | Pruckmayr | 528/408 |
| 4,303,782 | 12/1981 | McHale et al. | 528/416 |
| 4,324,873 | 4/1982 | Wada et al. | 528/410 |
| 4,363,924 | 12/1982 | Mueller et al. | 549/509 |
| 4,585,592 | 4/1986 | Mueller | 260/408 |
| 4,599,401 | 7/1986 | Koleske | 528/410 |
| 4,721,599 | 1/1988 | Olah | 208/135 |
| 4,728,722 | 3/1988 | Mueller | 568/617 |
| 4,988,797 | 1/1991 | Wardle et al. | 526/617 |
| 5,028,667 | 7/1991 | McLain et al. | 525/415 |
| 5,084,586 | 1/1992 | Farooq | 556/181 |
| 5,102,849 | 4/1992 | Kemp | 502/214 |
| 5,124,417 | 6/1992 | Farooq | 528/410 |
| 5,130,470 | 7/1992 | Dorai et al. | 560/200 |
| 5,202,413 | 4/1993 | Spinu | 525/415 |
| 5,208,297 | 5/1993 | Ford et al. | 525/415 |
| 5,208,385 | 5/1993 | Kahn et al. | 586/617 |
| 5,210,283 | 5/1993 | Kahn et al. | 568/617 |
| 5,225,521 | 7/1993 | Spinu | 525/415 |
| 5,235,031 | 8/1993 | Drysdale et al. | 525/415 |
| 5,250,188 | 10/1993 | Bruening et al. | 210/672 |
| 5,430,122 | 7/1995 | Drysdale | 528/55 |
| 5,475,069 | 12/1995 | Drysdale | 526/192 |
| 5,478,920 | 12/1995 | Drysdale | 528/410 |
| 5,541,346 | 7/1996 | Drysdale et al. | 549/509 |

FOREIGN PATENT DOCUMENTS

| | | | |
|---|---|---|---|
| 0 037 341 | 10/1981 | European Pat. Off. | C08F 4/06 |
| 0 105 080 | 4/1984 | European Pat. Off. | |
| 0 485 637 | 5/1992 | European Pat. Off. | |
| 2212364 | 7/1974 | France | |
| 2235950 | 1/1975 | France | C08F 4/44 |
| 886 304 | 7/1953 | Germany | C08G 63/42 |
| 2 459 163 | 12/1974 | Germany | C08G 65/20 |
| A 3 606 479 | 9/1987 | Germany | |
| 59-113 024-A | 6/1984 | Japan | |
| WO 88/02661 | 4/1988 | WIPO | B01J 31/26 |
| WO 94/19392 | 9/1994 | WIPO | |

OTHER PUBLICATIONS

Olah, G.A. et al, *J. Appl. Polym. Sci.*, 45, 1355–1360 (1992).
Hrkach et al, *Macromolecules*, 23, 4042–4046 (1990).
Dreyfuss et al, *Polymer Letters* Ed., 14, 139–142 (1976).
Matsukura et al, *Chemical Abstracts*, 78(16), Apr. 23, 1973; Abstract No. 98454j.
Borowsky et al, *Organometal*, 10, 1268–1274 (1991).
Christen, H.R., "Grundlagen der Organischen Chemie", 4. Auflage, (1977), p. 386, Otto Salle Verlag und Verlag Säverlander.
Lee, H. et al, *Handbook of Epoxy Resins*, McGraw–Hill Book Co., New York, NY, Section 15–14 (Reissue 1982).
Lenz, R.W., *Organic Chemistry Synthetic High Polymers*, Interscience Publishers, New York, NY, 531–532 (1967).
Bowden, K. *Chem. Rev.*, 66(2), 119–131 (1966).
Hayase, S. et al, *Macrolecules*, 18(10), 1799–1804 (1985).
Crivello, J.V. et al, "Novel Platinum Initiators for Ring–Opening Polymerizations", DIE Makromol. Chemie: Macromolecular Symposia, No. 54/55, (1992), BAsel, CH, pp. 179–188.

(List continued on next page.)

*Primary Examiner*—Mark Nagumo

[57] ABSTRACT

A process for polymerizing oxiranes, oxetanes, oxepanes, dioxolanes, trioxanes, and tetrahydrofurans to their respective polymers by contacting them with a selected metal compound is disclosed; and also a process for depolymerizing polytetrahydrofurans to monomeric tetrahydrofurans by contacting the polymer with a selected metal compound at a temperature of about 100° C. to about 250° C. The catalysts may be in solution or part of a heterogeneous solid, and selected organic compounds are used as accelerators in the polymerizations. The polymeric products, some of which are novel, may be used as polyether monomers for further polymerization, as by reaction with isocyanates to produce polyurethanes, and other useful polymers. Some of the polymeric products are relatively high in molecular weight and are suitable for direct use, for instance as spandex fibers.

36 Claims, No Drawings

OTHER PUBLICATIONS

Maeda, S. et al, *Chemical Abstracts*, 85(18), Nov. 1, 1976, Abstract No. 124661r.

Hilt, et al, *Makromol Chem.*, 101, 246–270 (1967) (English translation).

Habermeier, J. et al, *J. Poly. Science: Part C*, 16, 2131–2141 (1967) (English Abstract).

Oechsner et al, *Makromol Chem.*, 150, 1–23 (1971) (English Abstract).

WPI Derwent Acc. No. 94–068607 (1994).

WPI Acc. No. 76–67625x/36 (1976).

WPI Acc. No. 86–187083 (1986).

WPI Acc. No. 87–337120 (1987).

POLYMERIZATION OF, AND DEPOLYMERIZATION TO, CYCLIC ETHERS USING SELECTED METAL COMPOUND CATALYSTS

This is a continuation of application Ser. No. 08/424,675, filed Apr. 19, 1995, now U.S. Pat. No. 5,635,585, which in turn is a division of Ser. No. 08/283,108 filed Jul. 29, 1994, now abandoned; which is, in turn, a continuation-in-part of Ser. No. 08/198,024 filed Feb. 17, 1994, now abandoned; Ser. No. 08/141,160 filed Oct. 21, 1993, now abandoned; PCT/US93/09808 filed Oct. 20, 1993; Ser. No. 08/093,243 filed Jul. 16, 1993, now abandoned; Ser. No. 08/093,119 filed Jul. 16, 1993, now abandoned; Ser. No. 08/021,368 filed Feb. 23, 1993, now abandoned; and Ser. No. 07/964,313 filed Oct. 21, 1992, now abandoned.

FIELD OF THE INVENTION

This invention concerns the polymerization of oxiranes, oxetanes, oxepanes, 1,13-dioxolanes, 1,3,5-trioxanes, and tetrahydrofurans to linear polyethers, and the depolymerization of polytetrahydrofurans to tetrahydrofurans, both catalyzed by selected metal compounds. The catalysts may be in solution or part of a heterogeneous solid, and selected organic compounds are used as accelerators in the polymerizations. Novel polymeric products are produced in some of the polymerizations.

BACKGROUND OF THE INVENTION

Cyclic ethers are polymerized by various means to give products of widespread utility. For instance, ethylene oxide is polymerized to polyethylene oxide which is useful, in lower molecular weight grades, for ceramics (as a binder), cosmetics, lubricants, polyurethanes; and in higher molecular weight grades, for packaging film, denture adhesives, lubricants, flocculation and for other articles and products. Tetrahydrofuran (THF) is polymerized to poly (tetramethylene ether) glycol which is useful in the preparation of Spandex fibers; polyurethane resins which are useful in elastomeric parts; and thermoplastic elastomers which are useful for molding various mechanical parts. Therefore, improved methods of making these polymers are sought. Also useful are methods of depolymerizing the polyethers to useful products, such as the cyclic ethers from which they were originally made. Such depolymerizations allow for the recycle of off specification or used polyethers to useful products such as polyethers, thereby reducing waste.

Block copolymers, of polytetrahydrofurans (usually as the diols) and polyesters or poly(urea-urethanes) are commonly used in commercial products, such as thermoplastic elastomers (Hytrel® thermoplastic elastomer), spandex fibers (Lycra® spandex fiber) and urethane rubbers (Adiprene® urethane rubber). The usual procedure in making these products is to combine a polyether diol with suitable reactants, such as ester segment forming compounds, or urea and/or urethane forming compounds such as amines and/or diols with diisocyanates. Improved methods of making such commercially important polymers are sought by the artisan.

U.S. Pat No. 3,842,019 describes the polymerization of oxiranes and other small ring compounds by a presumed cationic mechanism, using as the catalyst the decomposition products of metal perfluoroalkylsulfonates. These catalysts are described as "latent", that is no reaction occurs until the metal salt is decomposed. The reactions reported are relatively slow, even at elevated temperatures.

U.S. Pat. Nos. 5,084,586 and 5,124,417 describe the cationic polymerization of various monomers, including cyclic ethers, using onium cations, whose corresponding anions are fluoroalkylsulfatometallates. Onium ion catalyzed cationic polymerizations are well known, and there is no mention in these patents of the use of metal salts not containing onium ions, such as metal triflates, as catalysts for the polymerization of cyclic ethers.

Japanese Patent Application 51-82397 describes the polymerization of tetrahydrofuran using a combination of fluorosulfonic acid and a carboxylic acid as catalysts. No mention is made of metal salts, such a metal triflates as catalysts.

J. S. Hrkach, et al., Macromolecules, vol. 23, p. 4042–4046 (1990) describe the polymerization of tetrahydrofuran using trimethylsilyl trifluoromethanesulfonate as the initiator. No mention is made of any other triflates as catalysts for this polymerization.

German Patent Application 2,459,163 describes the polymerization of THF using a combination of ferric chloride and carboxylic anhydride as catalyst.

G. A. Olah, et al., J. Appl. Polym. Sci., Vol. 45, 1355–1360 (1992) describe the use of boron, aluminum and gallium tristriflate to catalyze the polymerization of THF.

S. L. Borkowsky, et al., Organometal., Vol. 10, p. 1268–1274 (1991) report that certain zirconium tetrahydrofuran. No mention is made of zirconium perfluoroalkylsulfonates, or of copolymers.

T. Misaki, et al., Nippon Kagaku Kaishi, p. 168–174 (1973) report on the polymerization of THF using a combination of metal aceylacetonates and acetyl chloride.

U.S. Pat. No. 4,303,782 describes the use of zeolites to catalyze the polymerization of tetrahydrofuran. These polymerization appear to proceed very slowly.

SUMMARY OF THE INVENTION

This invention concerns a first process for the polymerization of cyclic ethers, comprising, contacting at a temperature of about −80° C. to about 150° C. one or more oxiranes, oxetanes, tetrahydrofurans, oxepanes, 1,3-dioxolanes or 1,3,5-trioxanes with a catalyst system consisting essentially of a compound of the formula $MZ_s \cdot Q_t$, and an accelerator selected from the group consisting of carboxylic acids whose pKa in water is less than 6, carboxylic anhydrides and acyl halides, wherein:

M is a metal selected from the group consisting of cobalt, vanadium, copper, mischmetall, niobium, tungsten, strontium, barium, scandium, yttrium, the rare earth metals, titanium, zirconium, hafnium, chromium, molybdenum, tantalum, rhenium, iron, ruthenium, osmium, rhodium, iridium, palladium, platinum, gold, zinc, cadmium, mercury, aluminum, gallium, indium, thulium, germanium, tin, lead, arsenic, antimony and bismuth;

at least one of Z is an anion of the formula $R^5SO_3$, wherein $R^5$ is perfluoroalkyl containing 1 to 12 carbon atoms or part of a fluorinated polymer wherein the carbon atoms alpha and beta to the sulfonate group are together bonded to at least four fluorine atoms, or tetraphenylborate, and the remainder of Z is oxo or one germanium, tin, lead, arsenic, antimony and bismuth;

s is 2 when M is strontium, barium, cobalt, rhodium, copper, iridium, palladium, platinum, chromium, zinc, cadmium or mercury;

s is 3 when M is scandium, yttrium, a rare earth metal, arsenic, antimony, bismuth, gold, iron, ruthenium, mischmetall, osmium, aluminum, gallium, indium or thulium;

s is 4 when M is titanium, zirconium, hafnium, molybdenum, germanium, tin, or lead;

s is 5 when M is rhenium, vanadium, niobium or tantalum;

s is 6 when M is tungsten;

Q is a neutral ligand;

t is 0 or an integer of 1 to 6; and provided that each oxo group present counts as two of s.

This invention also involves a first process for the depolymerization of a polyether to a tetrahydrofuran, comprising, contacting at a temperature of about 100° C. to about 250° C., a polymer consisting essentially of one or more repeat units of the formula

—[CHR$^1$CR$^2$R$^3$CR$^2$R$^3$CHR$^4$O]— with a compound of the formula MZ$_3$.Q$_t$, wherein:

each R$^1$, R$^2$, R$^3$ and R$^4$ is independently hydrogen or hydrocarbyl containing 1 to 20 carbon atoms;

M is a metal selected from the group consisting of cobalt, vanadium, copper, mischmetall, niobium, tungsten, strontium, barium, scandium, yttrium, the rare earth metals, titanium, zirconium, hafnium, chromium, molybdenum, tantalum, rhenium, iron, ruthenium, osmium, rhodium, iridium, palladium, platinum, silver, gold, zinc, cadmium, mercury, aluminum, gallium, indium, thulium, silicon, germanium, tin, lead, arsenic, antimony and bismuth;

at least one of Z is an anion of the formula R$^5$SO$_3^-$, wherein R$^5$ is perfluoroalkyl containing 1 to 12 carbon atoms or part of a fluorinated polymer wherein the carbon atoms alpha and beta to the sulfonate group are together bonded to at least four fluorine atoms, or tetraphenylborate, and the remainder of Z is oxo or one or more monovalent anions;

s is 1 when M is silver;

s is 2 when M is strontium, barium, cobalt, rhodium, copper, iridium, palladium, platinum, chromium, zinc, cadmium or mercury;

s is 3 when M is scandium, yttrium, a rare earth metal, arsenic, antimony, bismuth, gold, iron, ruthenium, mischmetall, osmium, aluminum, gallium, indium or thulium;

s is 4 when M is titanium, zirconium, hafnium, molybdenum, silicon, germanium, tin, or lead;

s is 5 when M is rhenium, vanadium, niobium or tantalum;

s is 6 when M is tungsten;

Q is a neutral ligand;

t is 0 or an integer of 1 to 6;

and provided that each oxo group present counts as two of s.

This invention also concerns a second process for the polymerization of cyclic ethers, comprising, contacting one, at a temperature of about −80° C. to about 130° C., or more oxiranes, oxetanes, tetrahydrofurans, oxepanes, 1,3-dioxolanes, or 1,3,5-trioxanes; with a zeolite which contains a metal cation selected from the group consisting of strontium, vanadium, copper, mischmetall, niobium, tungsten, cobalt, barium, scandium, yttrium, the rare earth metals, titanium, zirconium, hafnium, chromium, molybdenum, tantalum, rhenium, iron, ruthenium, osmium, rhodium, iridium, palladium, platinum, silver, gold, zinc, cadmium, mercury, aluminum, gallium, indium, group consisting of strontium, vanadium, niobium, bismuth; and an accelerator selected from the group consisting of carboxylic anhydrides, acyl halides and carboxylic acids whose pKa in water is less than about 6.

This invention also concerns a third process for the polymerization of cyclic ethers, comprising, contacting, at a temperature of about −80° C. to about 130° C., one or more oxiranes, oxetanes, tetrahydrofurans, oxepanes, 1,3-dioxolanes, or 1,3,5-trioxanes; with a catalytic system consisting essentially of a heterogeneous catalyst containing a metal perfluoroalkylsulfonate attached to the surface of said catalyst through said metal, and an accelerator; said metal selected from the group consisting of strontium, vanadium, copper, mischmetall, niobium, tungsten, cobalt, barium, scandium, yttrium, the rare earth metals, titanium, zirconium, hafnium, chromium, molybdenum, tantalum, rhenium, iron, ruthenium, osmium, rhodium, iridium, palladium, platinum, gold, zinc, cadmium, mercury, indium, thulium, germanium, tin, lead, arsenic, antimony and bismuth; said accelerator selected from the group consisting of carboxylic anhydrides, acyl halides, and carboxylic acids whose pKa in water is less than about 6.

This invention also concerns a second process for the depolymerization of a polyether to a tetrahydrofuran, comprising, contacting at a temperature of about 100° C. to about 250° C., a polymer consisting essentially of one or more repeat units of the formula

[—CHR$^1$CR$^2$R$^3$CR$^2$R$^3$CHR$^4$O]— wherein each R$^1$, R$^2$, R$^3$ and R$^4$ is independently hydrogen or hydrocarbyl containing 1 to 20 carbon atoms, with a heterogeneous catalytic system consisting essentially of a catalyst containing a metal perfluoroalkylsulfonate attached to the surface of said catalyst through said metal; said metal selected from the group consisting of strontium, vanadium, copper, mischmetall, niobium, tungsten, cobalt, barium, scandium, yttrium, the rare earthe metals, titanium, zirconium, hafnium, chromium, silver, molybdenum, tantalum, rhenium, iron, ruthenium, osmium, rhodium, iridium, palladium, platinum, silver, gold, zinc, cadmium, mercury, aluminum, gallium, indium, thulium, germanium, tin, lead, arsenic, antimony and bismuth.

This invention also concerns a fourth polymerization process for the production of poly(ether-esters), comprising, contacting a tetrahydrofuran with a catalyst system consisting essentially of a polycarboxylic acid of the formula A(CO$_2$H)$_x$ and a catalyst of the formula MZ$_s$.Q$_t$, wherein:

M is a metal selected from the group consisting of cobalt, tungsten, vanadium, niobium, strontium, barium, scandium, yttrium, the rare earth metals, titanium, zirconium, hafnium, chromium, molybdenum, tantalum, rhenium, iron, ruthenium, osmium, rhodium, iridium, palladium, platinum, silver, gold, zinc, cadmium, mercury, indium, thulium, germanium, tin, lead, arsenic, antimony and bismuth;

Z is an anion of the formula R$^5$SO$_3^-$, wherein R$^5$ is perfluoroalkyl containing 1 to 12 carbon atoms or part of a fluorinated group wherein the carbon atoms alpha and beta to the sulfonate group are together bonded to at least four fluorine atoms;

s is 1 when M is silver, s is 2 when M is strontium, barium, cobalt, rhodium, iridium, palladium, platinum, chromium, zinc, cadmium or mercury;

s is 3 when M is scandium, yttrium, a rare earth metal, arsenic, antimony, bismuth, gold, iron, ruthenium, osmium, aluminum, gallium, indium or thulium;

s is 4 when M is titanium, zirconium, hafnium, molybdenum, germanium, tin, or lead;

s is 5 when M is rhenium, vanadium, niobium or tantalum;

s is 6 when M is tungsten;

Q is a neutral ligand;

t is 0 or an integer of 1 to 6; and each A is independently an organic radical having x free valencies;

each x is independently 2, 3, 4, 5 or 6; and provided that:

A is bound to carboxyl groups through a carbon atom;

said polycarboxylic acid has a pKa of about 6 or less;

said polycarboxylic acid does not by itself catalyze polymerization of the tetrahydrofuran; and the ratio of equivalents of carboxyl groups of said polycarboxylic acid to moles of said catalyst is less than 6.

This invention also concerns a polymer consisting essentially of a repeat unit of the formula

[(—CHR$^1$CR$^2$R$^3$CR$^2$R$^3$CHR$^4$O—)$_n$C(O)AC(O)O—]

wherein:

each R$^1$, R$^2$, R$^3$ and R$^4$ is hydrogen or hydrocarbyl containing 1 to 20 carbon atoms;

each n is independently an integer of 1 or more;

each A is independently hydrocarbylene or substituted hydrocarbylene containing one or more functional groups selected from the group consisting of imide, amide, urea and urethane;

and provided that each A is bound to an ester group through a carbon atom.

DETAILS OF THE INVENTION

In the first polymerization process described herein one or more cyclic ethers, oxiranes, oxetanes, 1,3-dioxolanes, 1,3,5-trioxanes, or tetrahydrofurans are functional groups selected from the group consisting of herein, oxirane (more commonly called epoxide) is herein given its usual structure, a saturated three membered ring containing two carbon atoms and one oxygen atom. Oxetane is also given its common meaning, a saturated four membered ring containing three carbon atoms and one oxygen atom. The term oxepane means a saturated seven membered ring containing six carbon atoms and one oxygen atoms. The term 1,3-dioxolane means a saturated five membered ring which contains two oxygen atoms separated by 1 carbon atom. The term 1,3,5-trioxane means a six membered ring containing 3 oxygen atoms in which the oxygen atoms and carbons atoms are alternated. All of these terms include compounds containing those ring systems which are substituted with hydrocarbyl or hydrocarbylene groups containing 1 to 20 carbon atoms. The hydrocarbylene groups may form carbocyclic rings, which include bicyclic, tricyclic, etc., systems. By a hydrocarbylene group herein is meant a divalent radical containing carbon and hydrogen which is part of a carbocyclic ring.

Preferred cyclic ethers for the first polymerization have the formula

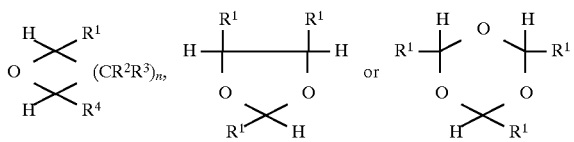

wherein n is 2 or 4 and each R$^1$, R$^2$, R$^3$ and R$^4$ is independently hydrogen or hydrocarbyl containing 1 to 20 carbon atoms. Some of these cyclic ethers polymerize to give repeat units of the formula —[CHR$^1$(CR$^2$R$^3$)$_n$CHR$^4$O]

—. In a more preferred cyclic ether all of R$^1$, R$^2$, R$^3$ and R$^4$ are hydrogen. In another more preferred cyclic ether where n=2, R$^1$, one of R$^2$, both of R$^3$ and R$^4$ are hydrogen, and the remaining R$^2$ is alkyl containing 1–4 carbon atoms, especially preferably the remaining R$^2$ is methyl. By hydrocarbyl herein is meant a univalent radical containing carbon and hydrogen.

The first polymerization is run in the presence of an accelerator. Suitable accelerators are carboxylic anhydrides, acyl halides, and carboxylic acids with a pk$_a$ of less than about 6 in water.

By a carboxylic anhydride is meant a compound containing the grouping —C(O)O(O)C—, wherein the free valencies are to other carbon atoms. A preferred carboxylic anhydride is an anhydride of an alkyl carboxylic acid or a halogen substituted alkyl carboxylic acid, and particularly preferred anhydrides are acetic anhydride and trifluoroacetic anhydride.

By an acyl halide is meant a compound containing the grouping —C(O)X, where X is chlorine or bromine and the free valence is to another carbon atom. In preferred acyl halides, X is chlorine. Preferred acyl halides are alkyl acyl halides, and especially preferred are acetyl halides, more preferably acetyl chloride.

By a carboxylic acid is meant a compound containing the grouping —C(O)OH, wherein the free valence is to another carbon atom. Preferred carboxylic acids have a pKa of less than 5 in water. Useful carboxylic acids include, but are not limited to acetic, trifluoroacetic, chloroacetic, benzoic, trichloroacetic, p-nitrobenzoic, butyric, formic, cyanoacetic, nitropropionic, acrylic, methacrylic, and napthoic acids. Preferred carboxylic acids are trifluoroacetic, acetic, formic, cyanoacetic, nitropropionic, acrylic and methacrylic acids.

When carboxylic anhydride is present one half or more of the end groups are carboxylic esters. As is known to the artisan, these may be hydrolyzed to hydroxyl groups nby-reaction with water, preferably in the presence of a catalyst, such as a strong acid (sulfuric acid for instance) or a strong base (such as NaOH). The proportion of acetate ends increases the longer the polymerization is allowed to proceed. Although the polymeric diol is often the desired product (it can be used to make other polymers, such as polyurethanes and polyesters), the half ester or diester is also useful, as in relatively low molecular polymers which can be used as solvents.

When an acyl halide is used as the accelerator, the end groups are usually ester on one end, and the halide, X, on the other. Thus the complete formula for such a polymer could be X—[CHR$^1$(CR$^2$R$^3$)$_n$CHR$^4$O]—C(O)Y, where Y is the group to which the acyl group of the acyl halide was bound. Such polymers are useful as intermediates for the preparation of polymers containing different functional groups. For example, the ester may be hydrolyzed to a hydroxyl group, and the halide may be reacted to form another functional group such as nitrile. If a bis(acyl halide), X(O)CYC(O)X, is used as the accelerator, the product of the polymerization will be a polyether with halide (X) end groups which contains two internal ester groups, and may have the formula X—[CHR$^1$(CR$^2$R$^3$)$_n$CHR$^4$O]—C(O)YC(O)—[OCHR$^1$(CR$^2$R$^3$)$_n$CHR$^4$]—X. Useful bis(acyl halides) include adipoyl chloride, terephthaloyl chloride, and diglycolyl chloride [Cl(O)CCH$_2$OCH$_2$C(O)Cl].

In the first polymerization when a carboxylic acid is used as the accelerator, both end groups are usually mostly ester. Thus the complete formula for such a polymer could be Y(O)CO—[CHR$^1$(CR$^2$R$^3$)$_n$CHR$^4$O)—C(O)Y, where Y is the group to which the acyl group of the carboxylic acid was bound.

An important consideration in the preparation of polyesters is the number average molecular weight (Mn) of the polyether and its molecular weight distribution. When the polyether is to be used as a monomer in the preparation of another polymer (usually in the diol form), it is often preferred in the first polymerization that the Mn of the polyether be in the range of about 400 to about 20,000, preferably about 500 to about 5,000.

In the first polymerization the catalyst may be yttrium or rare earth compound of the formula $MZ_3$ where M is a trivalent ion of yttrium, or one of the rare earths, lanthanum, cerium, praeseodymium, neodymium, promethium, samarium, europium, gadolinium, terbium, dysprosium, holmium, erbium, thulium, ytterbium, and lutetium.

In the first polymerization preferred metals, M, are strontium, scandium yttrium, the rare earth metals, titanium, zirconium, hafnium, vanadium, niobium, tantalum, chromium, molybdenum, tungsten, rhenium, iron, ruthenium, palladium, copper, gold, zinc, tin and bismuth. More preferred metals are yttrium, the rare earth metals, and scandium. Especially preferred metals are yttrium, ytterbium, dysprosium, erbium, neodymium, lanthanum, and scandium. Another preferred metal is "mischmetall" (sometimes also called "didymium"), which is a mixture of rare earth metals as obtained from the ore.

It is believed monovalent anions that are relatively non-nucleophilic are useful as Z. Examples of such anions are tetraphenylborate, $R^5SO_3^-$, wherein $R^5$ is perfluoroalkyl, or wherein $R^5$ is part of a fluorinated polymer wherein the carbon atoms alpha and beta to a sulfonate group are together bonded to at least 4 fluorine atoms (as in —$CF_2CF_2SO_3^-$). It is preferred if $R^5$ is perfluoroalkyl. In a particularly preferred $R^5$ is trifluoromethyl, and the anion is herein called "triflate".

Generally speaking, in the first polymerization any metallic compound in which the correct metal in the correct oxidation state (see above) is present and bonded to a triflate or similar anion will be a catalyst. Such a compound must of course be reasonably stable during the polymerization (or depolymerization, see below), or decompose to another compound which is still a triflate (or similar anion) compound of the metal in the correct oxidation state. It has been found that, in general, the greater the number of triflate groups bonded to the metal cation, the more active the metal compound will be as a catalyst. It is preferred if half or more of the anions (Z) bound to each metal cation is triflate or a similar anion.

The metal catalysts of the first polymerization may optionally contain one or more neutral ligands coordinated to the metal. By a neutral ligand is meant a neutral compound that can coordinate with the catalysts, usually the metal cation. Neutral ligands include water, and ethers such as dimethyl ether and tetrahydrofuran.

The metals catalysts of the first polymerization may contain other anions than triflate and similar anions, and tetrafluoroborate, although at least one of triflate or tetrafluoroborate anions must be present. Some other useful anions are alkoxide, particularly lower alkoxide containing 1–4 carbon atoms, acetylacetonate, cyclopentadieneide, pentamethylcyclopentadieneide, t-butylacetylacetonate, and halide. It is preferred if all of the anions are triflate.

In general, in the first polymerization the higher the molar ratio of metal compound to cyclic ether monomer originally present, the lower the molecular weight of the resulting polyether will be. Similarly, the higher the ratio of accelerator (if present) to monomer originally present, the lower the molecular weight of the polyether will be. It is believed the effects of these two ratios are cumulative. For these effects see Examples 7 and 8.

The first polymerization may be run at a temperature of about –80° C. to about 130° C. If this temperature is above the boiling point of the cyclic ether monomer, a pressure vessel may be used. A preferred temperature is ambient to the boiling point of the monomer, or 110° C., whichever is lower. An inert solvent such as di-n-butyl ether, diethyl ether or toluene may be used, but it is preferred if solvents are not present. Protic compounds such as water, methanol and ethanol should preferably not be present, and it is convenient to exclude them by drying the starting materials and keeping the process under an inert dry gas such as nitrogen. As in most chemical processes, the ingredients should be mixed at least initially. Continued agitation is preferred to assure that the process materials remain well mixed, and to avoid overheating. The polymerization is mildly exothermic. If the polymerization temperature goes up appreciably, refluxing of the monomer may be used to help cool the process.

The polymers produced in the first polymerization often have polydispersities significantly less than 2, which is possibly indicative of a "Living polymerization". Also indicative of this is the fact that as the polymerization proceeds, the molecular weight, particularly the number average molecular weight, increases.

In the second and third polymerizations, the terms oxirane, oxetane, oxepane, 1,3-dioxolane, 1,3,5-trioxane, and tetrahydrofuran include compounds containing those ring systems which are substituted with hydrocarbyl or hydrocarbylene groups containing 1 to 20 carbon atoms. The hydrocarbylene groups form carbocyclic rings, which include bicyclic, tricyclic, etc. systems. By a hydrocarbylene group herein is meant a divalent radical containing carbon and hydrogen which is part of a carbocyclic ring.

In the second and third polymerizations preferred cyclic ethers have the formula

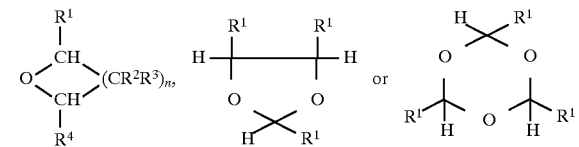

wherein n is 2 or 4, and each $R^1$, $R^2$, $R^3$ and $R^4$ is independently hydrogen or hydrocarbyl containing 1 to 20 carbon atoms. Some cyclic ethers polymerize to give repeat units of the formula —$[CHR^1(CR^2R^3)_nCHR^4O]$—. In a more preferred cyclic ether all of $R^1$, $R^2$, $R^3$ and $R^4$ are hydrogen. In another more preferred cyclic ether where n=2, $R^1$, one of $R^2$, both of $R^3$ and $R^4$ are hydrogen, and the remaining $R^2$ is alkyl containing 1–4 carbon atoms, especially preferably the remaining $R^2$ is methyl. By hydrocarbyl herein is meant a univalent radical containing carbon and hydrogen.

The second and third polymerizations are carried out in the presence of an accelerator (sometimes also called a co-catalyst). Suitable accelerators are carboxylic anhydrides, acyl halides and carboxylic acids whose pKa is less than about 6 in water.

By a carboxylic anhydride is meant a compound containing the grouping —C(O)O(O)C—, wherein the free valencies are to other carbon atoms. A preferred carboxylic anhydride is an anhydride of an alkyl carboxylic acid or a halogen substituted alkyl carboxylic acid, and particularly preferred anhydrides are acetic anhydride and trifluoroacetic anhydride.

By a carboxylic anhydride is meant a compound containing the grouping —C(O)X, where X is chlorine or bromine and the free valence it to another carbon atom. In preferred acyl halides X is chlorine. Preferred acyl halides are alkyl acyl halides, and especially preferred are acetyl halides, more preferably acetyl chloride.

In the second and third polymerizations, by a carboxylic acid is meant a compound containing the grouping —C(O)OH, wherein the free valence is to another carbon atom. Preferred carboxylic acids have a pKa of less than 5 in water. Useful carboxylic acids include, but are not limited to formic, acetic, trifluoroacetic, chloroacetic, benzoic, trichloroacetic, p-nitrobenzoic, butyric, and naphthoic acids. Preferred carboxylic acids are trifluoroacetic, formic, acetic, cyanoacetic, nitropropionic, nitrobenzoic, acrylic and methacrylic. These and other acids that themselves don't cause polymerization of the cyclic ethers are also believed to be accelerators, especially if their pKa in water is about 6 or less.

When carboxylic anhydride is present one half or more of the end groups are carboxylic esters. As is known to the artisan, these may be hydrolyzed to hydroxyl groups by reaction with water, preferably in the presence of a catalyst, such as a strong acid (sulfuric acid for instance) or a strong base (such as NaOH). The proportion of acetate ends increases the longer the polymerizationis allowed to proceed. Although the polymeric diol is often the desired product (it can be used to make other polymers, such as polyurethanes and polyesters), the half ester or diester is also useful, as in relatively low molecular weight polymers which can be used as solvents.

When acyl halides are used as the accelerator, the end groups are usually ester on one end, and the halide, X, on the other. Thus the complete formula for such a polymer could be X—[CHR$^1$(CR$^2$R$^3$)$_n$CHR$^4$O]—C(O)Y, where Y is the group to which the acyl group of the acyl halide was bound. Such polymers are useful as intermediates for the preparation of polymers containing different functional groups. For example, the ester may be hydrolyzed to a hydroxyl group, and the halide may be reacted to form another functional group such as nitrile. If a bis(acyl halide), X(O)CYC(O)X, is used as the accelerator, the product of the polymerization will be a polyether with halide (X) end groups which contains two internal ester groups, and may have the formula X—[CHR$^1$(CR$^2$R$^3$)$_n$CHR$^4$O]—C(O)YC(O)—[OCHR$^1$(CR$^2$R$^3$)$_n$CHR$^4$]—X. Useful bis(acyl halides) include adipoyl chloride, terephthaloyl chloride, and diglycolyl chloride [Cl(O)CCH$_2$OCH$_2$C(O)Cl].

In the second and third polymerizations, when a carboxylic acid is used as the accelerator, the end groups are usually mostly ester. Thus the complete formula for such a polymer could be Y—C(O)—O—[CHR$^1$(CR$^2$R$^3$)$_n$CHR$^4$O]—C(O)Y, where Y is the group to which the acyl group of the carboxylic acid was bound. The ester group may be hydrolyzed as described above in the paragraph describing the products when a carboxylic anhydride is used as the accelerator.

The second and third polymerizations may be run at a temperature of about –80° C. to about 130° C. If this Useful bis(acyl halides) include adipoyl chloride, temperature is above the boiling-point of the cyclic ether monomer, a pressure vessel may be used. A preferred temperature is ambient to the boiling point of the monomer or 110° C., whichever is lower. An inert solvent such as di-n-butyl ether, diethyl ether or toluene may be used, but it is preferred if solvents are not present. Protic compounds such as water, methanol and ethanol should preferably not be present, and it is convenient to exclude them by drying the starting materials and keeping the process under an inert dry gas such as nitrogen or dry air. As in most chemical processes, the ingredients should be mixed. Continued agitation is preferred to assure contact of the process liquids with the heterogeneous catalyst, and to avoid overheating. The polymerization is mildly exothermic. If the polymerization temperature goes up appreciably, refluxing of the monomer may be used to help cool the process.

The second and third polymerizations may be run in a variety of methods, such as batch, semi-continuous, or continuous. While the heterogeneous catalyst may be recovered each time, as by filtration, and reused, in another embodiment the catalyst is fixed in place and the polymerization mass circulated or agitated so that uniform contact with the catalyst surface is obtained. In this way, the catalyst may be used for long periods in a continuous process, or for many batches in a batch polymerization, without the need to recover the catalyst. Contact time of the liquid reaction mass with the catalyst will depend on many factors, such as the catalytic metal used, its concentration on the catalyst, the temperature, cyclic ether being polymerized, etc., but will usually be in the range of a few minutes to a few hours.

Catalysts used herein in the second and third polymerizations contain selected metal cations. Preferred metal cations are those of strontium, scandium, yttrium, the rare earth metals, titanium, zirconium, hafnium, vanadium, niobium, tantalum, chromium, molybdenum, tungsten, rhenium, iron, ruthenium, palladium, copper, gold, zinc, tin and bismuth. More preferred metals are yttrium, the rare earth metals, scandium and zirconium. Especially preferred metals are yttrium, ytterbium, dysprosium, erbium, neodymium, lanthanum, scandium and zirconium. Another preferred metal is "mischmetall" (sometimes also called "didymium"), which is a mixture of rare earth metals as obtained from the ore. By rare earths herein is meant lanthanum, cerium, praeseodymium, neodymium, promethium, samarium, europium, gadolinium, terbium, dysprosium, holmium, erbium, thulium, ytterbium, and lutetium. By a perfluoroalkylsulfonate herein is meant a metal salt of a perfluoroalkylsulfonate in which the metal is bonded to one or more perfluoroalkylsulfonate groups.

The catalyst used in the second polymerization herein is a zeolite in which some of the metal cations present are the cations listed above. The anions of such cations are not critical, and may be those normally found in zeolites. The zeolites containing the appropriate metal cations can be made by the ion exchange of cations in known zeolites. Such ion exchange processes are know to the artisan, see for instance D. W. Breck in Zeolite Molecular Sieves, R. E. Krieger Publishing Co., Malabar, Fla., 1984 and Examples 7, 9, 12, 14, 16, 18, and 20. It is preferred if at least 0.5 atom percent of the metals and metalloids in the zeolite are one of the useful "catalytic" metals, more preferably at least 5 atom percent. It has been found that the zeolite catalysts usually yield polyethers with bimodal molecular weight distributions.

The catalyst of the third polymerization, a "catalytic" metal perfluoroalkylsulfonate is attached to the surface of a material that in effect acts as a heterogeneous support for the metal perfluoroalkylsulfonate. The metal is not attached to the surface through the perfluoroalkylsulfonate, but through another bond or ligand. The catalytic metal should have at least one perfluoroalkylsulfonate anion attached to it, and preferably, except for the group attaching the metal to the support surface, all of the groups should be perfluoroalkylsulfonate.

In the third polymerization catalyst, the metal may be attached to the surface by a covalent bond, or coordination, or any other method. It is preferred if significant amounts. (>25%, preferably <10%) of the catalytic metal cannot be leached from the heterogeneous catalyst by the polymerization process liquids. In one method of attachment, a ligand which can coordinate with the metal cation is attached via one or more covalent bonds to the surface of the support, and then the metal cation is coordinated to the ligand, thereby fixing the metal cation on the support surface. Particularly useful for such are silicon compounds to which the ligand is attached by a stable (to hydrolysis and the polymerization process conditions) bond, and in which the silicon is directly attached to groups which are readily hydrolyzed. When these hydrolytically unstable groups are hydrolyzed from the silicon atom, the resulting "compound" can readily bond to surfaces which have hydroxyl groups present. Many common supports, such as alumina, silica (gel), many metal oxides, and the metal cation is attached via one or more covalent to the surface, an appropriate metal compound is contacted with the surface containing the ligands, and the metal cation becomes fixed to the support surface. See Examples 177, 179, 181, and 183 for such processes.

The heterogeneous supports for such third polymerization catalysts can be those which are commonly used for supported catalysts. It is preferred if they have a relatively large surface area, at least 25 m²/gm, and it is also preferred if the support is inorganic (inorganic includes various forms of carbon, such as activated carbon, graphite, etc.). Useful supports include alumina, silica, silica-aluminates, carbon, zirconia, yttria, magnesia, ceria, aluminum fluoride and barium sulfate. Preferred supports are alumina, silica, silica-aluminates, carbon and zirconia. It is preferred if the supports themselves are acidic. Although not critical, a convenient amount of the catalytic metal on the catalyst is about 0.1 to about 20 weight percent, measured as catalytic metal.

In the fourth polymerization process a tetrahydrofuran is copolymerized with a polycarboxylic acid to yield a poly (ether-ester). By a tetrahydrofuran (THF) is meant the common meaning, a compound containing a saturated five membered ring in which one of the ring atoms is oxygen and the other four ring atoms are carbon. Preferred tetrahydrofurans have the formula I

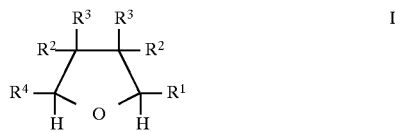

wherein each $R^1$, $R^2$, $R^3$ and $R^4$ is independently hydrogen or hydrocarbyl containing 1 to 20 carbon atoms. In especially preferred THFs, $R^1$, one of $R^2$ and all of $R^3$ and $R^4$ are hydrogen, and the remaining $R^2$ is alkyl containing 1–4 carbon atoms, particularly the remaining $R^2$ is methyl. In another especially preferred embodiment all of $R^1$, $R^2$, $R^3$ and $R^4$ are hydrogen.

In the fourth polymerization a tetrahydrofuran is copolymerized with a polycarboxylic acid of the formula $A(CO_2H)_x$, wherein A is an organic radical, and wherein A is bound to each carboxyl group through a carbon atom. By "through a carbon atom" is meant that each carboxyl group is bound to a carbon atom which is part of A. A may contain any substituent which does not react during, or disturb, the fourth polymerization. Suitable functional groups include halo, ester, amide, urethane, urea, keto, ether, imide, and sulfone, and hydrocarbon based "functional groups" such as olefins, aromatic rings, and acetylenic bonds. Especially preferred functional groups are ester, amide, imide, urethane and urea. The functional groups should be picked so that they don't undergo an acid base reaction with the carboxyl groups of the polycarboxylic acid. Thus aliphatic amine groups should not be present and are classified as among those groups which interfere with the polymerization.

Useful polycarboxylic acids include, but are not limited to, maleic acid, fumaric acid, succinic acid, adipic acid, isophthalic acid, terephthalic acid, and 1,2,4-benzenetricarboxylic acid. Preferred polycarboxylic acids are adipic, isophthalic and terephthalic acids.

The polycarboxylic acid has a pKa of less than 6, preferably less than 5, and should not by itself catalyze the polymerization of the tetrahydrofuran. In preferred polycarboxylic acids, x is 2 (a dicarboxylic acid). When x is more than two, a branched and/or aliphatic amine groups should not be present and are The catalyst for the fourth polymerization may be a yttrium or rare earth compound of the formula $MZ_3$ where M is a trivalent ion of yttrium, or one of the rare earths, lanthanum, cerium, praeseodymium, neodymium, promethium, samarium, europium, gadolinium, terbium, dysprosium, holmium, erbium, thulium, ytterbium, and lutetium.

Preferred metals in the fourth polymerization, M, are strontium, scandium yttrium, the rare earth metals, titanium, zirconium, hafnium, vanadium, niobium, tantalum, chromium, molybdenum, tungsten, rhenium, iron, ruthenium, palladium, copper, gold, zinc, tin and bismuth. More preferred metals are yttrium, the rare earth metals, and scandium. Especially preferred metals are yttrium, ytterbium, dysprosium, erbium, neodymium, lanthanum, and scandium. Another preferred metal is "mischmetall" (sometimes also called "didymium"), which is a mixture of rare earth metals as obtained from the ore.

It is believed monovalent anions that are relatively non-nucleophilic are useful as Z. Examples of such anions are tetraphenylborate, $R^5SO_3^-$, wherein $R^5$ is perfluoroalkyl, or wherein $R^5$ is part of a fluorinated polymer wherein the carbon atoms alpha and beta to a sulfonate group are together bonded to at least 4 fluorine atoms (as in $-CF_2CF_2SO_3^-$). It is preferred if $R^5$ is perfluoroalkyl. In a particularly preferred $R^5$ is trifluoromethyl, and that anion is herein called "triflate".

Generally speaking, any metallic compound in which the correct metal in the correct oxidation state (see above) is present and bonded to a triflate or a similar anion will be a catalyst in the fourth polymerization. Such a compound must of course be reasonably stable relatively nonnucleophilic are useful as Z. Examples of compound which is still a triflate (or similar anion) compound of the metal in the correct oxidation state.

The metal catalysts in the fourth polymerization may optionally contain one or more neutral ligands, Q, coordinated to the metal. By a neutral ligand is meant a neutral compound that can coordinate with the catalysts, usually the metal cation. Neutral ligands include water, and ethers such as dimethyl ether and tetrahydrofuran. Useful compounds containing neutral ligands include bis(n-cyclopentadienyl) tetrahydrofuran-bis(trifluoromethanesulfonate)zirconium and bis(n-cyclopentadienyl)tetrahydrofuran-bis (trifluoromethanesulfonate)hafnium.

In general, in the fourth polymerization the higher the molar ratio of metal compound to cyclic ether monomer originally present, the lower the molecular weight of the resulting polyether will be.

The fourth polymerization may be run at a temperature of about −80° C. to about 130° C. If this temperature is above the boiling point of the cyclic ether monomer, a pressure vessel may be used. A preferred temperature is ambient to the boiling point of the monomer, or 110° C., whichever is lower. An inert solvent such as di-n-butyl ether, diethyl ether or toluene may be used, but it is preferred if solvents are not present. Protic compounds such as water, methanol and ethanol should preferably not be present, and it is convenient to exclude them by drying the starting materials and keeping the process under an inert dry gas such as nitrogen. As in most chemical processes, the ingredients should be mixed at least initially. Continued agitation is preferred to assure that the process materials remain well mixed, and to avoid overheating. The polymerization is mildly exothermic. If the polymerization temperature goes up appreciably, refluxing of the monomer may be used to help cool the process.

The molar ratio of THF to polycarboxylic acid at the beginning of the fourth polymerization can be about 0.2 to about 60, preferably about 2 to about 15. Generally speaking, the higher the relative molar amount of polycarboxylic acid present, the greater the incorporation (per THF unit) of ester units (from polycarboxylic acid) will be. The desired amount of ester present will depend on the polycarboxylic acid used, and the use of the polymeric product.

However, in the fourth polymerization the ratio of equivalents of carboxylic acid groups (in the polycarboxylic acid) to the number of moles of catalyst ($MZ_3.Q_t$) should be less than six (i.e., carboxyl present/moles catalyst <6). In a simple batch reaction this means this ratio will be less than 6 at the start of the polymerization, and decrease as the polycarboxylic acid is polymerized, and its carboxyl groups are "used up" and converted to ester groups. However, as the carboxyl groups are used up by polymerization, they may be replaced by the addition of polycarboxylic acid, so long as the above ratio is less than 6.

In the fourth polymerization when a dicarboxylic acid (x=2) is used in the polymerization, a (product) polymer repeat unit can be represented by the general formula

[(—$CHR^1CR^2R^3CR^2R^3CHR^4O$—)$_n$C(O)AC(O)O—]

wherein all of the symbols have the definitions as given above, and n is an integer of 1 or more. In preferred polymers, n is about 5 to about 500, more preferably about 8 to about 100. Useful A groups include tetramethylene, p-phenylene, and m-phenylene.

In another preferred polymer product of the fourth polymerization, n is 5 or more, more preferably 10 or more. It is preferred if A contains urea or urethane groups. By a urea group is meant —NH—C(O)—$NR^{10}$—, and by a urethane group is meant —O—C(O)—NH—, wherein $R^{10}$ is hydrogen or hydrocarbyl containing 1 to 20 carbon atoms. It is preferred if $R^{10}$ is hydrogen. In other preferred polymers, all of $R^1$, $R^2$, $R^3$ and $R^4$ are hydrogen, or one of $R^2$ is methyl, the other $R^2$ is hydrogen, and all of $R^1$, $R^3$, and $R^4$ are hydrogen.

A preferred polymer product of the fourth polymerization is one in which A has the formula —$R^6$—E—C(O)—NH—$R^7$—NH—C(O)—E—[—$R^8$—E—C(O)—NH—$R^7$—NH—C(O)—E—]$_m$—$R^6$— wherein each $R^6$, $R^7$ and $R^8$ is independently hydrocarbylene or substituted hydrocarbylene containing 2 to 25 carbon atoms, E is —O— or —$NR^{10}$—, wherein $R^{10}$ is as defined above, and m is an average of 0 to 10. Such polymers are made from dicarboxylic acids A(CO$_2$H)$_x$, wherein x is 2, and A has the formula shown above. Such diacids can be made by the reaction of one or more diisocyanates with one or more aminocarboxylic acids, hydroxy carboxylic acids, diamines, aminoalcohols and diols. The group $R^6$ is derived from the amino- or hydroxycarboxylic acid, $R^7$ is derived from an organic diisocyanate, and $R^8$ is derived from a diamine or diol. When a particular E is —O—, it can be derived from the reaction of an isocyanate group and a hydroxy group to form a urethane. When a particular E is —$NR^{10}$—, it can be derived from the reaction of an isocyanate and a primary amino group when $R^{10}$ is hydrogen, and a secondary amino group when $R^{10}$ is hydrocarbyl, to form a urea. All preferred formulas for dicarboxylic acids also refer to "A" in the polymer.

Dicarboxylic acids containing various functional groups can be made by methods known in this art. See, for instance, Chem. Abs., Vol. 44, 5104 b-d (1950), S. Hsiao, et al., J. Polym. Sci., Part A, Vol. 28, pp. 2169–2178 (1990), and R. E. Asay et al., J. Heterocyclic Chem., Vol. 14, pp. 85–90 (1977).

To give a concrete example, if it is desired to make the dicarboxylic acid wherein both of $R^6$ are 1,4-phenylene, $R^7$ is

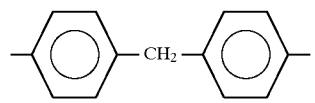

$R^8$ is 1,4-phenylene, every E is —NH—, and m is an average of 1, one could react (preferably in solution) one mole of p-phenylene diamine, two moles of p-aminobenzoic acid, and two moles of bis(4-isocyanatophenyl)methane. To prepare the corresponding polymer where every E is —O—, one would use hydroquinone and p-hydroxybenzoic acid in place of p-phenylenediamine and p-aminobenzoic acid, respectively. To vary m, the ratio of diamine, diol and/or aminomonool to aminocarboxylic acid and/or hydroxyacid would be varied. The amount of diisocyanate would also be changed so it could react with all of the amino and/or hydroxy groups present. As the art skilled will understand, in reactions of this type, a distribution of m values will be obtained (except when m is 0) for individual molecules, and overall, m is the arithmetic average of the values for individual molecules. Fractional values of m are possible by varying the stoichiometry. Experiment 1 illustrates the preparation of such a dicarboxylic acid.

In preferred dicarboxylic acids:
$R^6$ and $R^8$ are each independently 1,4-phenylene, 1,3-phenylene, and n-alkylene containing 2 to 6 carbon atoms;
$R^7$ is 1,4-phenylene, 1,3-phenylene, n-alkylene containing 2 to 6 carbon atoms, or

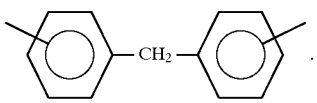

In especially preferred dicarboxylic acids:
$R^6$ and $R^8$ are each independently 1,4-phenylene, 1,3-phenylene, and n-alkylene containing 2 to 6 carbon atoms;
$R^7$ is ethylene, or

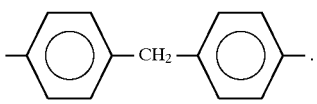

In other preferred dicarboxylic acids E is —$NR^{10}$— wherein $R^{10}$ is hydrogen, or m is an average of 0 to about 3.

By hydrocarbylene in the fourth polymerization and its products is meant a divalent radical containing only carbon and hydrogen. A substituted hydrocarbylene is a radical which also contains substituent groups that do not interfere with any of the reactions, including polymerization, described herein. Suitable functional groups have been listed above.

The polymeric product of the fourth polymerization, particularly one made from dicarboxylic acids containing other functional groups, is useful as a thermoplastic elastomer, urethane rubber or in spandex fiber. The ester groups of the poly(ester-ether) may be hydrolyzed to form polyether diols.

This invention is also concerned with the first depolymerization of a polymer consisting essentially of the repeat unit —[$CHR^1CR^2R^3CR^2R^3CHR^4O$]— wherein $R^1$, $R^2$, $R^3$, and $R^4$ are defined above, and preferred combinations are as given above for the first polymerization process when n=2. A catalyst designated $MZ_3 \cdot Q_t$ is used, wherein M, S, Q, t, and Z, and their preferred embodiments, are as given above for the first polymerization.

The first depolymerization process is carried out at about 100° C. to about 250° C., preferably about 130° to about 200° C. Although air can be used to blanket the process, it is preferred to use an inert atmosphere such as nitrogen to avoid possible side reactions. The polytetrahydrofuran need not be dried before use. A solvent may be used, but it is preferred to carry out the process without solvent.

The amount of catalyst compared to polyether present in the first depolymerization is not critical, 0.1–15% by weight being useful, preferably about 1 to 3% by weight of catalyst.

The first depolymerization process may be carried out by just heating the polyether in the presence of the catalyst. In order to avoid boiling off the often volatile tetrahydrofurans, a pressure vessel may be needed. However, it is preferred to carry out the depolymerization while constantly distilling off the (substituted) tetrahydrofuran as it forms. It is believed that this ensures driving this process to produce the monomeric tetrahydrofuran. The recovered monomeric tetrahydrofuran may be used in the polymerization to form a polytetrahydrofuran.

Both the first polymerization and first depolymerization processes can be done in a variety of ways known to the artisan. The first polymerization can be done by batch, semi-batcj and continuous processes. Continuous processes include continuous stirred tank reactor(s) with one or more stages, and/or plug flow reactors (see Example 19). The first depolymerization process can also be done by similar methods. In this process, a continuous process could be constant addition of polyether to the reactor, while distilling off a similar amount of a monomeric tetrahydrofuran. Other variations will be evident to one skilled in this art.

In both the first polymerization and first depolymerization processes disclosed herein the catalyst may be recovered and reused in either process. It may be recovered from the polymerization process by extracting the polymer formed with water, while it can be recovered from the depolymerization process by extracting the distillation residue with water. In both instances, the recovered catalyst may be used again in a polymerization or depolymerization process. In both instances the aqueous washings may be concentrated by removal of the water (as by evaporation) and the solid catalyst recovered. See Examples 20, and 28–32 for recovery and reuse of catalyst.

The second depolymerization process is carried out at about 100° C. to about 250° C., preferably about 130° C. to about 200° C. Although air can be used to blanket the process, it is preferred to use an inert atmosphere such as nitrogen to avoid possible side reactions. A solvent may be used, but it is preferred to carry out the process without solvent.

The amount of catalyst compared to polyether present is not critical, 0.1–15% by weight (percent of the catalyst to polyether) being useful, preferably about 1 to 3% by weight of catalyst.

The second depolymerization process may be carried out by just heating the polyether in the presence of the heterogeneous catalyst. In order to avoid boiling off the often volatile tetrahydrofurans, a pressure vessel may be needed. However, it is preferred to carry out the depolymerization while constantly distilling off the (substituted) tetrahydrofuran as it forms. It is believed that this ensures driving this process to produce the monomeric tetrahydrofuran.

In both the second and third polymerization and second depolymerization processes disclosed herein heterogeneous catalysts may be recovered and reused in any of the processes. It may be recovered from the processes by filtration, and if desired, drying. The recovered catalyst may be used again in the polymerization or depolymerization processes.

All of the above processes may be carried out as batch, semibatch or continuous processes. For all of the processes, continuous type processes are preferred.

In the Examples, the following abbreviations are used:

ACA—acetic anhydride
DETM—diethyl 2-[3-(triethoxysilyl)propyl)]malonate
DMAC—N,N-dimethylacetamide
GPC—gel permeation chromatography
MDI—bis(4-isocyanatophenyl)methane
Nafion™—a sulfonated perfluoropolymer produced by E. I. du Pont de Nemours and Company, Wilmington, Del., USA
Mn—number average molecular weight
Mw—weight average molecular weight
RB—round bottom
PD—polydispersity (Mw/Mn)
PS—polystyrene
SS—stainless steel
STD—standard
THF—tetrahydrofuran

EXAMPLE 1

Polymerization of THF with Yttrium Triflate and Acetic Anhydride

In a dry box, yttrium triflate (0.75 g) was added to each of three separate oven dried 100 mL RB flasks equipped with stirring bars. The flasks were sealed with rubber septa and removed from the dry box and nitrogen bleeds attached. THF (20 mL) followed by acetic anhydride (0.75 mL) were added to each flask. After 15, 30 and 45 minutes, a polymerization was terminated via the addition of 5% NaOH (10 mL) and THF (50 mL). The resulting organic phases were separated and concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 56.76 | 8180 | 17100 | 2.09 |
| 30 mins. | 67.02 | 6630 | 14600 | 2.20 |
| 45 mins. | 73.11 | 6210 | 13300 | 2.02 |

EXAMPLE 2

Polymerization of THF with Ytterbium Triflate and Acetic Anhydride

In a dry box, ytterbium triflate (0.75 g) was added to each of four separate oven dried 100 mL RB flasks equipped with stirring bars. The flasks were sealed with rubber septa and removed from the dry box. Nitrogen bleeds were attached and THF (20 mL) followed by acetic anhydride (0.75 mL) were added to each flask. After 15, 30, 45 and 60 minutes, a polymerization was terminated via the addition of 5% NaOH (10 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 56.09 | 8400 | 16200 | 1.93 |
| 30 mins. | 67.98 | 7360 | 14900 | 2.03 |
| 45 mins. | 69.67 | 5890 | 13100 | 2.22 |
| 60 mins. | 71.31 | 6010 | 12800 | 2.15 |

EXAMPLE 3

Polymerization of THF with Dysprosium Triflate and Acetic Anhydride

In a dry box, dysprosium triflate (0.75 g) was added to each of four separate oven dried 100 mL RB flasks equipped with stirring bars. The flasks were sealed with rubber septa and removed from the dry box. After the attachment of nitrogen bleeds THF (20 mL) followed by acetic anhydride (0.75 mL) were added to each flask. After 15, 30, 45 and 60 minutes, a polymerization was terminated via the addition of 5% NaOH (10 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 52.03 | 7260 | 15700 | 2.17 |
| 30 mins. | 63.86 | 7220 | 15700 | 2.18 |
| 45 mins. | 70.05 | 6250 | 14300 | 2.30 |
| 60 mins. | 71.36 | 6010 | 13700 | 2.29 |

EXAMPLE 4

Polymerization of THF with Erbium Triflate and Acetic Anhydride

In a dry box, erbium triflate (0.75 g) was added to each of four separate oven dried 100 mL RB flasks equipped with stirring bars. After sealing with rubber septa the flasks were removed from the dry box. Nitrogen bleeds were attached and THF (20 mL) followed by acetic anhydride (0.75 mL) were added to each flask. After 15, 30, 45 and 60 minutes, a polymerization was terminated via the addition of 5% NaOH (10 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 52.82 | 8460 | 15900 | 1.89 |
| 30 mins. | 62.96 | 7390 | 17100 | 2.32 |
| 45 mins. | 66.79 | 8070 | 16400 | 2.04 |
| 60 mins. | 68.20 | 7250 | 16100 | 2.22 |

EXAMPLE 5

Polymerization of THF with Lanthanum Triflate and Acetic Anhydride

In a dry box, lanthanum triflate (0.75 g) was added to each of four separate oven dried 100 mL RB flasks equipped with stirring bars. The flasks were sealed with rubber septa and then removed from the dry box. Nitrogen bleeds were attached and THF (20 mL) and acetic anhydride (0.75 mL) were added to each flask. After 15, 30, 45 and 60 minutes, a polymerization was terminated via the addition of 5% NaOH (10 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 5.60 | 9780 | 13990 | 1.42 |
| 30 mins. | 11.27 | 13700 | 20900 | 1.53 |
| 45 mins. | 40.30 | 17000 | 28100 | 1.65 |
| 60 mins. | 59.24 | 15800 | 33400 | 2.11 |

EXAMPLE 6

Polymerization of THF with Neodymiuum Triflate and Acetic Anhydride

In a dry box, to an oven dried 100 mL RB flask equipped with a stirring bar was added neodymium triflate (0.75 g). The flask was sealed with a rubber septum and removed from the dry box. A nitrogen bleed was attached and THF (20 mL) followed by acetic anhydride (0.75 mL) were added. After 30 minutes the polymerization was terminated via the addition of 5% NaOH (10 mL) and THF (50 mL). The resulting organic phase was separated, concentrated at reduced pressure and then dried under vacuum yielding 7.56 g (42.6%) of polymer. GPC analysis: Mn=8460, Mw=22300, PD=2.65 (PS STD).

EXAMPLE 7

Polymerization of THF with Yttrium Triflate and Acetic Anhydride

In a dry box, yttrium triflate (0.75 g) was added to each of three oven dried 100 mL RB flasks equipped with stirring bars. The flasks were sealed with rubber septa and removed from the dry box. Nitrogen bleeds were attached and THF (20 mL) added to each flasks. Acetic anhydride (0.25, 0.50 and 0.75 mL) was added respectively to each flask. After 60 minutes the polymerizations were quenched via the addition of 5% NaOH (10 mL) and THF (50 mL), the resulting organic phases were separated, concentrated at reduced pressure and then dried in vacuo overnight. Polymer yields and GPC analysis:

| Acetic Anhydride | Polymer Yield (%) | Mn (PS STD) | Mw | PD |
|---|---|---|---|---|
| 0.25 mL | 75.02 | 8080 | 18100 | 2.25 |
| 0.50 mL | 73.33 | 6940 | 14900 | 2.15 |
| 0.75 mL | 75.20 | 5080 | 13600 | 2.68 |

EXAMPLE 8

Polymerization of THF with Yttrium Triflate and Acetic anhydride

In a dry box, to three 100 mL RB flasks equipped with stirring bar were added 0.25, 0.50 and 1.00 g yttrium triflate respectively. The flask were sealed with rubber septa and removed from the dry box. Nitrogen bleeds were attached and THF (20 mL) and acetic anhydride (1.00 mL) were added to each flask. After 60 minutes the polymerizations were terminated via the addition of 5% NaOR (10 mL) and THF (50 mL). The resulting organic phases were separated, concentrated at reduced pressure and dried under vacuum overnight. Polymer yields and GPC analysis:

| Yttrium Triflate | Polymer Yield (%) | Mn (PS STD) | Mw | PD |
|---|---|---|---|---|
| 0.25 g | 50.11 | 11300 | 26200 | 2.02 |
| 0.50 g | 70.79 | 8060 | 17600 | 2.16 |
| 1.00 g | 81.96 | 4820 | 10500 | 2.09 |

EXAMPLE 9

Polymerization of THF with Yttrium Triflate and Acetic Anhydride in Diethyl Ether In a dry box, yttrium triflate (0.75 g) was weighed into an oven dried 100 mL RB flask equipped with addition of 5% NaOR (10 mL) and THF (50 mL). The apparatus sealed with a rubber septum and removed from the dry box. A nitrogen bleed was attached and diethyl ether (20 mL), THF (20 mL) and acetic anhydride (0.75 mL) were added. After 60 minutes the polymerization was quenched via the addition of 5% NaOH (10 mL) and diethyl ether (50 mL). The resulting organic phase was separated, concentrated and dried under vacuum. Yield: 3.86 g (21.76%). GPC analysis: Mn=2960, Mw=7800, PD=2.63 (PS STD).

EXAMPLE 10

Polymerization of THF with Yttrium Triflate and Acetic Anhydride in Toluene

In a dry box, yttrium triflate (0.75 g) was weighed into an oven dried 100 mL RB flask equipped with a stirring bar. After sealing with a rubber septum, removal from the dry box, and attachment of a nitrogen bleed, toluene (20 ml), THF (20 mL) and acetic anhydride (0.75 mL) were added. After 60 minutes the polymerization was terminated via the addition of 5% NaOH (10 ml) and toluene (50 mL). The resulting organic phase was separated, concentrated at reduced pressure and then dried under vacuum. Yield: 1.73 g (9.75%). GPC analysis: Mn=1150, Mw=2700, PD=2.34 (PS STD).

EXAMPLE 11

Copolymerization of THF/3-Methyl-THF with Yttrium Triflate and Acetic Anhydride

In a dry box, yttrium triflate (0.75 g) was added to each of three separate oven dried 100 mL RB flasks equipped with stirring bars. The flasks were sealed with rubber septa and removed from the dry box wherein nitrogen bleeds were attached. THF (15 mL) and 3-methyl-THF (5 mL) followed by acetic anhydride (0.75 ml) were added to each flask. After 15, 30 and 45 minutes, a polymerization was terminated via the addition of 5% NaOH (10 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 39.50 | 6920 | 12400 | 1.80 |
| 30 mins. | 51.63 | 6280 | 13200 | 2.11 |
| 45 mins. | 57.27 | 5860 | 12700 | 2.17 |

$^1$H NMR analysis showed ~12–13% incorporation of 3-methyl-THF in the polymers.

EXAMPLE 12

Polymerization of THF with Yttrium Triflate and Trifluoroacetic Anhydride

In a dry box, yttrium triflate (0.75 g) was weighed in an oven dried 100 mL RB flask equipped with a stirring bar. After sealing with a rubber septum and removal from the dry box and attachment of a nitrogen bleed THF (20 mL) was added followed by trifluoroacetic anhydride (3.00 mL). After 2 hrs. the polymerization was quenched by the addition of 5% NaOH (10 mL) and THF (50 mL). Diethyl ether (50 mL) was added to effect separation of the organic/aqueous phase. The organic phase was separated, concentrated at reduced pressure and then dried under vacuum. Yield: 5.40 g (30.44%). GPC analysis: Mn=53900, Mw=86200, PD=1.78 (PS STD).

EXAMPLE 13

Polymerization of THF with Ytterbium Triflate and Propionic Anhydride

In a dry box, ytterbium triflate (1.00 g) was weighed into an oven dried 100 mL RB flask equipped with a stirring bar. The flask was stoppered with a rubber septum and removed from the dry box and a nitrogen bleed was attached. THF (20 mL) and propionic anhydride (1.00 mL) were added via syringes. After 60 minutes the polymerization was quench with 5% NaOH (10 mL) and THF (50 mL). The resulting organic phase was separated, concentrated at reduced pressure and then dried in vacuo. Yield: 12.69 g (71.5%). GPC analysis: Mn 6520, Mw=14500, PD=2.23.

EXAMPLE 14

Polymerization of 3-Methyl-THF with Yttrium Triflate and Acetic Anhydride

In a dry box, yttrium triflate (0.75 g) was weighed into an oven dried 100 mL RB flask equipped with a stirring bar. The flask was sealed with a rubber septum and removed from the dry box. A nitrogen bleed was attached and 3-methyl-THF (20 mL) was added followed by acetic anhydride (0.75 g). After stirring overnight the polymerization was terminated by the addition of 5% NaOH (10 mL) and THF (25 mL). The resulting organic phase was separated, concentrated at reduced pressure and dried under vacuum. Yield: 6.12 g (34.50%). GPC analysis: Mn=437, Mw=808, PD=1.85.

EXAMPLE 15

Polymerization of THF with Yttrium Triflate and Acetic Anhydride

In a dry box, yttrium triflate (0.75 g) was weighed into an oven dried 100 mL RB flask equipped with a stirring bar. After sealing with a rubber septum the flask was removed from the dry box and a nitrogen bleed attached. THF (20 mL) and acetic anhydride (1.00 mL) were added. After 17.5 hrs. THF (20 mL) and acetic anhydride (1.00 mL) were added to the thick viscous solution. After an additional 2 hrs THF (20 mL) and acetic anhydride were again added to the polymerized solution. The polymerization was terminated 2.5 hrs later via the addition of 5% NaOH (20 mL) and THF (100 mL). The organic phase was separated, concentrated at reduced pressure and dried under vacuum. Polymer yield: 32.3 g (61.23%). GPC analysis: Mn=2490, w=8440, PD=3.39 (PS STD).

EXAMPLE 16

Polymerization of THF with Ytterbium Triflate

In a dry box, ytterbium triflate (1.00 g) was weighed in a 100 mL RB flask equipped with a stirring bar. After sealing with a rubber septum the flask was removed from the dry box and a nitrogen bleed attached. THF (20 mL) was then added via syringe. The polymerization was allowed to proceed overnight and then terminated via the addition of $H_2O$ (25 mL) and diethyl ether (75 mL). The organic phase was separated, concentrated at reduced pressure and then dried under vacuum. Polymer yield: 0.520 g (2.93%). GPC analysis: Mn=416000, Mw=842000, PD=2.02 (PS STD).

EXAMPLE 17

Polymerization of 7-Oxabicyclo[2.2.1]heptane with Ytterbium Triflate and Acetic Anhydride In a dry box, ytterbium triflate (0.5 g) was weighed into a 100 mL RB flask equipped with a stirring bar. After sealing with a rubber septum, the flask was remove from the dry box and a nitrogen bleed attached. 7-oxabicyclo[2.2.1]heptane (10 mL, distilled from potassium carbonate) was added followed by acetic anhydride (0.5 mL). After 1 hr. the polymerization was terminated by the addition of 5% NaOH (10 mL), THF (75 mL) and diethyl ether (~50 mL). The organic phase was separate, concentrated at reduced pressure and then dried under vacuum. Polymer yield: 1.00 g. GPC analysis: Mn=233, Mw=522, PD=2.24 (PS STD).

EXAMPLE 18

Polymerization of Cyclohexene Oxide with Lanthanium Triflate

In a dry box, lanthanum triflate (0.75 g) was weighed in a oven dried 100 mL three neck flask equipped with a stirring bar, reflux condenser and addition funnel. Toluene (20 mL) was added via syringe and cyclohexene oxide (20 mL) was slowly added via the addition funnel. The polymerization was terminated after 2.75 hrs. via the addition of $H_2O$ (10 mL) and toluene (100 mL). The organic phase was separated, concentrated at reduced pressure and then dried under vacuum. Polymer yield: 12.4 g (63.9%). GPC analysis (bimodal distribution): Mn=4510, Mw=25700, PD=5.70 (PS STD).

EXAMPLE 19

Continuous Polymerization of THF with Ytterbium Triflate and Acetic Anhydride

A solution of THF (~500 mL) and ytterbium triflate (25 g) was charged into a 500 mL capacity ISCO pump, which was connected to a 3 way 3.2 mm SS connector ("T" mixer) via 8 cm of 3.2 mm SS tubing containing a check valve. A second ISCO pump (500 mL capacity) was charged with ~100 mL of acetic anhydride and this was connected to the "T" mixer by 75 cm of 3.2 mm SS tubing also containing a check valve. The feed rate of the THF/ytterbium triflate solution was 3.3 mL/min and that of the acetic anhydride was 0.25 mL/min. The "T" mixer was connected to a glass stirred holdup tank (approximately 60 mL volume) by 12 cm of 3.2 mm SS tubing. This tank was then connected to a second stirred holdup tank (approximately 55 mL volume) via Cajon flex tubing with ultra torr fitting (6.4 mm, 13 cm). This in turn was connected to a third glass reactor, plug flow (approximately 60 mL volume), again via Cajon flex tubing with ultra torr fitting (6.4 mm, 13 cm). The polymerized solution exiting from the third reactor was fed to a stirred beaker containing water/diethyl ether. Each reactor was equipped with thermal well port. During the polymerization the temperature in the first reactor stabilized to 41°–42° C. and that of the second reactor to 31°–32° C. and that of the third reactor 26°–27° C. After the contents of the THF/ytterbium triflate pump was discharged, and two fractions of polymer were collected, the pump was again refilled with a solution of THF (~500 mL) and ytterbium triflate (25 g). Three fractions were collected. The last fraction was obtained by purging the system with diethyl ether.

The organic phases were separated, concentrated at reduced pressure and then dried under vacuum giving the following:

| Fraction | Weight |
|---|---|
| 1 | 106.86 g |
| 2 | 79.59 g |
| 3 | 56.97 g |
| 4 | 220.2 g |
| 5 | 97.2 g |

The aqueous phases from above were collected, concentrated at reduced pressure and then dried under vacuum at 180° C. giving a cream solid, 46.98 g, representing a 93.94% recovery of the total ytterbium triflate catalyst used.

EXAMPLE 20

Polymerization of THF with Ytterbium Triflate (Recovered from Example 19) and Acetic Anhydride In a dry box, ytterbium triflate (1.00 g), recovered catalyst from Example 19, was weighed out in a 100 mL RB flask equipped with a stirring bar. A rubber septum was attached and the flask removed from the dry box. A nitrogen bleed was attached and THF (20 mL) added followed by acetic anhydride (1.00 mL). After 1 hr. the polymerization was terminated by the addition of water (25 mL), THF (25 mL) and diethyl ether (50 mL), the resulting organic phase was separated, concentrated at reduced pressure, then dried under vacuum affording 13.42 g (75.65%) of polymer.

EXAMPLE 21

Polymerization of THF with Yttrium Triflate and Acetic Anhydride at −78° C.

In a dry box, yttrium triflate (0.75 g) was weighed in an oven dried 100 mL RB flask equipped with a stirring bar. After sealing with a rubber septum, removal from the dry box and the attachment of a nitrogen bleed, THF (20 mL) was added. The resulting mixture was cooled to −78° C.

Acetic anhydride (0.75 mL) was then added, the polymerization was terminated 5 hrs. later by the addition of water (25 mL) and diethyl ether (50 mL). After warming to room temperature the resulting organic phase was separated, concentrated at reduced pressure, then dried under vacuum affording 0.58 g (3.27%) of polymer.

EXAMPLE 22

Preparation of Didymium (Mischmetall) Triflate

Didymium (mischmetall) oxide (17 g) and water (50 mL) were added to a 200 mL RB flask equipped with stirring bar and an addition funnel and reflux condenser. Triflic acid (50 g) was slowly added via the addition funnel to the resulting stirred slurry. After the addition was completed a homogeneous solution resulted, thus an additional 2.0 g of the oxide was added and the slurry heated to reflux for 2 hrs. The cooled slurry was filtered, the filtrate concentrated at reduced pressure and then dried under vacuum at 150°–210° C. affording 58.4 g of a pink solid.

EXAMPLE 23

Polymerization of THF with Didymium (Mischmetall) Triflate: Polymerization Time on Polymer Yield In a dry box, didymium triflate (0.75 g) was added to each of four separate oven dried 100 mL RB flasks equipped with stirring bars. The flasks were sealed with rubber septa and removed from the dry box and nitrogen bleeds attached. THF (20 mL) followed by acetic anhydride (0.75 mL) were added to each flask. After 15, 30, 45 and 60 minutes, a polymerization was terminated via the addition of 5% NaOH (10 mL) and THF (50 mL). The resulting organic phases were separated, concentrated at reduced pressure and then dried under vacuum. Polymer yields:

| Polymer Time | Polymer Yield (%) |
| --- | --- |
| 15 mins. | 13.92 |
| 30 mins. | 34.94 |
| 45 mins. | 43.74 |
| 60 mins | 49.4 |

EXAMPLE 24

Polymerization of Refluxing THF with Yttrium Triflate and Acetic Anhydride

In a dry box, yttrium triflate (0.75 g) was weighed into an oven dried 100 mL flask equipped with a stirred bar, a reflux condenser was attached, the flask sealed with rubber septum and removed from the dry box and a nitrogen bleed attached. THF (20 mL) was added and the resulting mixture heated to reflux via an oil bath (temp. ~80° C.). Acetic anhydride (0.75 mL) was added to the stirred refluxing mixture. After 30 minutes the polymerization was terminated via the addition of 5% NaOH (10 mL) and THF (50 mL). The cooled organic phase was separated, concentrated at reduced pressure, then dried under vacuum giving 6.44 g (36.30%) of polymer.

EXAMPLE 25

Preparation of Ytterbium Nafion® Salt

In a 300 mL RB flask were added ytterbium oxide (0.75 g) and Nafion® perfluorinated ion exchange resin powder (300 mL, 5 wt. % solution in a mixture of lower aliphatic alcohols and 10% water). The resulting mixture was heated to 100° C. and stirred overnight. The resulting solution was filtered and dried under vacuum at 150° C., affording 9.21 g of a light brown solid.

EXAMPLE 26

Polymerization of THF with Ytterbium Nafion® Salt and Acetic Anhydride

In a dry box, the ytterbium Nafion® salt (1.00 g, from Example 25) was added to each of four oven dried 100 mL RB flasks equipped with stirring bars. The flasks were sealed with rubber septa and removed from the dry box and nitrogen bleeds attached. THF (20 mL) followed by acetic anhydride (1.00 mL) were added to each flask. After 2, 3, 4 and 5 hrs. a polymerization was terminated by the addition of water (25 mL) and diethyl ether (50 mL). The organic phases were separated, concentrated at reduced pressure and then dried under vacuum to give the following:

| Polymer Time | Polymer Yield (%) |
| --- | --- |
| 2 hrs. | 5.24 |
| 3 hrs. | 11.39 |
| 4 hrs. | 17.08 |
| 5 hrs. | 22.66 |

EXAMPLE 27

Depolymerization of PolyTHF with Yttrium Triflate

Polytetrahydrofuran 1000 (300 g, Aldrich) and yttrium triflate (9 g) were placed in a 500 mL three neck flask equipped with a stirring bar, Vigreaux column (30.5 cm) and a fractional distillation head. A nitrogen purge was then attached and all other openings glass stoppered. The resulting mixture was then heated by an oil bath and the water clear distillate fractions collected as follows:

| Fraction | Oil Bath Temp (°C.) | Head Temp (°C.) | Weight |
| --- | --- | --- | --- |
| 1 | 171–175 | 64.5 | 67.49 |
| 2 | 176 | 64.5 | 71.84 |
| 3 | 176 | 64.5 | 32.84 |
| 4 | 178 | 64.5 | 58.67 |
| 5 | 178 | 64.5 | 56.71 |

Total weight of distillate collected: 287.55
$^1$H NMR analyses of all five fractions confirmed the product to be THF.
Yield (Recovery): 95.85%

EXAMPLE 28

Depolymerization of Poly-THF with Yttrium Triflate: Reuse of Catalyst

To the residue remaining from Example 27 was added polytetrahydrofuran 1000 (300 g, Aldrich). The apparatus was reassembled the resulting mixture heated by an oil bath, and the resulting water clear distillate fractions were collected as follows:

| Fraction | Oil Bath Temp (°C.) | Head Temp (°C.) | Weight |
|---|---|---|---|
| 1 | 170–174 | 63–64 | 43.39 |
| 2 | 174 | 64 | 62.68 |
| 3 | 175 | 65 | 66.15 |
| 4 | 177 | 65 | 55.15 |
| 5 | 177 | 65 | 32.58 |

Total weight of distillate collected: 259.95 g
Yield (Recovery): 86.65%
Total time elapsed from start of collection to termination of Example: 2 hrs. 50 mins.

EXAMPLE 29

Polymerization of Recovered THF with Ytterbium Triflate and Acetic Anhydride

In a dry box, ytterbium triflate (1.00 g) was added to an oven dried 100 mL flask equipped with a stirring bar. The flask was then sealed with a rubber septum and removed from the dry box and a nitrogen purge attached. Tetrahydofuran (20 mL) from the fourth fraction of Example 27 was added followed by 1 mL of acetic anhydride. After 1 hour no polymerization was apparent, thus an additional 1 mL of acetic anhydride added. After 1 hour the polymerization was terminated via the addition of 5% NaOH and THF (50 mL), the organic phase separated, concentrated at reduced pressure and then dried in vacuo overnight affording 10.31 g (58%) of polymer. GPC analysis: Mn=1970, Mw=6650, PD=3.38 (PS STD).

EXAMPLE 30

Polymerization of Recovered Purified THF with Ytterbium Triflate and Acetic Anhydride Fractions 2–4 of experiment Example 27 were combined and distilled from sodium/benzophenone. Twenty mL of this dried THF was added to ytterbium triflate (1 g), previously weighed out in an oven dried 100 mL flask equipped with stirring bar and a nitrogen purge. Acetic anhydride (1 mL) was then added, after 1 hour the polymerization was terminated via the addition of 5% NaOH and THF (50 mL), the organic phase separated and concentrated at reduced pressure and then in vacuo, affording 13.32 g (78.08%) of polymer. GPC analysis: Mn=4110, Mw=8860, PD=2.15 (PS STD).

EXAMPLE 31

Recovery of Catalyst from Depolymerization

Water (100 mL) was added to the residue from Example 28, the resulting mixture was stirred at room temperature for approximately 1 hour, the aqueous phase separated and concentrated at reduced pressure and dried in vacuo at 180° C. overnight affording a brown solid. This solid was again dissolved in water, then filtrated, the filtrated concentrated at reduced pressure. The resulting solid was dried under vacuum at 180° C. overnight affording a cream solid: 6.48 g (72%) of recovered catalyst.

EXAMPLE 32

Activity of Recovered Catalyst in the Polymerization of THF

In a dry box, the recovered catalyst of Example 31 (1 g) was placed in an oven dried 100 mL flask equipped with a stirring bar. The flask was sealed with a rubber septum and removed from the dry box and a nitrogen purge attached. THF (20 mL) was then added followed by acetic anhydride (1 mL). After 1 hour the polymerization was terminated via the the addition of 5% NaOH and THF (50 mL), the organic phase separated, concentrated and dried in vacuo overnight affording 13.86 g (78.13%) of polymer. GPC Analysis: Mn=4460, Mw=9280, PD=2.08 (PS STD).

EXAMPLE 33

Depolymerization of Poly-THF/3-Methyl-THF Copolymer with Yttrium Triflate

Poly-tetrahydrofuran/3-methyl-tetrahydrofuran copolymer (308.6 g) containing 3385 ppm water and yttrium triflate (9 g) were placed in a 500 mL three neck flask equipped with a stirring bar, Vigreaux column (30.5 cm), a thermometer and a fractional distillation head. A nitrogen purge was attached and all other opening glass stoppered. The resulting mixture was heated by an oil bath and the water clear distillate fractions collected as follows:

| Fraction | Oil Bath Temp. (°C.) | Rxn. Temp. (°C.) | Head Temp. (°C.) | Weight (g) |
|---|---|---|---|---|
| 1 | 180–182 | 140–145 | 65–70 | 64.35 |
| 2 | 182–184 | 140 | 69–70 | 71.03 |
| 3 | 183–185 | 140–144 | 70 | 69.35 |
| 4 | 185 | 143 | 70 | 70.12 |
| 5 | 185 | — | 70 | 22.35 |

Total Weight Collected: 297.20 g
% Yield (Recovery): 96.47
Total depolymerization time: 2 hrs. 25 mins.

EXAMPLE 34

Depolymerization of PolyTHF, Diacetate Capped, with Yttrium Triflate

Polytetrahydrofuran which was diacetate capped (300 g, Mn 1850) and yttrium triflate (9 g) were placed in a 500 mL three flask equipped with a stirring bar, Vigreaux (30.5 cm), a thermometer and a fractional distillation head. A nitrogen purge was attached and all other openings glass stoppered. The resulting mixture was heated by an oil bath and the water clear distillate fractions collected as follows:

| Fraction | Oil Bath Temp. (°C.) | Rxn. Temp. (°C.) | Head Temp. (°C.) | Weight (g) |
|---|---|---|---|---|
| 1 | 158–160 | 105–129 | 64 | 82.78 |
| 2 | 160–161 | 116–129 | 64–66 | 62.91 |
| 3 | 161 | 116 | 64–67 | 77.71 |
| 4 | 161–180 | — | 67–69 | 51.50 |

Total weight Collected: 274.90 g
% Yield (Recovery): 91.63
Total depolymerization time: 1 hr. 25 mins.

EXAMPLE 35

Polymerization of THF with Bis(n-cyclopentadienyl)tetrahydrofuran-bis (trifluoromethanesulfonato)zirconium and Acetic Anhydride In a dry box, bis(n-cyclopentadienyl)tetrahydrofuran-bis (trifluoromethanesulfonato)zirconium (0.50 g) was added to each of four separate oven dried 100 mL RB flasks equipped with stirring bars. The flasks were sealed with rubber septa and removed from the dry box. After the attachment of nitrogen bleeds THF (10 ML) and acetic anhydride (0.50 mL) were added to each flask. After 15, 30, 45 and 60 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 39.34 | 12700 | 14100 | 1.11 |
| 30 mins. | 54.79 | 15000 | 19000 | 1.27 |
| 45 mins. | 63.92 | 16000 | 22100 | 1.38 |
| 60 mins. | 64.26 | 17200 | 24500 | 1.41 |

EXAMPLE 36

Polymerization of THF with Bis(n-cyclopentadienyl)bis(trifluoromethanesulfonato) titanium and Acetic Anhydride In a dry box, bis(n-cyclopentadienyl)-bis(trifluoromethanesulfonato)titanium (0.50 g) was added to each of four separate oven dried 100 mL RB flasks equipped with stirring bars. The flasks were sealed with rubber septa and then removed from the dry box. Nitrogen bleeds were attached and THF (10 mL) and acetic anhydride (0.50 mL) were added to each flask. After 15, 30, 45, 70 minutes a polymerization was terminated via the addition of water (25 mL), ether (25 mL) and THF (50 mL). The separated organic phases were washed repeatedly with water (3×25 mL), then separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 39.35 | 10700 | 12000 | 1.12 |
| 30 mins. | 61.33 | 13900 | 17300 | 1.25 |
| 45 mins. | 67.08 | 14200 | 19300 | 1.35 |
| 70 mins. | 65.50 | 12400 | 19300 | 1.56 |

EXAMPLE 37

Polymerization of THF with Bis(n-cyclopentadienyl)tetrahydrofuran-bis(trifluoromethanesulfonato)zirconium and Acetyl Chloride In a dry box, bis(n-cyclopentadienyl)tetrahydrofuran-bis(trifluoromethanesulfonato)zirconium (0.50 g) was added to each of three separate oven dried 100 mL RB flasks equipped with stirring bars. The flasks were sealed with rubber septa and removed from the dry box. After the attachment of nitrogen bleeds, THF (10 mL) and acetyl chloride (0.375 mL) were added to each flask. After 15, 30, and 45 minutes, a polymerization was terminated via the addition of water (25 mL), THF (50 mL) and ether (25 mL). The resulting organic phases were washed repeatedly with water (3×25 mL), separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 59.86 | 7980 | 10800 | 1.35 |
| 30 mins. | 68.88 | 7470 | 11000 | 1.48 |
| 45 mins. | 68.65 | 5620 | 9920 | 1.76 |

EXAMPLE 38

Polymerization of THF with Bis(n-cyclopentadienyl)bis(trifluoromethanesulfonato) titanium and Acetyl Chloride In a dry box, bis(n-cyclopentadienyl)-bis(trifluoromethanesulfonato)titanium (0.50 g) was added to each of three separate oven dried 100 mL RB flasks equipped with stirring bars. The flasks were sealed with rubber septa and then removed from the dry box. Nitrogen bleeds were attached and THF (10 mL) and acetyl chloride (0.375 mL) were added to each flask. After 15, 30, and 45 minutes a polymerization was terminated via the addition of water (25 mL), ether (25 mL) and THF (50 mL). The separated organic phases were washed repeatedly with water (3×25 mL), then separated, concentrated at reduced pressure and then dried under vacuum. Polymer yields:

| Polymer. Time | Polymer Yield (%) |
|---|---|
| 15 mins. | 46.11 |
| 30 mins. | 66.85 |
| 45 mins. | 74.97 |

EXAMPLE 39

Polymerization of THF with Bis(n-cyclopentadienyl)tetrahydrofuran-bis (trifluoromethanesulfonato)zirconium and Acetic Anhydride In a dry box, bis(n-cyclopentadienyl)tetrahydrofuran-bis(trifluoromethanesulfonato)zirconium (0.50 g) was added to each of three separate oven dried 100 mL RB flasks equipped with stirring bars. The flasks were sealed with rubber septa and removed from the dry box. After the attachment of nitrogen bleeds THF (20 mL) and acetic anhydride (1.00 mL) were added to each flask. After 15, 30, and 45 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 15.22 | 11300 | 11900 | 1.05 |
| 30 mins. | 30.50 | 18100 | 20300 | 1.12 |
| 45 mins. | 39.35 | 21300 | 25500 | 1.20 |

EXAMPLE 40

Copolymerization of THF and 3-Methyl-THF with Bis(n-cyclopentadienyl)tetrahydrofuran-bis (trifluoromethanesulfonato)zirconium and Acetic Anhydride In a dry box, bis(n-cyclopentadienyl)tetrahydrofuran-bis(trifluoromethanesulfonato)zirconium (0.50 g) was added to each of three separate oven dried 100 mL RB flasks equipped with stirring bars. The flasks were sealed with rubber septa and removed from the dry box. After the attachment of nitrogen bleeds THF (7.5 mL), 3-Methyl-THF (2.5 mL) and acetic anhydride (0.10 mL) were added to each flask. After 15, 30, and 45 minutes, a polymerization was terminated via the addition of water (25 mL), THF (50 mL) and ether (25 mL). The resulting organic phases were separated, concentrated at reduced pressure and then dried under vacuum. $^1$H NMR analysis indicates ~10.5% incorporation of 3-methyl-THF in the polymers. Polymer yields and GPC analysis:

| Polymer. Time | Polymer Yield (%) | Mn (PS STD) | Mw | PD |
| --- | --- | --- | --- | --- |
| 15 mins. | 24.8 | 8500 | 9430 | 1.11 |
| 30 mins. | 41.15 | 11400 | 13300 | 1.17 |
| 45 mins. | 49.15 | 12200 | 15500 | 1.27 |

EXAMPLE 41

Preparation of Bis(n-cyclopentadienyl) tetrahydrofuran-bis(trifluoromethanesulfonato) hafnium In a dry box, hafnocene dichloride (9.93 g) was dissolved in THF (300 mL). To this solution, with stirring, was added a solution of silver triflate (14.12 g) in THF (100 mL). After 10 minutes the precipitated silver chloride was filtered off and the resulting filtrate concentrated to approximately half its volume at reduced pressure. Hexane (250 mL) was added and the resulting mixture placed in the freezer. The resulting precipitate was filtered and then dried under vacuum. Yield: 10.02 g. $^1$H NMR (CDCl$_3$): 6.68 (s, 10 H), 3.76 (m, 4H), 1.84 (m, 4H).

EXAMPLE 42

Preparation of Bis (pentamethyl-n-cyclopentadienyl)bis(trifluoromethanesulfonato) zirconium In a dry box, bis(pentamethylcyclopentadienyl)zirconium dichloride (10.00 g) was dissolved in THF (300 mL). To this solution, with stirring, was added a solution of silver triflate (12.46 g) in THF (100 mL). After 15 minutes the precipitated silver chloride was filtered off and the resulting filtrate concentrated to approximately half its volume at reduced pressure. Hexane (250 mL) was added and the resulting mixture placed in the freezer. The resulting yellow precipitate was filtered and then dried under vacuum. Yield: 6.02 g. $^1$H NMR (CDCl$_3$): 2.12 (s).

EXAMPLE 43

Preparation of Bis(n-cyclopentadienyl)bis (trifluoromethanesulfonato)vanadium

In a dry box, vanadocene dichloride (5.00 g) was dissolved in THF (300 mL). To this solution, with stirring, was added a solution of silver triflate (11.19 g) in THF (100 mL). After 15 minutes the precipitated silver chloride was filtered off and the resulting filtrate concentrated to approximately half its volume at reduced pressure. Hexane (250 mL) was added and the resulting mixture placed in the freezer. The resulting green precipitate was filtered and then dried under vacuum. Yield: 6.99 g.

EXAMPLE 44

Polymerization of THF with bis(n-cyclopentadienyl)tetrahydrofuranbis (trifluoromethanesulfonato)zirconium and Acetic Anhydride in Hexane In a dry box, bis(n-cyclopentadienyl)tetrahydrofuran-bis (trifluoromethanesulfonato)zirconium (0.50 g) was added to each of three separate oven dried 100 mL RB flasks equipped with stirring bars. The flasks were sealed with rubber septa and removed from the dry box. After the attachment of nitrogen bleeds hexane (10 mL), THF (20 mL) and acetic anhydride (0.10 mL) were added to each flask. After 15, 30, and 45 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
| --- | --- | --- | --- | --- |
| 15 mins. | 4.96 | 1390 | 2020 | 1.45 |
| 30 mins. | 9.24 | 2980 | 3470 | 1.16 |
| 45 mins. | 20.40 | 3410 | 4030 | 1.18 |

EXAMPLE 45

Polymerization of Cyclohexene Oxide with bis(n-cyclopentadienyl)tetrahydrofuranbis (trifluoromethanesulfonato)zirconium In a dry box, bis(n-cyclopentadienyl)tetrahydrofuran-bis (trifluoromethanesulfonato)zirconium (0.50 g) was added to an oven dried 100 mL RB flask equipped with stirring bar, reflux condenser and addition funnel. The flask was sealed with a rubber septum and removed from the dry box. After the attachment of a nitrogen bleed, toluene (10 mL) was added. Then a solution of cyclohexene oxide (20 mL) and toluene (10 mL) was slowly added via the addition funnel. After 60 minutes the polymerization was terminated by the addition of water (25 mL) and toluene (100 mL). The separated organic phase was concentrated at reduced pressure and then dried under vacuum. Polymer yield: 2.28 g. GPC analysis (PS STD.): Mn=13600, Mw=24500, PD=1.80.

EXAMPLE 46

Polymerization of THF with Bis n-cyclopentadienyl)tetrahydrofuranbis (trifluoromethanesulfonato)hafnium and Acetic Anhydride In a dry box, bis(n-cyclopentadienyl)tetrahydrofuran-bis (trifluoromethanesulfonato)hafnium (0.50 g) was added to each of four separate oven dried 100 mL RB flasks equipped with stirring bars. The flasks were sealed with rubber septa and removed from the dry box. After the attachment of nitrogen bleeds THF (10 mL) and acetic anhydride (0.50 mL) were added to each flask. After 15, 30, 45 and 60 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 32.13 | 11200 | 12200 | 1.09 |
| 30 mins. | 48.70 | 15200 | 18600 | 1.22 |
| 45 mins. | 58.74 | 17400 | 23100 | 1.33 |
| 60 mins. | 60.54 | 17000 | 24100 | 1.42 |

EXAMPLE 47

Polymerization of THF with Bis(n-cyclopentadienyl)-bis(trifluoromethanesulfonato)vanadium and Acetic Anhydride In a dry box, bis(n-cyclopentadienyl)-bis(trifluoromethanesulfonato)vanadium (0.50 g) was added to each of four separate oven dried 100 mL RB flasks equipped with stirring bars. The flasks were sealed with rubber septa and removed from the dry box. After the attachment of nitrogen bleeds THF (10 mL) and acetic anhydride (0.50 mL) were added to each flask. After 15, 30, 45 and 60 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 17.59 | 10600 | 13000 | 1.22 |
| 30 mins. | 45.32 | 14100 | 18800 | 1.34 |
| 45 mins. | 60.43 | 15100 | 21700 | 1.44 |
| 60 mins. | 62.57 | 10500 | 21000 | 2.00 |

EXAMPLE 48

Polymerization of THF with Bis(Pentamethylcyclopentadienyl)-bis(trifluoromethanesulfonato)zirconium and Acetic Anhydride In a dry box, bis(pentamethylcyclopentadienyl)-bis(trifluoromethanesulfonato)zirconium (0.50 g) was added to each of four separate oven dried 100 mL RB flasks equipped with stirring bars. The flasks were sealed with rubber septa and removed from the dry box. After the attachment of nitrogen bleeds THF (10 mL) and acetic anhydride (0.50 mL) were added to each flask. After 15, 30, 45 and 60 minutes, a polymerization was terminated via the addition of water (25 mL), THF (50 mL) and ether (25 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 33.26 | 10600 | 11900 | 1.12 |
| 30 mins. | 44.64 | 12100 | 14800 | 1.23 |
| 45 mins. | 60.09 | 13400 | 17600 | 1.31 |
| 60 mins. | 70.23 | 15100 | 20900 | 1.38 |

EXAMPLE 49

Polymerization of THF with Bis(pentamethylcyclopentadienyl)bis(trifluoromethanesulfonato)zirconium and Adipoyl Chloride In a dry box, bis(pentamethylcyclopentadienyl)bis(trifluoromethanesulfonato)zirconium (0.50 g) was added to an oven dried 100 mL RB flask equipped with a stirring bar. The flask was sealed with a rubber septum and removed from the dry box. After the attachment of a nitrogen bleed THF (10 mL) and adipoyl chloride (0.50 mL) were added. After 45 minutes, the polymerization was terminated via the addition of water (25 mL), THF (50 mL) and ether (25 mL). The resulting organic phase was separated, concentrated at reduced pressure and then dried under vacuum. Polymer yield: 5.87 g (66.17%).

EXAMPLE 50

Polymerization of THF with Bis(pentamethylcyclopentadienyl-bis(trifluoromethanesulfonato)zirconium and Acetyl Bromide In a dry box, bis(pentamethylcyclopentadienyl)bis(trifluoromethanesulfonato)zirconium (0.50 g) was added to an oven dried 100 mL RB flask equipped with a stirring bar. The flask was sealed with rubber septum and removed from the dry box. After the attachment of a nitrogen bleed THF (10 mL) and acetyl bromide (0.50 mL) were added. After 45 minutes, the polymerization was terminated via the addition of water (25 mL), THF (50 mL) and ether (25 mL). The resulting organic phase was separated, concentrated at reduced pressure and then dried under vacuum. Polymer yield: 2.20 g.

EXAMPLE 51

Polymerization of THF with Bis(n-cyclopentadienyl)-bis(trifluoromethanesulfonato)vanadium and Acetyl Bromide In a dry box, bis(n-cyclopentadienyl)-bis(trifluoromethanesulfonato)vanadium (0.50 g) was added to an oven dried 100 mL RB flask equipped with a stirring bar. The flask was sealed with rubber septum and removed from the dry box. After the attachment of a nitrogen bleed THF (10 mL) and acetyl bromide (0.50 mL) were added. After 60 minutes, the polymerization was terminated via the addition of water (25 mL), THF (50 mL) and ether (25 mL). The resulting organic phase was separated, concentrated at reduced pressure and then dried under vacuum. Polymer yield: 3.68 g.

EXAMPLE 52

Polymerization of THF with Bis(n-cyclopentadienyl)tetrahydrofuran-bis(trifluoromethanesulfonato)hafnium and Acetyl Bromide In a dry box, bis(n-cyclopentadienyl)tetrahydrofuran-bis(trifluoromethanesulfonato)hafnium (0.50 g) was added to an oven dried 100 mL RB flask equipped with a stirring bar. The flask was sealed with a rubber septum and removed from the dry box. After the attachment of a nitrogen bleed THF (10 mL) and acetyl bromide (0.50 mL) were added. After 30 minutes, the polymerization was terminated via the addition of water (25 mL), THF (50 mL) and ether (25 mL). The resulting organic phase was separated, concentrated at reduced pressure and then dried under vacuum. Polymer yield: 2.29 g.

EXAMPLE 53

Polymerization of Oxepane with bis(n-cyclopentadienyl)tetrahydrofuran-bis(trifluoromethanesulfonato)zirconium and Acetic anhydride In a dry box, bis(n-cyclopentadienyl)tetrahydrofuran-bis(trifluoromethanesulfonato)zirconium (0.05 g) was added to an oven dried 50 mL RB flask equipped with stirring bar. The flask was sealed with a rubber septum and removed from the dry box. After the attachment of a nitrogen bleed oxepane (1.00 mL) and acetic anhydride (0.05 mL) were added via syringe. After 60 minutes the polymerization was terminated by the addition of water (10 mL) and ether (25 mL). The separated organic phase was concentrated at reduced pressure and then dried under vacuum. Polymer yield: 0.87 g.

EXAMPLE 54

Polymerization of THF with Bis(n-cyclopentadienyl)tetrahydrofuran-bis(trifluoromethanesulfonato)zirconium and Diglycolyl Chloride In a dry box, bis(n-cyclopentadienyl)tetrahydrofuran-bis(trifluoromethane-sulfonato)zirconium (0.50 g) was added an oven dried 100 mL RB flask equipped with a stirring bar. The flask was sealed with a rubber septum and removed from the dry box. After the attachment of a nitrogen bleed THF (10 mL) and diglycolyl chloride (1.00 mL) were added to the flask. After 45 minutes the polymerization was terminated via the addition of water (25 mL), THF (50 mL) and ether (25 mL). The resulting organic phase was separated, concentrated at reduced pressure and then dried under vacuum. Polymer yield: 0.64 g.

EXAMPLE 55

Copolymerization of THF/3-Methyl-THF with Bis(n-cyclopentadienyl)tetrahydrofuranbis(trifluoromethanesulfonato)zirconium and Diglycolyl Chloride In a dry box, bis(n-cyclopentadienyl)tetrahydrofuran-bis(trifluoromethanesulfonato)zirconium (0.50 g) was added an oven dried 100 mL RB flask equipped with a stirring bar. The flask was sealed with a rubber septum and removed from the dry box. After the attachment of a nitrogen bleed THF (7.5 mL), 3-methyl-THF (2.5 mL) and diglycolyl chloride (1.00 mL) were added to the flask. After 45 minutes the polymerization was terminated via the addition of water (25 mL), THF (50 mL) and ether (25 mL). The resulting organic phase was separated, concentrated at reduced pressure and then dried under vacuum. Polymer yield: 0.63 g.

EXAMPLE 56

Polymerization of THF with Bis(pentamethylcyclopentadienyl)-bis(trifluoromethanesulfonato)zirconium and Trifluoroacetic Anhydride In a dry box, bis(pentamethylcyclopentadienyl)-bis(trifluoromethanesulfonato)zirconium (0.50 g) was added to an oven dried 100 mL RB flask equipped with a stirring bar. The flask was sealed with a rubber septum and removed from the dry box. After the attachment of a nitrogen bleed THF (10 mL) and trifluoroactic anhydride (0.50 mL) were added. After 3 hrs., the polymerization was terminated via the addition of water (25 mL), THF (50 mL) and ether (25 mL). The resulting organic phase was separated, concentrated at reduced pressure and then dried under vacuum. Polymer yield: 4.89 g.

EXAMPLE 57

Copolymerization of THF/3-Methyl-THF with Bis(n-cyclopentadienyl)tetrahydrofuranbis(trifluoromethanesulfonato)zirconium and Adipoyl Chloride In a dry box, bis(n-cyclopentadienyl)tetrahydrofuran-bis(trifluoromethanesulfonato)zirconium (0.50 g) was added an oven dried 100 mL RB flask equipped with a stirring bar. The flask was sealed with a rubber septum and removed from the dry box. After the attachment of a nitrogen bleed THF (7.5 mL), 3-methyl-THF (2.5 mL) and adipoyl chloride (1.00 mL) were added to the flask. After 60 minutes the polymerization was terminated via the addition of water (25 mL), THF (50 mL) and ether (25 mL). The resulting organic phase was separated, concentrated at reduced pressure and then dried under vacuum. Polymer yield: 5.98 g.

EXAMPLE 58

Polymerization of THF with Yttrium Triflate and Acetyl Chloride

In a dry box, yttrium triflate (0.75 g) was added to each of four separate oven dried 100 mL RB flasks equipped with stirring bars. The flasks were sealed with rubber septa and then removed from the dry box.

Nitrogen bleeds were attached and THF (20 mL) and acetyl chloride (0.75 mL) were added to each flask. After 15, 30, 45 and 60 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 49.21 | 1610 | 3470 | 2.15 |
| 30 mins. | 50.05 | 1520 | 3390 | 2.22 |
| 45 mins. | 49.77 | 1510 | 3570 | 2.36 |
| 60 mins. | 52.76 | 1740 | 3940 | 2.26 |

EXAMPLE 59

Polymerization of THF with Ytterbium Triflate and Acetyl Chloride

In a dry box, ytterbium triflate (0.75 g) was added to each of three separate oven dried 100 mL RB flasks equipped with stirring bars. The flasks were sealed with rubber septa and then removed from the dry box.

Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 52.59 | 1710 | 3790 | 2.22 |
| 30 mins. | 52.82 | 1730 | 4540 | 2.61 |
| 45 mins. | 52.25 | 1730 | 4690 | 2.71 |

EXAMPLE 60

Polymerization of THF with Didymium (Mischmetall) Triflate and Acetyl Chloride

In a dry box, didymium triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 21.98 | 1020 | 2000 | 1.95 |
| 30 mins. | 26.94 | 926 | 1780 | 1.92 |
| 45 mins. | 32.86 | 1040 | 2060 | 1.97 |

EXAMPLE 61

Polymerization of THF with Erbium Triflate and Acetyl Chloride

In a dry box, erbium triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 53.83 | 1570 | 3400 | 2.17 |
| 30 mins. | 56.09 | 1650 | 4090 | 2.47 |
| 45 mins. | 56.99 | 1710 | 4310 | 2.51 |

EXAMPLE 62

Polymerization of THF with Scandium Triflate and Acetyl Chloride

In a dry box, scandium triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 53.33 | 1750 | 4180 | 2.38 |
| 30 mins. | 54.17 | 1690 | 4630 | 2.73 |
| 45 mins. | 53.49 | 1570 | 5660 | 3.61 |

EXAMPLE 63

Polymerization of THF with Copper Triflate and Acetyl Chloride

In a dry box, copper triflate (0.75 g) was added to each of three separate oven dried 100 mL RB flasks equipped with stirring bars. The flasks were sealed with rubber septa and then removed from the dry box.

Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 23.56 | 1010 | 2150 | 2.13 |
| 30 mins. | 31.74 | 1250 | 2720 | 2.18 |
| 45 mins. | 43.24 | 1390 | 3180 | 2.29 |

EXAMPLE 64

Polymerization of THF with Tin Triflate and Acetyl Chloride

In a dry box, tin triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields:

| Polymer. Time | Polymer Yield (%) |
|---|---|
| 15 mins. | 23.96 |
| 30 mins. | 40.53 |
| 45 mins. | 41.60 |

EXAMPLE 65

Polymerization of THF with Zirconium Triflate and Acetyl Chloride

In a dry box, zirconium triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 49.04 | 2040 | 4320 | 2.12 |
| 30 mins. | 64.43 | 2200 | 4880 | 2.21 |
| 45 mins. | 65.84 | 2290 | 5190 | 2.27 |

EXAMPLE 66

Polymerization of THF with Zinc Triflate and Acetyl Chloride

In a dry box, zinc triflate (0.75 g) was added to each of three separate oven dried 100 mL RB flasks equipped with stirring bars. The flasks were sealed with rubber septa and then removed from the dry box. Nitrogen bleeds were attached and THF (20 mL) and acetyl chloride (0.75 mL) were added to each flask. After 45, 60 and 75 minutes a polymerization was terminated via the addition of water (25 mL), ether (25 mL) and THF (50 mL). The resulting organic phases were separated, concentrated at reduced pressure and then dried under vacuum. Polymer yields:

| Polymer. Time | Polymer Yield (%) |
|---|---|
| 15 mins. | 5.64 |
| 30 mins. | 6.88 |
| 45 mins. | 7.61 |

EXAMPLE 67

Polymerization of THF with Yttrium Triflate and Adipoyl Chloride

In a dry box, yttrium triflate (1.00 g) was added to each of three separate oven dried 100 mL RB flasks equipped with stirring bars. The flasks were sealed with rubber septa and then removed from the dry box. Nitrogen bleeds were attached and THF (20 mL) and adipoyl chloride (1.00 mL) were added to each flask. After 15, 30 and 45 minutes a polymerization was terminated via the addition of water (25 mL), ether (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 56.20 | 2020 | 4350 | 2.16 |
| 30 mins. | 58.62 | 2350 | 4790 | 2.04 |
| 45 mins. | 58.40 | 1910 | 5250 | 2.75 |

EXAMPLE 68

Polymerization of THF with Terephthaloyl Chloride and Yttrium Triflate

In a dry box, yttrium triflate (0.75 g) and terephthaloyl chloride (2.00 g) were added to a 100 mL RB flask equipped with a stirring bar. The flask was sealed with a rubber septum and removed from the dry box. A nitrogen purge was attached and THF (20 mL) added via syringe. After 90 minutes the polymerization was terminated by the addition of water (25 mL) and THF (25 mL) and ether (50 mL). The separated organic phase was concentrated at reduced pressure and then dried under vacuum. Polymer yield: 2.25 g. GPC Analysis (PS STD.): Mn=40900, Mw=63000, PD=1.54.

EXAMPLE 69

Polymerization of THF with Neodymium Triflate and Acetyl Bromide

In a dry box, neodymium triflate (0.75 g) was added to each of four separate oven dried 100 mL RB flasks equipped with stirring bars. The flasks were sealed with rubber septa and then removed from the dry box. Nitrogen bleeds were attached and THF (20 mL) and acetyl bromide (1.50 mL) were added to each flask. After 15, 30, 45 and 60 minutes a polymerization was terminated via the addition of water (25 mL), ether (25 mL) and THF (50 mL). The resulting organic phases were separated, concentrated at reduced pressure and then dried under vacuum. Polymer yields:

| Polymer. Time | Polymer Yield (%) |
|---|---|
| 15 mins. | 27.11 |
| 30 mins. | 27.06 |
| 45 mins. | 28.13 |
| 60 mins. | 27.28 |

EXAMPLE 70

Polymerization of THF with Diglycolyl Chloride and Ytterbium Triflate

In a dry box, ytterbium triflate (1.00 g) was added to a 100 mL RB flask equipped with a stirring bar. The flask was sealed with a rubber septum and removed from the dry box. A nitrogen purge was attached and THF (20 mL) added via syringe, followed by diglycolyl chloride (2.00 mL, 97%). After 60 minutes the polymerization was terminated by the addition of water (25 mL) and THF (25 mL) and ether (50 mL). The separated organic phase was concentrated at reduced pressure and then dried under vacuum. Polymer yield: 9.53 g.

EXAMPLE 71

Polymerization of THF with Diglycolyl Chloride and Zirconium Triflate

In a dry box, zirconium triflate (1.00 g) was added to a 100 mL RB flask equipped with a stirring bar. The flask was sealed with a rubber septum and removed from the dry box. A nitrogen purge was attached and THF (20 mL) added via syringe, followed by diglycolyl chloride (2.00 mL, 97%). After 60 minutes the polymerization was terminated by the addition of water (25 mL) and THF (25 mL) and ether (50 mL). The separated organic phase was concentrated at reduced pressure and then dried under vacuum. Polymer yield: 7.32 g.

EXAMPLE 72

Copolymerization of THF/3-Methyl-THF with Ytterbium Triflate and Adipoyl Chloride In a dry box, ytterbium triflate (0.50 g) was added an oven dried 100 mL RB flask equipped with a stirring bar. The flask was sealed with a rubber septum and removed from the dry box. After the attachment of a nitrogen bleed THF (7.5 mL), 3-methyl-THF (2.5 mL) and adipoyl chloride (1.00 mL) were added to the flask. After 60 minutes the polymerization was terminated via the addition of water (25 mL), THF (50 mL) and ether (25 mL). The resulting organic phase was separated, concentrated at reduced pressure and then dried under vacuum. Polymer yield: 5.2 g.

EXAMPLE 73

Polymerization of THF with Scandium Triflate and Acetic Anhydride

In a dry box, scandium triflate (0.75 g) was added to each of four separate oven dried 100 mL RB flasks equipped with stirring bars. The flasks were sealed with rubber septa and removed from the dry box. After the attachment of nitrogen bleeds THF (20 mL) and acetic anhydride (0.75 mL) were added to each flask. After 15, 30, 45 and 60 minutes, a polymerization was terminated via the addition of water (25 mL) and THF (50 mL). The resulting organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 15 mins. | 63.64 | 3780 | 11000 | 2.91 |
| 30 mins. | 70.85 | 3270 | 9270 | 2.82 |
| 45 mins. | 70.85 | 2780 | 9740 | 3.49 |
| 60 mins. | 74.18 | 2930 | 8330 | 2.84 |

EXAMPLE 74

Polymerization of THF with Copper Triflate and Acetic Anhydride

In a dry box, copper triflate (0.75 g) was added to each of four separate oven dried 100 mL RB flasks equipped with stirring bars. The flasks were sealed with rubber septa and then removed from the dry box.

Nitrogen bleeds were attached and THF (20 mL) and acetic anhydride (0.75 mL) were added to each flask. After 45, 60, 75 and 90 minutes a polymerization was terminated via the addition of water (25 mL) and THF (50 mL). The separated organic phases were separated, concentrated at reduced pressure and then dried under vacuum. Polymer yields and GPC analysis:

| Polymer. Time | Polymer Yield (%) | Mn (PS STD) | Mw | PD |
|---|---|---|---|---|
| 45 mins. | 23.90 | 10500 | 21100 | 2.01 |
| 60 mins. | 30.10 | 12000 | 23400 | 1.95 |
| 75 mins. | 35.00 | 11400 | 23500 | 2.07 |
| 90 mins. | 53.21 | 13900 | 25900 | 1.86 |

EXAMPLE 75

Polymerization of THF with Zirconium Triflate and Acetic anhydride

In a dry box, zirconium triflate (0.75 g) was added to each of four separate oven dried 100 mL RB flasks equipped with stirring bars. The flasks were sealed with rubber septa and removed from the dry box. Nitrogen bleeds were attached and THF (20 ml) and acetic anhydride (0.75 mL) were added to each flask. After 15, 30, 45 and 60 minutes, a polymerization was terminated via the addition of water (25 mL) and THF (50 mL). The resulting organic phases were separated, concentrated at reduced pressure and then dried under vacuum. Polymer yields:

| Polymer. Time | Polymer Yield (%) |
|---|---|
| 15 mins. | 58.06 |
| 30 mins. | 65.84 |
| 45 mins. | 66.91 |
| 60 mins. | 71.87 |

EXAMPLE 76

Polymerization of THF with Tin Triflate and Acetic Anhydride

In a dry box, tin triflate (0.75 g) was added to each of four separate oven dried 100 mL RB flasks equipped with stirring bars. The flasks were sealed with rubber septa and removed from the dry box. Nitrogen bleeds were attached and THF (20 mL) and acetic anhydride (0.75 mL) were added to each flask. After 15, 30, 45 and 90 minutes, a polymerization was terminated via the addition of water (25 mL) and THF (50 mL). The resulting organic phases were separated, concentrated at reduced pressure and then dried under vacuum. Polymer yields:

| Polymer. Time | Polymer Yield (%) |
|---|---|
| 15 mins. | 24.01 |
| 30 mins. | 44.08 |
| 45 mins. | 54.68 |
| 60 mins. | 58.40 |

EXAMPLE 77

Polymerization of THF with Zinc Triflate and Acetic Anhydride

In a dry box, zinc triflate (0.75 g) was added to an oven dried 100 mL RB flask equipped with a stirring bar. The flask was sealed with a rubber septum and removed from the dry box. A nitrogen bleed was attached and THF (20 mL) and acetic anhydride (0.75 mL) were added. After stirring overnight the polymerization was terminated via the addition of water (25 mL) and THF (50 mL). The resulting organic phase was separated, concentrated at reduced pressure and then dried under vacuum. Polymer Yield: 3.17 g (17.87%).

EXAMPLE 78

Depolymerization of Polytetrahydrofuran with Copper Triflate

Polytetrahydrofuran diol, Mn=~1,000, and copper triflate (9 g) were placed in a 500 mL three neck flask equipped with a stirring bar, Vigreaux column (12") and a fractional distillation head. A nitrogen purge was attached and all other openings were glass stoppered. The resulting mixture was heated by an oil bath and the resulting water clear distillate fractions collected as follow:

| Fraction | Oil Bath Temp (°C.) | Rxn Temp. (°C.) | Head Temp. (°C.) | Weight (g) |
|---|---|---|---|---|
| 1 | 168 | 135–139 | 64 | 47.85 |
| 2 | 168 | 128–135 | 64 | 57.09 |
| 3 | 168 | 118–128 | 66 | 53.67 |
| 4 | 168 | 106–128 | 66 | 57.77 |
| 5 | 168 | 106 | 66 | 76.30 |

Total weight of distillate collected: 292.68 g
% Yield (Recovery): 97.56%
Total depolymerization time from start of collection to termination of experiment: 1 hr. 45 mins.

EXAMPLE 79

Copolymerization of THF/3-Methyl-THF with Zirconium Triflate and Acetic Anhydride In a dry box, zirconium triflate (0.50 g) was added to an oven dried 100 mL RB flask equipped with a stirring bar. The flask was sealed with a rubber septum and removed from the dry box. A nitrogen bleed was attached and THF (7.5 mL) and 3-methyl-THF (2.5 mL) were added followed by acetic anhydride (1.00 mL). After 45 minutes the polymerization was terminated via the addition of water (25 mL) and THF (50 mL). The resulting organic phase was separated, concentrated at reduced pressure and then dried under vacuum. Polymer yield: 5.68 g.

EXAMPLE 80

Copolymerization of THF/3-Methyl-THF with Copper Triflate and Acetic Anhydride

In a dry box, copper triflate (0.50 g) was added to an oven dried 100 mL RB flask equipped with a stirring bar. The flask was sealed with a rubber septum and removed from the dry box. A nitrogen bleed was attached and THF (7.5 mL) and 3-methyl-THF (2.5 mL) were added followed by acetic anhydride (1.00 mL). After 60 minutes the polymerization was terminated via the addition of water (25 mL) and THF (50 mL). The resulting organic phase was separated, concentrated at reduced pressure and then dried under vacuum. Polymer yield: 2.48 g.

EXAMPLE 81

Copolymerization of THF/3-Methyl-THF with Tin Triflate and Acetic Anhydride

In a dry box, tin triflate (0.50 g) was added to an oven dried 100 mL RB flask equipped with a stirring bar. The flask was sealed with a rubber septum and removed from the dry box. A nitrogen bleed was attached and THF (7.5 mL) and 3-methyl-THF (1.6 mL) were added followed by acetic anhydride (1.00 mL). After 60 minutes the polymerization was terminated via the addition of water (25 mL) and THF (50 mL). The resulting organic phase was separated, concentrated at reduced pressure and then dried under vacuum. Polymer yield: 4.42 g.

EXAMPLE 82

Copolymerization of THF/3-Methyl-THF with Scandium Triflate and Acetic Anhydride In a dry box, scandium triflate (0.50 g) was added to an oven dried 100 mL RB flask equipped with a stirring bar. The flask was sealed with a rubber septum and removed from the dry box. A nitrogen bleed was attached and THF (7.5 mL) and 3-methyl-THF (2.5 mL) were added followed by acetic anhydride (1.00 mL). After 45 minutes the polymerization was terminated via the addition of water (25 mL) and THF (50 mL). The resulting organic phase was separated, concentrated at reduced pressure and then dried under vacuum. Polymer yield: 5.81 g.

EXAMPLE 83

Polymerization of THF with Copper Triflate and Trifluoroacetic Anhydride

In a dry box, copper triflate (1.00 g) was added to an oven dried 100 mL RB flask equipped with a stirring bar. The flask was sealed with a rubber septum and removed from the dry box. A nitrogen bleed was attached and THF (20 mL) and trifluoroacetic anhydride (2.00 mL) were added. After stirring for 3 hrs. the polymerization was terminated via the addition of water (25 mL) and THF (50 mL). The resulting organic phase was separated, concentrated at reduced pressure and then dried under vacuum. Polymer Yield: 7.5 g.

EXAMPLE 84

Polymerization of THF with Trifluoroacetic Acid and Ytterbium Triflate at 45° C.

In a dry box, ytterbium triflate (5.00 g) was added to an oven dried 100 mL RB flask equipped with a stirring bar. The flask was sealed with rubber septa and removed from the dry box. After the attachment of nitrogen bleeds THF (20.00 mL) and trifluoroacetic acid (4.00 mL) were added to the flask. Then flask was them immediately placed in an oil bath maintained at 45° C. After 120 minutes the polymerization was terminated via the addition of water (25 mL), THF (50 mL) and ether (25 mL). The resulting organic phase was separated, concentrated at reduced pressure and then dried under vacuum. Polymer yield: 6.61 g. GPC analysis (PS STD.): Mn=5680, Mw=9090, PD=1.60.

EXAMPLE 85

Polymerization of THF with Trifluoroacetic Acid and Ytterbium Triflate at 45° C.

In a dry box, ytterbium triflate (5.00 g) was added to an oven dried 100 mL RB flask equipped with a stirring bar. The flask was sealed with rubber septa and removed from the dry box. After the attachment of a nitrogen bleed THF (20.00 mL) and trifluoroacetic acid (5.00 mL) were added to the flask. The flask was then immediately placed in an oil bath maintained at 45° C. After 120 minutes the polymerization was terminated via the addition of water (25 mL), THF (50 mL) and ether (25 mL). The resulting organic phase was separated, concentrated at reduced pressure and then dried under vacuum. Polymer yield: 3.07 g. GPC analysis (PS STD.): Mn=3290, Mw=4810, PD=1.46.

EXAMPLE 86

Polymerization of THF with Trifluoroacetic Acid and Ytterbium Triflate

In a dry box, ytterbium triflate (2.00, 3.00, 4.00 and 5.00 g) was added to each of four separate oven dried 100 mL RB flasks equipped with stirring bars. The flasks were sealed with rubber septa and removed from the dry box. After the attachment of nitrogen bleeds THF (20.00 mL) and trifluoroacetic acid (2.00 mL) were added to each flask. After 90 minutes the polymerizations were terminated via the addition of water (25 mL), THF (50 mL) and ether (25 mL). The resulting organic phases were separated, concentrated at reduced pressure and then dried under vacuum. Polymer yields and GPC analyses:

| Ytterbium Triflate (g) | Polymer Yield (g) | Mn (PS STD.) | Mw | PD |
| --- | --- | --- | --- | --- |
| 2.00 | 5.32 | 60200 | 95600 | 1.59 |
| 3.00 | 5.95 | 58500 | 89400 | 1.53 |
| 4.00 | 6.70 | 46100 | 76700 | 1.66 |

EXAMPLE 87

Polymerization of THF with Trifluoroacetic Acid and Yttrium Triflate

In a dry box, yttrium triflate (3.00 g) was added to each of three separate oven dried 100 mL RB flasks equipped with stirring bars. The flasks were sealed with rubber septa and removed from the dry box. After the attachment of nitrogen bleeds THF (20.00 mL) and trifluoroacetic acid (5.00 mL) were added to each flask. After 120, 150 and 180 minutes a polymerization was terminated via the addition of water (25 mL), THF (50 mL) and ether (25 mL). The resulting organic phases were separated, concentrated at reduced pressure and the n dried under vacuum. Polymer yields and GPC analyses:

| Polymer. Time | Polymer Yield (g) | Mn (PS STD.) | Mw | PD |
|---|---|---|---|---|
| 120 mins. | 1.57 | 22700 | 32900 | 1.45 |
| 150 mins. | 2.75 | 24600 | 37900 | 1.54 |
| 180 mins. | 3.69 | 30300 | 46400 | 1.54 |

EXAMPLE 88

Polymerization of THF with Trifluoroacetic Acid and Erbium Triflate

In a dry box, erbium triflate (4.00 g) was added to each of five separate oven dried 100 mL RB flasks equipped with stirring bars. The flasks were sealed with rubber septa and removed from the dry box. After the attachment of nitrogen bleeds THF (20.00 mL) and trifluoroacetic acid (5.00 mL) were added to each flask. After 60, 90, 120, 150 and 180 minutes a polymerization was terminated via the addition of water (25 mL), THF (50 mL) and ether (25 mL). The resulting organic phases were separated, concentrated at reduced pressure and then dried under vacuum. Polymer yields and GPC analyses:

| Polymer. Time | Polymer Yield (g) | Mn (PD STD.) | Mw | PD |
|---|---|---|---|---|
| 60 mins. | 2.02 | 13300 | 20900 | 1.57 |
| 90 mins. | 3.13 | 26500 | 36900 | 1.39 |
| 120 mins. | 4.84 | 26600 | 39700 | 1.49 |
| 150 mins. | 5.08 | 30600 | 49600 | 1.62 |
| 180 mins. | 5.58 | 27900 | 45700 | 1.63 |

EXAMPLE 89

Copolymerization of THF/3-Methyl-THF with Trifluoroacetic Acid and Ytterbium Triflate In a dry box, ytterbium triflate (5.00 g) was added to separate oven dried 100 mL RB flasks equipped with stirring bars. The flasks were sealed with rubber septa and removed from the dry box. After the attachment of nitrogen bleeds THF (15.00 mL and 3-methyl-THF (5.00 mL) were added to each flask. Trifluoroacetic acid (3 and 4 mL) was then added to each flask. After 120 minutes the polymerizations were terminated via the addition of water (25 mL), THF (50 mL) and ether (25 mL). The resulting organic phases were separated, concentrated at reduced pressure and then dried under vacuum. Polymer yields and GPC analyses:

| Trifluoroacetic Acid | Polymer Yield (g) | Mn (PS STD.) | Mw | PD |
|---|---|---|---|---|
| 3 mL | 5.37 | 24500 | 37500 | 1.53 |
| 4 mL | 3.9 | 20900 | 30300 | 1.45 |

EXAMPLE 90

Polymerization of THF with Trifluoroacetic Anhydride/Trifluoroacetic Acid and Ytterbium Triflate In a dry box, ytterbium triflate (3.00 g) was added to each of four separate oven dried 100 mL RB flasks equipped with stirring bars. The flasks were sealed with rubber septa and removed from the dry box. After the attachment of nitrogen bleeds THF (20.00 mL) was added to each flask. Trifluoroacetic anhydride and trifluoroacetic acid were added together via syringes in the ratios shown below. After 60 minutes the polymerizations were terminated via the addition of water (25 mL), THF (50 mL) and ether (25 mL). The resulting organic phases were separated, concentrated at reduced pressure and then dried under vacuum. Polymer yields and GPC analyses:

| Trifluoroacetic Anhydride/ Trifluoroacetic Acid (mL) | Polymer Yield (g) | Mn (PS STD.) | Mw | PD |
|---|---|---|---|---|
| 5/2 | 10.66 | 8090 | 13400 | 1.66 |
| 5/3 | 9.21 | 6600 | 10100 | 1.54 |
| 5/4 | 7.13 | 5200 | 8150 | 1.57 |
| 5/5 | 4.86 | 4200 | 59100 | 1.41 |

EXAMPLE 91

Polymerization of THF with Trifluoroacetic Anhydride/Trifluoroacetic Acid and Ytterbium Triflate In a dry box, ytterbium triflate (3.00 g) was added to an oven dried 100 mL RB flask equipped with a stirring bar. The flask was sealed with a rubber septum and removed from the dry box. After the attachment of a nitrogen bleed THF (20.00 mL) was added to the flask. Trifluoroacetic anhydride (3.00 mL) and trifluoroacetic acid (5.00 mL) were added together via syringe. After 60 minutes the polymerization was terminated via the addition of water (25 mL), THF (50 mL) and ether (25 mL). The resulting organic phase was separated, concentrated at reduced pressure and then dried under vacuum. Polymer yield: 6.85 g. GPC analysis: Mn=5910, Mw=9970, PD=1.50 (PS STD.).

EXAMPLE 92

Polymerization of THF with Pentafluoropropionic Acid and Ytterbium Triflate

In a dry box, ytterbium triflate (5.00 g) was added to an oven dried 100 mL RB flask equipped with a stirring bar. The flask was sealed with a rubber septum and removed from the dry box. After the attachment of a nitrogen bleed THF (20.00 mL) and pentafluoropropionic acid (2.00 mL) were added via syringe. After 150 minutes the polymerization was terminated via the addition of water (25 mL), THF (50 mL) and ether (25 ml). The resulting organic phase was separated, concentrated at reduced pressure and then dried under vacuum. Polymer yield: 9.42 g. GPC analysis: Mn=71500, Mw=126000, PD=1.77 (PS STD.).

EXAMPLE 93

Polymerization of THF with Pentafluoropropionic Acid and Ytterbium Triflate

In a dry box, ytterbium triflate (5.00 g) was added to an oven dried 100 mL RB flask equipped with a stirring bar. The flask was sealed with a rubber septum and removed from the dry box. After the attachment of a nitrogen bleed THF (20.00 mL) and pentafluoropropionic acid (5.00 mL) were added via syringe. After 150 minutes the polymerization was terminated via the addition of water (25 mL), THF (50 mL) and ether (25 mL). The resulting organic phase was separated, concentrated at reduced pressure and then dried under vacuum. Polymer yield: 7.00 g. GPC analysis: Mn=20100, Mw=38700, PD=1.92 (PS STD.).

EXAMPLE 94

Polymerization of THF with Cyanoacetic Acid and Ytterbium Triflate

In a dry box, ytterbium triflate (5.00 g) and cyanoacetic acid (5.00 g) were added to an oven dried 100 mL RB flask equipped with a stirring bar. The flask was sealed with a rubber septum and removed from the dry box. After the attachment of a nitrogen bleed THF (20.00 mL) was added via syringe. After 150 minutes the polymerization was terminated via the addition of water (25 mL), THF (50 mL) and ether (25 mL). The resulting organic phase was separated, concentrated at reduced pressure and then dried under vacuum. Polymer yield: 6.15 g. GPC analysis: Mn=22900, Mw=33900, PD=1.48 (PS STD.).

EXAMPLE 95

Polymerization of THF with Trifluoroacetic Acid and Aluminum Triflate

In a dry box, aluminum triflate (1.5 g) was added to an oven dried 100 mL RB flask equipped with a stirring bar. The flask was sealed with a rubber septum and removed from the dry box. After the attachment of a nitrogen bleed THF (10 mL) and trifluoroacetic acid (1.5 mL) were added via syringe. After 120 minutes the polymerization was terminated via the addition of water (25 mL), THF (50 mL) and ether (25 mL). The resulting organic phase was separated, concentrated at reduced pressure and then dried under vacuum. Polymer yield: 4.17 g. GPC analysis: Mn=28500, Mw=52000, PD=1.82 (PS STD.).

EXAMPLE 96

Polymerization of THF with Trifluoroacetic Acid and Zirconium Triflate

In a dry box, zirconium triflate (1.5 g) was added to an oven dried 100 mL RB flask equipped with a stirring bar. The flask was sealed with a rubber septum and removed from the dry box. After the attachment of a nitrogen bleed THF (10 mL) and trifluoroacetic acid (1.5 mL) were added via syringe. After 120 minutes the polymerization was terminated via the addition of water (25 mL), THF (50 mL) and ether (25 mL). The resulting organic phase was separated, concentrated at reduced pressure and then dried under vacuum. Polymer yield: 5.63 g. GPC analysis: Mn=33300, Mw=52600, PD=1.58 (PS STD.).

EXAMPLE 97

Polymerization of THF with Pentafluoropropionic Acid and Aluminum Triflate

In a dry box, aluminum triflate (2.5 g) was added to an oven dried 100 mL RB flask equipped with a stirring bar. The flask was sealed with a rubber septum and removed from the dry box. After the attachment of a nitrogen bleed THF (10.00 mL) and pentafluoropropionic acid (0.90 mL) were added via syringe. After 120 minutes the polymerization was terminated via the addition of water (25 mL), THF (50 mL) and ether (25 mL). The resulting organic phase was separated, concentrated at reduced pressure and then dried under vacuum. Polymer yield: 6.73 g. GPC analysis: Mn=11700, Mw=20600, PD=1.76 (PS STD.).

EXAMPLE 98

Polymerization of THF with Chlorodifluoroacetic Acid and Zirconium Triflate

In a dry box, zirconium triflate (2.5 g) was added to an oven dried 100 mL RB flask equipped with a stirring bar. The flask was sealed with a rubber septum and removed from the dry box. After the attachment of a nitrogen bleed THF (10.00 mL) and chlorodifluoroacetic acid (2.50 mL) were added via syringe. After 120 minutes the polymerization was terminated via the addition of water (25 mL), THF (50 mL) and ether (25 mL). The resulting organic phase was separated, concentrated at reduced pressure and then dried under vacuum. Polymer yield: 5.55 g. GPC analysis: Mn=19600, Mw=35300, PD=1.80 (PS STD.).

EXAMPLE 99

Polymerization of THF with 4-Nitrobenzoic Acid and Aluminum Triflate

In a dry box, aluminum triflate (1.50 g) and 4-nitrobenzoic acid (4.50 g) were added to an oven dried 100 mL RB flask equipped with a stirring bar. The flask was sealed with a rubber septum and removed from the dry box. After the attachment of a nitrogen bleed THF (20.00 mL) was added via syringe. After 30 minutes the polymerization was terminated via the addition of water (25 mL), THF (50 mL) and ether (25 mL). The resulting organic phase was washed with water (2×1000 mL), separated, concentrated at reduced pressure and then dried under vacuum. Polymer yield: 4.43 g. GPC analysis: Mn=37000, Mw=51000, PD=1.38 (PS STD.).

EXAMPLE 100

Polymerization of THF with Trifluoroacetic Acid and Yttrium Triflate

In a dry box, yttrium triflate (3.00 g) was added to an oven dried 100 mL RB flask equipped with a stirring bar. The flask was sealed with a rubber septum and removed from the dry box. After the attachment of a nitrogen bleed THF (20.00 mL) and trifluoroacetic acid (5.00 mL) were added via syringe. After 180 minutes the polymerization was terminated via the addition of water (25 mL), THF (50 mL) and ether (25 mL). The resulting organic phase was separated, concentrated at reduced pressure and then dried under vacuum. Polymer yield: 3.69 g. GPC analysis: Mn=30300, Mw=46400, PD=1.54 (PS STD.).

EXAMPLE 101

Copolymerization of THF/3-Methyl-THF with Trifluoroacetic Acid and Ytterbium Triflate In a dry box, ytterbium triflate (5.00 g) was added to an oven dried 100 mL RB flask equipped with a stirring bar. The flask was sealed with a rubber septum and removed from the dry box. After the attachment of a nitrogen bleed THF (15.00 mL), 3-methyl-THF (5.00 mL) and trifluoroacetic acid (3.00 mL) were added via syringe. After 120 minutes the polymerization was terminated via the addition of water (25 mL), THF (50 mL) and ether (25 mL). The resulting organic phase was separated, concentrated at reduced pressure and then dried under vacuum. Polymer yield: 5.37 g. GPC analysis: Mn=24500, Mw=37500, PD=1.53 (PS STD.).

EXAMPLE 102

Polymerization of THF with Acetic Acid and Ytterbium Triflate

In a dry box, ytterbium triflate (5.00 g) was added to each of four separate oven dried 100 mL RB flasks equipped with stirring bars. The flasks were sealed with rubber septa and removed from the dry box. After the attachment of nitrogen bleeds THF (20.00 mL) and acetic acid (5.00 mL) were added to each flask. After 3, 4, 5 and 24 hours a polymerization was terminated via the addition of water (25 mL), THF (50 mL) and ether (25 mL). The resulting organic phases were separated, washed with water (2×50 mL), concentrated at reduced pressure and then dried under vacuum. Polymer yields and GPC analyses:

| Polymer. Time (Hrs.) | Polymer Yield (g) | Mn (PS STD.) | Mw | PD |
|---|---|---|---|---|
| 3 | 1.15 | 17900 | 34600 | 1.93 |
| 4 | 1.38 | 18400 | 33700 | 1.83 |
| 5 | 1.71 | 16400 | 34000 | 2.07 |
| 24 | 5.29 | 13000 | 30400 | 2.33 |

EXAMPLE 103

Polymerization of THF with Formic Acid (96%) Acid and Ytterbium Triflate

In a dry box, ytterbium triflate (5.00 g) was added to each of six separate oven dried 100 mL RB flasks equipped with stirring bars. The flasks were sealed with rubber septa and removed from the dry box. After the attachment of nitrogen bleeds THF (20.00 mL) and formic acid (96%, 0.75 mL) were added to each flask. After 2, 3, 4, 5, 6 and 24 hours a polymerization was terminated via the addition of water (25 mL), THF (50 mL) and ether (25 mL). The resulting organic phases were separated, washed with water (2×50 mL), concentrated at reduced pressure and then dried under

| Polymer. Time (Hrs.) | Polymer Yield (g) | Mn (PS STD.) | Mw | PD |
|---|---|---|---|---|
| 2 | 1.25 | 14300 | 29500 | 2.06 |
| 3 | 1.65 | 15100 | 30300 | 2.00 |
| 4 | 2.27 | 17600 | 32700 | 1.88 |
| 5 | 2.72 | 16700 | 30800 | 1.85 |
| 6 | 3.29 | 15300 | 29800 | 1.95 |
| 24 | 7.93 | 10700 | 23100 | 2.16 |

EXAMPLE 104

Polymerization of THF with Formic Acid (96%) Acid and Ytterbium Triflate

In a dry box, ytterbium triflate (15.77 g) was added to each of six separate oven dried 100 mL RB flasks equipped with stirring bars. The flasks were sealed with rubber septa and removed from the dry box. After the attachment of nitrogen bleeds THF (20.00 mL) and formic acid (96%, 2.00 mL) were added to each flask. After 3, 4, 5, 6 and 24 hours a polymerization was terminated via the addition of water (25 mL), THF (50 mL) and ether (25 mL). The resulting organic phases were separated, washed with water (2×50 mL), concentrated at reduced pressure and then dried under vacuum. Polymer yields and GPC analyses:

| Polymer. Time (Hrs.) | Polymer Yield (g) | Mn (PS STD.) | Mw | PD |
|---|---|---|---|---|
| 2 | 1.67 | 4350 | 10900 | 2.51 |
| 3 | 2.22 | 5560 | 12000 | 2.16 |
| 4 | 2.83 | 5320 | 12400 | 2.34 |
| 5 | 3.09 | 5460 | 12100 | 2.22 |
| 6 | 3.28 | 5390 | 11700 | 2.19 |
| 24 | 5.82 | 3050 | 7860 | 2.58 |

EXAMPLE 105

Polymerization of THF with Pyruvonitrile and Ytterbium Triflate

In a dry box, ytterbium triflate (3.00 g) was added to a 100 mL round bottom flask equipped with a stirring bar. The flask was sealed with a rubber septum and removed from the dry box. After the attachment of a nitrogen bleed THF (20.00 mL) was added followed by pyruvonitrile (95%, 2.00 mL). After 60 minutes the polymerization was terminated by the addition of water (10 mL), THF (25 mL) and diethyl ether (25 mL). The resulting organic phase was separated, concentrated at reduced pressure and then dried under vacuum. Polymer yield: 1.44 g. GPC analysis: Mn=52700, Mw=67000, PD=1.27 (PS STD.).

EXAMPLE 106

Polymerization of THF with Acetic Acid/Acetic Anhydride and Yttrium Triflate

In a dry box, yttrium triflate (1.00 g) was added to an oven dried 100 mL RB flask equipped with a stirring bar. The flask was sealed with a rubber septum and removed from the dry box. After the attachment of a nitrogen bleed THF (20.00 mL), acetic acid (2.00 mL) and acetic anhydride (2.00 mL) were added via syringe. After 60 minutes the polymerization was terminated via the addition of water (25 mL), THF (50 mL) and ether (25 mL). The resulting organic phase was separated, concentrated at reduced pressure and then dried under vacuum. Polymer yield: 7.32 g. GPC analysis: Mn=2470, Mw=5250, PD=2.13 (PS STD.).

EXAMPLE 107

Polymerization of THF with Trichloroacetic Acid and Aluminum Triflate

In a dry box, aluminum triflate (4.5 g) and trichloroacetic acid (4.5 g) were added to an oven dried 100 mL RB flask equipped with a stirring bar. The flask was sealed with a rubber septum and removed from the dry box. After the attachment of a nitrogen bleed THF (10.00 mL) was added via syringe. After 120 minutes the polymerization was terminated via the addition of water (25 mL), THF (50 mL) and ether (25 mL). The resulting organic phase was washed with water (2×50 mL), separated, concentrated at reduced pressure and then dried under vacuum. Polymer yield: 5.0 g. GPC analysis: Mn=33500, Mw=80100, PD=2.39 (PS STD.).

EXAMPLE 108

Polymerization of THF with 11-Cyano-1-undecanoic Acid and Ytterbium Triflate

In a dry box, ytterbium triflate (10.00 g) and 11-cyano-1-undecanoic acid (5.00 g) were added to an oven dried 100 mL RB flask equipped with a stirring bar. The flask was sealed with a rubber septum and removed from the dry box. After the attachment of a nitrogen bleed THF (20.00 mL)

was added via syringe. After 6 hrs. the polymerization was terminated via the addition of water (25 mL), THF (50 mL) and ether (25 mL). The resulting organic phase was separated, washed with 5% sodium bicarbonate (2×25 mL), concentrated at reduced pressure and then dried under vacuum. Polymer yield: 5.61 g.

EXAMPLE 109

Polymerization of THF with 4-Acetylbutyric Acid and Ytterbium Triflate

In a dry box, ytterbium triflate (10.00 g) was added to an oven dried 100 mL RB flask equipped with a stirring bar. The flask was sealed with a rubber septum and removed from the dry box. After the attachment of a nitrogen bleed THF (20.00 mL) and 4-acetylbutyric (1.00 mL) were added via syringe. After 90 minutes the polymerization was terminated via the addition of water (25 mL), THF (50 mL) and ether (25 mL). The resulting organic phase was separated, washed with 5% sodium bicarbonate (2×25 mL), concentrated at reduced pressure and then dried under vacuum. Polymer yield: 3.25 g.

EXAMPLE 110

Polymerization of THF with Glycolic Acid and Ytterbium Triflate

In a dry box, ytterbium triflate (10.00 g) and glycolic acid (99%, 1.00 g) were added to an oven dried 100 mL RB flask equipped with a stirring bar. The flask was sealed with a rubber septum and removed from the dry box. After the attachment of a nitrogen bleed THF (20.00 mL) was added via syringe. After 90 minutes the polymerization was terminated via the addition of water (25 mL), THF (50 mL) and ether (25 mL). The resulting organic phase was separated, concentrated at reduced pressure and then dried under vacuum. Polymer yield: 4.76 g.

EXAMPLE 111

Preparation of Bismuth Triflate $BiCl_3$ (630 mg, 2 mmol) was slurried in $CH_2Cl_2$ (20 mL). Triflic acid (900 mg, 6 mmol) was added dropwise, and the mixture was stirred overnight at room temperature. The solvent was removed to give 0.9 g of an off white solid. $^{19}F$ NMR (DMSO-$d_6$): δ–77.3.

EXAMPLE 112

Polymerization of THF with Bismuth Triflate and Acetic Anhydride

In a dry box, bismuth triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.71 g. GPC analysis: Mn=8350, Mw=12400, PD=1.49 (PS STD.).

EXAMPLE 113

Preparation of $Zr(OSO_2CF_3)_4 \cdot Zr(OCOCH_3)_4$

Solid $Zr(OTf)_4$ (0.5 g) and $Zr(CF_3CO_2)_4$ (0.5 g) were mixed and THF (25 mL) was added. The mixture was stirred for 15 minutes at room temperature. The solvent was removed and 0.9 g of off white solid was collected. $^{19}F$ NMR (CDCl$_3$): δ–78.3, –76.2 ($Zr(CF_3CO_2)_4$ comes at δ–75.8).

EXAMPLE 114

Polymerization of THF with $Zr(OSO_2CF_3)_4 \cdot Zr(OCOCH_3)_4$ and Acetic Anhydride In a dry box, $Zr(OSO_2CF_3)_4 \cdot Zr(OCOCH_3)_4$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.01 g. GPC analysis: Mn=6900, Mw=10500, PD=1.53 (PS STD.).

EXAMPLE 115

Preparation of Gold Triflate $AuBr_3$ (0.90 g, 2.1 mmol) was slurried in $CH_2Cl_2$ (20 mL) and triflic acid (0.90 g, 6.3 mmol) was added dropwise. The mixture was stirred overnight at room temperature. The solvent was removed and 0.77 g of black solid was collected. $^{19}F$ NMR (DMSO-$d_6$): δ–76.9.

EXAMPLE 116

Polymerization of THF with Gold(III) Triflate and Acetic Anhydride

In a dry box, gold(III) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 6.04 g. GPC analysis: Mn=5240, Mw=9060, PD=1.73 (PS STD.).

EXAMPLE 117

Preparation of $Y(OSO_2CF_3)_2Cl$

Solid $Y(OTf)_3$ (540 mg, 1 mmol) and $YCl_3$ (98 mg, 0.5 mmol) were mixed, and this mixture was poured into stirred THF (30 mL). The mixture became warm as the solid dissolved. The solution was stirred for 15 min, and the THF was removed. $^{19}F$ NMR (DMSO-$d_6$): δ–77.3.

EXAMPLE 118

Polymerization of THF with $Y(OSO_2CF_3)_2Cl$ and Acetic Anhydride

In a dry box, $Y(OSO_2CF_3)_2Cl$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 2.95 g. GPC analysis: Mn=7390, Mw=12800, PD=1.73 (PS STD.).

EXAMPLE 119

Preparation of Y(OSO$_2$CF$_3$)Cl$_2$

Solid Y(OTf)$_3$ (540 mg, 1 mmol) and YCl$_3$ (390 mg, 2 mmol) were mixed, and this mixture was poured into stirred THF (30 mL). The mixture became warm as the solid dissolved. The solution was stirred for 15 min, and the THF was removed. $^{19}$F NMR (DMSO-d$_6$): δ−77.2

EXAMPLE 120

Polymerization of THF with Y(OSO$_2$CF$_3$)Cl$_2$ and Acetic Anhydride

In a dry box, Y(OSO$_2$CF$_3$)Cl$_2$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 0.09 g.

EXAMPLE 121

Preparation of Ta(OSO$_2$CF$_3$)$_4$OCH$_2$CH$_3$

Ta(OEt)$_5$ (813 mg, 2 mmol) was dissolved in CH$_2$Cl$_2$ (20 mL). Triflic acid (1.5 g, 10 mol) was added dropwise and the solution stirred overnight at room temperature. The solvent was removed to produce a colorless oil. $^1$H and $^{19}$F NMR show a mixture of compounds. $^1$H NMR (CDCl$_3$): δ1.85 (t), 1.9 (t), 4.1, (q), 4.15 (broad, q).

EXAMPLE 122

Polymerization of THF with Ta(OSO$_2$CF$_3$)$_4$OCH$_2$CH$_3$ and Acetic Anhydride In a dry box, Ta(OSO$_2$CF$_3$)$_4$OCH$_2$CH$_3$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL), and THF (50 mL). The resulting organic phase was separated, concentrated at reduced pressure and then dried under vacuum. Polymer Yield: 6.29 g. GPC analysis: Mn=2320, Mw=5400, PD=2.33 (PS STD.).

EXAMPLE 123

Preparation of Iron(III) Bis-triflate-acetylacetonate

Fe(acac)$_3$ (1.0 g, 2.8 mmol) was dissolved in CH$_2$Cl$_2$ (15 mL), and triflic acid (850 mg, 5.7 mmol) was added dropwise. The purple solution was stirred overnight at room temperature. The solvent was removed to give a dark oil.

EXAMPLE 124

Polymerization of THF with Iron(III) Bis-Triflate-Acetylacetonate and Acetic Anhydride In a dry box, iron(III) bis-triflate-acetylacetonate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.63 g. GPC analysis: Mn=8330, Mw=16100, PD=1.94 (PS STD.).

EXAMPLE 125

Preparation of Ruthenium(III) Triflate

RuCl$_3$ (1.0 g, 4.6 mmol) was slurried in CH$_2$Cl$_2$ (20 m%) and triflic acid (2.0 g, 13.6 mmol) was added dropwise. The mixture was stirred at room temperature overnight. The solvent was removed and 1.15 g of black solid was collected. $^{19}$F NMR (CDCl$_3$): δ−76.7.

EXAMPLE 126

Polymerization of THF with Ruthenium(III) Triflate and Acetic Anhydride

In a dry box, ruthenium(III) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 30 minutes the polymerization was terminated via the addition of water (25 mL), ether (25 mL) and THF (50 mL). The resulting organic phase was separated, concentrated at reduced pressure and then dried under vacuum. Polymer Yield: 5.25 g. GPC analysis: Mn=7960, Mw=12400, PD=1.56 (PS STD.).

EXAMPLE 127

Preparation of Palladium(II) Triflate

PdCl$_2$ (1.0 g, 5.6 mmol) was slurried in CH$_2$Cl$_2$ (20 mL) and triflic acid (1.7 g, 11.3 mmol) was added dropwise. The mixture was stirred at room temperature overnight. The solvent was removed and 0.9 g of rust color solid was collected. $^{19}$F NMR (CDCl$_3$): δ−78.5.

EXAMPLE 128

Polymerization of THF with Palladium(II) Triflate and Acetic Anhydride

In a dry box, palladium(II) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 0.73 g. GPC analysis: Mn=27100, Mw=32500, PD=1.20 (PS STD.).

EXAMPLE 129

Polymerization of THF with Niobium(V) Triflate and Acetic Anhydride

In a dry box, niobium(V) triflate (0.5 g) was added to an oven dried 100 mL RB flask equipped with a stirring bar.

The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 6.41 g. GPC analysis: Mn=1580, Mw=5810, PD=3.67 (PS STD.).

EXAMPLE 130

Polymerization of THF with Tungsten(VI) Triflate and Acetic Anhydride

In a dry box, tungsten(VI) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 6.12 g. GPC analysis: Mn=4430, Mw=833b, PD=1.88 (PS STD.).

EXAMPLE 131

Preparation of Rhenium(V) Triflate.

$ReCl_5$ (1.0 g, 2.75 mmol) was slurried in $CH_2Cl_2$ (25 mL) and triflic acid (2.1 g, 13.7 mmol) was added dropwise. The mixture was stirred overnight at room temperature. The solvent was removed and 0.9 g of black solid was collected. $^{19}F$ NMR ($CDCl_3$): δ–74.4, –76.3 (small peak).

EXAMPLE 132

Polymerization of THF with Rhenium(V) Triflate and Acetic Anhydride

In a dry box, rhenium(V) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.60 g. GPC analysis: Mn=7170, Mw=13500, PD=1.89 (PS STD.).

EXAMPLE 133

Preparation of Chromium(II) Triflate $CrCl_2$ (0.62 g, 5 mmol) was slurried in $CH_2Cl_2$ (20 mL) and triflic acid (2.3 g, 15 mmol) was added dropwise. The mixture was stirred overnight at room temperature. The solvent was removed and 1.25 g of gray solid was collected. $^{19}F$ NMR ($DMSO-d_6$): δ–76.65, –76.72.

EXAMPLE 134

Polymerization of THF with Chromium(II) Triflate and Acetic Anhydride

In a dry box, chromium(II) triflate (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 4.87 g. GPC analysis: Mn=9210, Mw=18800, PD=2.05 (PS STD.).

EXAMPLE 135

Preparation of n—Cyclopentadienyl-tris (trifluoromethanesulfonato)zirconium $Cp^*ZrCl_3$ (1.0 g, 3 mmol) was slurried in $CH_2Cl_2$ (40 mL). THF (10.00 mL) was added to dissolve the yellow solid. Solid AgOTf (2.3 g, 9 mmol) was added; a white solid formed immediately. The mixture was stirred 15 min, and the orangish solution was filtered. The solvent was removed to produce an orangish oil. The material was crystallized from ether and 1.1 g of yellow solid was collected. $^1H$ NMR showed several peaks around 2 ppm. Coordinated THF is observed by $^1H$ NMR (near δ3.5 and 1.2).

EXAMPLE 136

Polymerization of THF with n-pentamethylcyclopentadienyl-tris-(trifluoromethanesulfonato)zirconium and Acetic Anhydride In a dry box, n-pentamethylcyclopentadienyl-tris (trifluoromethanesulfonato)zirconium (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 6.49 g. GPC analysis: Mn=4350, Mw=7930, PD=1.82 (PS STD.).

EXAMPLE 137

Preparation of Strontium Triflate $SrCl_2$ (790 mg, 5 mmol) was slurried in $CH_2Cl_2$ (20 mL) and triflic acid (1.5 g, 10 mmol) was added dropwise. The mixture was stirred overnight at room temperature. The solvent was removed and 1.7 g of white solid was collected. $^{19}F$ NMR ($DMSO-d_6$): δ–77.4.

EXAMPLE 138

Polymerization of THF with Strontium Triflate and Acetic Anhydride

In a dry box, strontium triflate (0.5 g) was added to an oven dried 100 mL RB flask equipped with a stirring bar. The flask was sealed with a rubber septum and removed from the dry box. A nitrogen bleed was attached and THF (10.00 mL.) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.44 G. GPC analysis: Mn=6630, Mw=11500, PD=1.73 (PS STD.).

EXAMPLE 139

Preparation of Cp$_2$(OTf)Zr—O—Zr(OTf)Cp$_2$

Cp$_2$Zr(Cl)—O—(Cl)ZrCp$_2$ (1.3 g, 2.5 mmol) was dissolved in CH$_2$Cl$_2$ (40 mL), and AgOTf (1.3 g, 5 mmol) was added. The mixture was stirred over a weekend. The mixture was filtered and the solvent was removed. A white solid formed as the solvent evaporated. The mixture was filtered and the solid was washed with Et$_2$O. 1.4 g of white solid was collected. $^1$H NMR (toluene-d$_8$): δ6.0 (s).

EXAMPLE 140

Polymerization of THF with Cp$_2$(OTf)Zr—O—Zr(OTf)Cp$_2$ and Acetic Anhydride

In a dry box, Cp$_2$(OTf)Zr—O—Zr(OTf)Cp$_2$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 1.84 g. GPC analysis: Mn=22600, Mw=28800, PD=1.28 (PS STD.).

EXAMPLE 141

Polymerization of THF with Cp$_2$MeZr(THF)BPh$_4$ and Acetic Anhydride

In a dry box, Cp$_2$MeZr(THF)BPh$_4$ (0.5 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 0.78 g. GPC analysis: Mn=4840, Mw=7390, PD=1.53 (PS STD.).

EXAMPLE 142

Preparation of Bis-(n-Cyclopentadienyl)bis(trifluoromethanesulfonato)molybdenum

Solid Cp$_2$MoCl$_2$ (500 mg, 1.7 mmol) and AgOTf (0.91 g, 3.5 mmol) were mixed and CH$_2$Cl$_2$ (30 mL). The mixture stirred overnight at room temperature. The white solid was filtered off and the solvent was evaporated to give 300 mg of a green solid. $^1$H NMR (CDCl$_3$): δ6.4 (s).

EXAMPLE 143

Polymerization of THF with Bis-(n-Cyclopentadienyl)bis-(trifluoromethanesulfonato)molybdenum and Acetic Anhydride In a dry box, bis-(n-Cyclopentadienyl)-bis-(trifluoromethanesulfonato)molybdenum (0.275 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 0.77 g. GPC analysis: Mn=15000, Mw=21600, PD=1.44 (PS STD.).

EXAMPLE 144

Preparation of Bis(trifluoromethanesulfonato)-bis(acetylacetonate)zirconium

Zr(acac)$_4$ (1.46 g, 3 mmol) was dissolved in CH$_2$Cl$_2$ (5 mL). A solution of triflic acid (0.9 g, 6 mmol) in CH$_2$Cl$_2$ (1 mL) was added to the Zr(acac)$_4$ solution. The solution was stirred 2 hours at room temperature. The solvent was removed and 1.79 g of yellow solid was collected. $^{19}$F NMR (CDCl$_3$): δ−78.4; $^1$H NMR (CDCl$_3$): δ2.15 (s), 5.82 (broad).

EXAMPLE 145

Polymerization of THF with Bis(trifluoromethanesulfonato)-bis(acetylacetonate)zirconium and Acetic Anhydride In a dry box, bis(trifluoromethanesulfonato)bis(acetylacetonate)zirconium (0.50 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 5.27 g. GPC analysis: Mn=13400, Mw=20200, PD=1.51 (PS STD.).

EXAMPLE 146

Preparation of Yttrium Bis(trifluoromethanesulfonato)-2,2,6,6-tetramethyl-3,5-heptanedionate (t-Buacac)$_3$Y (0.64 g, 1 mmol) was dissolved in CH$_2$Cl$_2$ (5 mL). A solution of triflic acid (0.3 g, 2 mmol) in CH$_2$Cl$_2$ (1 mL) was added and the solution was stirred 2 hours at room temperature. The solvent was removed and a white solid was collected. $^1$H NMR (CDCl$_3$): δ1.2, 1.1 (broad s); $^{19}$F NMR (CDCl$_3$): δ−78.4.

EXAMPLE 147

Polymerization of THF with Yttrium Bis(trifluoromethanesulfonato)-2,2,6,6-tetramethyl-3,5-heptanedionate and Acetic Anhydride In a dry box, yttrium bis(trifluoromethanesulfonato)-2,2,6,6-tetramethyl-3,5-heptanedionate (0.50 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 1.26 g. GPC analysis: Mn=17200, Mw=25300, PD=1.47 (PS STD.).

EXAMPLE 148

Preparation of Yttrium Trifluoromethanesulfonato-bis(2,2,6,6-tetramethyl-3,5-heptanedionate)

(t-Buacac)$_3$Y (0.64 g, 1 mmol) was dissolved in CH$_2$Cl$_2$ (5 mL). A solution of triflic acid (0.15 g, 1 mmol) in CH$_2$Cl$_2$ (1 mL) was added dropwise and the solution was stirred 2 h at room temperature. The solvent was removed and a white solid was collected. $^1$H NMR (CDCl$_3$): δ1.15, 1.02; $^{19}$F NMR (CDCl$_3$): δ–78.6 (small, broad), –76.7.

EXAMPLE 149

Polymerization of THF with Yttrium Trifluoromethanesulfonato-bis(2,2,6,6,6-tetramethyl-3,5-heptanedionate) and Acetic Anhydride In a dry box, yttrium trifluoromethanesulfonato-bis(2,2,6,6-tetramethyl-3,5-heptanedionate) (0.50 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 0.18 g.

EXAMPLE 150

Preparation of VO(OTf)$_n$(OCHMe$_2$)$_{3-n}$

V(O)(OnPr)$_3$ (1.2 g, 5 mmol) was dissolved in CH$_2$Cl$_2$ (30 mL). Triflic acid (2.2 g, 15 mmol) was added dropwise to produce a dark red solution. The solvent was removed and a dark oil was produced.

EXAMPLE 151

Polymerization of THF with VO(OTf)$_n$(OCHMe$_2$)$_{3-n}$ and Acetic Anhydride

In a dry box, VO(OTf)$_n$(OCHMe$_2$)$_{3-n}$ (0.50 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 6.07 g. GPC analysis.: Mn=4770, Mw=29110, PD=1.91 (PS STD.).

EXAMPLE 152

Preparation of Silicon Triflate

SiCl$_4$ (3 g, 17.6 mmol) was dissolved in CH$_2$Cl$_2$ (75 mL) and triflic acid (10.6 g, 70.7 mmol) was added dropwise. The mixture was stirred at room temperature over the weekend. The solvent was removed and 4.8 g of brown liquid was collected. $^{19}$F NMR (DMSO-d$_6$): δ–76.4 (intense), small broad peaks at –77.8 and –77.95.

EXAMPLE 153

Polymerization of THF with Silicon Triflate and Acetic Anhydride

In a dry box, silicon triflate (0.50 g) was added to an oven dried 100 mL RB flask equipped with a stirring bar. The flask was sealed with a rubber septum and removed from the dry box. A nitrogen bleed was attached and THF (10.00 mL) and acetic anhydride (1.00 mL) were added. After stirring for 60 minutes the polymerization was terminated via the addition of water (25 mL), ether (25 mL) and THF (50 mL). The resulting organic phase was separated, concentrated at reduced pressure and then dried under vacuum. Polymer Yield: 7.76 g. GPC analysis: Mn=1450, Mw=3170, PD=2.18 (PS STD.).

EXAMPLE 154

Polymerization of 1,3-Dioxolane with Ytterbium Triflate

In a dry box, ytterbium triflate (1.5 g) was added to an oven dried 100 mL RB flask equipped with a stirring bar. The flask was sealed with a rubber septum and removed from the dry box. After the attachment of nitrogen bleeds 1,3-dioxolane (10.00 mL) was added to the flask. After 60 minutes the polymerization was terminated via the addition of water (25 mL), THF (50 mL) and ether (25 mL). The resulting aqueous phase was separated, concentrated at reduced pressure and then dried under vacuum. Yield: 8.89 g (no attempt was made to remove the catalyst from the polymer). GPC analysis (PS STD.): Mn=4170, Mw=8550, PD=2.05.

EXAMPLE 155

Polymerization of 1,3,5-Trioxane with Ytterbium Triflate

In a dry box, ytterbium triflate (1.5 g) was added to an oven dried 100 mL RB flask equipped with a stirring bar. In a separate 100 mL RB flask 1,3,5-trioxane (20.00 g) was added. The flasks were sealed with a rubber septum and removed from the dry box. To the flask containing the trioxane cyclohexane (20 mL) was added, and the resulting mixture heating to 60° C. via an oil bath until an homogeneous solution resulted. This solution (20.00 mL) was then added via syringe to the flask with ytterbium triflate at this temperature. The resulting mixture was then placed in an oil bath maintained at 60° C. After 60 minutes, the polymerization was terminated by the addition of water (25 mL) and ether (25 mL). The resulting solid was separated and dried under vacuum, giving 4.74 g of polymer.

EXAMPLE 156

Heterogeneous 10 wt % Yttrium triflate on alumina catalyst preparation 25 g commercial alumina pellets AL-3945 (3.2 mm diax 3.2 mm) was placed in 250 mL water and the pH adjusted to 3 with acetic acid. After stirring 15 mins the pellets were collected by filtration and suction dried. A solution of 190 mL ethanol and 10 mL water had its apparent pH adjusted to 5 with acetic acid and 5 g of DETM was added. After stirring for 5 minutes the alumina pellets were added and agitated for 30 minutes. The supernatant liquid was then decanted and the pellets washed with 2×25 mL ethanol and suction dried. The solid was dried in flowing nitrogen by heating to 110° C. for 1 hour and then sealed and taken into a nitrogen glove box. 5 g yttrium triflate was dissolved in 50 mL acetonitrile and added to the dry alumina pellets. This slurry was allowed to sit undisturbed overnight in the glove box and then evaporated to dryness in vacuo. The solid was then extracted with 2×25 mL acetonitrile, filtered and washed with acetonitrile. Evaporation of all washings and extracts indicated that ~50% of the original yttrium triflate had been retained on the pellets. The pellets were suction

EXAMPLE 157

Polymerization of THF over 10% Yttrium Triflate on Alumina Pellets with Acetic Anhydride THF was charged into a 500 mL capacity ISCO pump, which was connected to a 3 way 0.3 cm SS connector ("T" mixer) via 8 cm of 0.3 cm SS tubing containing a check valve. A second ISCO pump was charged with acetic anhydride and this was connected to the "T" mixer by 75 cm of 0.3 cm SS tubing also containing a check valve.

In a dry box, all of the catalyst made in Example 1 (23.9 g) was charged into the reactor. This was in turn connected to the "T" mixer by 12 cm of SS tubing. This reactor was then connected to a holdup tank (approximately 60 mL volume) via Cajon flex tubing with ultra torr fitting (0.6 cm, 13 cm. Polymerization was started by first filling the reactor with THF (approximately 83 mL). Then THF was fed at a rate of 0.75 mL/min and acetic anhydride at a rate of 0.075 mL/min. The exiting polymerized solution was fed to a beaker. After each fraction, the pumps were refilled and the collected polymer solution diluted with diethyl ether and washed with water, separated, concentrated at reduced pressure and then dried under vacuum. The following are the conditions under which the various fractions were collected, together with weight of polymer obtained and GPC analysis:

| Fraction | Polymer. Time | THF Flow Rate (mL/min) | ACA Flow Rate (mL/min) | Wt. (g) | Mn (PS STD.) | Mw | PD |
|---|---|---|---|---|---|---|---|
| 1 | 372 mins. | 0.75 | 0.075 | 108.9 | 10800 | 22800 | 2.11 |
| 2 | 899 mins. | 0.50 | 0.05 | 139.2 | 15800 | 36800 | 2.32 |
| 3 | 491 mins. | 0.50 | 0.05 | 17.73 | 27400 | 92300 | 3.37 |
| 4 | 975 mins. | 0.50 | 0.05 | 74.19 | 28400 | 60200 | 2.12 |
| 5 | 464 mins. | 0.50 | 0.95 | 20.6 | | | |
| 6 | 935 mins | 0.50 | 0.05 | 38.25 | | | |

EXAMPLE 158

Heterogeneous 10 wt % Yttrium triflate on silica-alumina catalyst preparation 25 g commercial silica-alumina pellets (Alfa cat #31269; 91% $Al_2O_3$, 6% $SiO_2$) was placed in 250 mL water and the pH adjusted to 3 with acetic acid. The pellets were then treated in a manner identical to that described in Example 156 above.

EXAMPLE 159

Polymerization of THF over 10% Yttrium on Silica-Alumina Pellets with Acetic Anhydride All of the catalyst of Example 158, 10% yttrium triflate on silica-alumina pellets (20.8 g) was charged in the reactor. The apparatus was as described in Example 156. The following are the conditions under which polymer was collected, together with weight of polymer obtained and GPC analysis.

| Fraction | Polymer. Time | THF Flow Rate (mL/min) | ACA Flow Rate (mL/min) | Wt. (g) | Mn (PS STD.) | Mw | PD |
|---|---|---|---|---|---|---|---|
| 1 | 945 mins. | 0.50 | 0.05 | 148.78 | 4370 | 8790 | 2.11 |
| 2 | 466 mins. | 0.50 | 0.05 | 121.3 | 17000 | 33000 | 1.94 |
| 3 | 990 mins. | 0.50 | 0.05 | 177.17 | 24800 | 48900 | 1.97 |
| 4 | 449 mins. | 0.50 | 0.05 | 70.05 | 10000 | 26800 | 2.66 |

EXAMPLE 160

Heterogeneous 10 wt % Zirconium triflate on alumina catalyst preparation.

25 g commercial alumina pellets (Al-3945, 3.2 mm dia.× 3.2 mm)) was placed in 250 mL water and the pH adjusted to 3 with acetic acid. The pellets were then treated in a manner identical to that described in Example 156 above except substituting zirconium triflate for yttrium triflate.

EXAMPLE 161

Polymerization of THF over 10% Zirconium Triflate on Alumina Pellets with Acetic Anhydride All of the catalyst of Example 160, 10% zirconium triflate on alumina pellets (22.74 g), was charged in the reactor. The apparatus was as described in Example 156. The following are the conditions under which polymer was collected, together with weight of polymer obtained.

(dried and then dried in flowing nitrogen at 110° C. for 1 hour before returning to the glove box for collection and storage prior to testing.)

| Fraction | Polymer. Time | THF Flow Rate (mL/min) | ACA Flow Rate (mL/min) | Wt. (g) | Mn (PS STD.) | Mw | PD |
|---|---|---|---|---|---|---|---|
| 1 | 928 mins. | 0.50 | 0.05 | 247.97 | 9010 | 22500 | 2.51 |
| 2 | 498 mins. | 0.50 | 0.05 | 75.00 | 10800 | 32500 | 2.99 |
| 3 | 948 mins. | 0.50 | 0.05 | 164.13 | 29000 | 55800 | 1.92 |
| 4 | 482 mins. | 0.50 | 0.05 | 58.91 | 45000 | 80700 | 1.79 |
| 5 | 896 mins. | 0.50 | 0.05 | 201.15 | 41100 | 80600 | 1.96 |

EXAMPLE 162

Preparation of La loaded zeolite HY for THF polymerization 10 g of zeolite LZY-82 ($NH_4^+$ ion form of zeolite Y) was slurried into 1 liter distilled water and the pH was adjusted to 4 with nitric acid. 1.56 g lanthanum nitrate hexahydrate (calculated to give a final product having ~5 wt % La) was added and the slurry stirred and warmed for 4 hours. The stirring was stopped and the mixture left to sit overnight to complete the exchange. The solid was collected by-filtration and washed with 1 liter distilled water then suction dried. The wet solid was loaded into a horizontal tube furnace and fired as follows in flowing dry air (flow rate 200 mL/min):

Room temperature to 500° C. at 12° C./min.

Hold at 500° C. for 2 hours

Cool to room temperature over 1 hour and collect white powder.

The cool powder was quickly transferred to a tightly capped sample vial in order to minimize exposure to atmospheric moisture. A small portion of the material was sent for x-ray diffraction analysis and showed that the zeolite crystallinity had been maintained during the ion-exchange and calcination procedure and that there was no presence of a bulk $La_2O_3$ phase.

EXAMPLE 163

Polymerization of THF with Lanthanum Zeolite and Acetic Anhydride

In a dry box, the lanthanum zeolite of Example 162 (2.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight the resulting material was diluted with THF (50 mL) and filtered. The resulting filtrate was concentrated at reduced pressure. The vicous liquid was dissolve in THF (50 mL) and dried over anhydrous $NaHCO_3$, filtered concentrated at reduced pressure and then dried under vacuum. Polymer yield: 3.86 g. GPC analysis: Mn=969, Mw=5970, PD=6.17 (PS STD., bimodal distribution).

EXAMPLE 164

Preparation of 5% Y loaded zeolite HY for THF polymerization 10 g of zeolite LZY-82 ($NH_4^+$ ion form of zeolite Y) was slurried into 1 liter distilled water and the pH was adjusted to 4 with nitric acid. 2.20 g yttrium nitrate pentahydrate (calculated to give a final product having ~5 wt % Y) was added and the slurry stirred and warmed for 4 hours. The stirring was stopped and the mixture left to sit overnight to complete the exchange. The solid was collected by filtration and washed with 1 liter distilled water then suction dried. The wet solid was loaded into a horizontal tube furnace and fired as follows in flowing dry air (flow rate 200 mL/min):

Room temperature to 500° C. at 12° C./min.

Hold at 500° C. for 2 hours.

Cool to room temperature over 1 hour and collect white powder.

The cool powder was quickly transferred to a tightly capped sample vial in order to minimize exposure to atmospheric moisture. A small portion of the material was sent for x-ray diffraction analysis and showed that the zeolite crystallinity had been maintained during the ion-exchange and calcination procedure and that there was no presence of a bulk $Y_2O_3$ phase.

EXAMPLE 165

Polymerization of THF with 5% Yttrium Zeolite and Acetic Anhydride

In a dry box, the yttrium zeolite of Example 164 (5.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight ether (50 mL was added to the resulting polymerized solution. After filtering, ether (50 mL) and water (25 mL) were added and the organic phase separated, concentrated at reduced pressure and then dried under vacuum. Polymer yield: 2.21 g. GPC analysis: Mn=840, Mw=4600, PD=5.48 (PS STD., bimodal distribution).

EXAMPLE 166

Polymerization of THF with 5% Yttrium Zeolite HY and Acetic Anhydride

In a dry box, the 5% yttrium zeolite HY of Example 164 (10.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight ether (50 mL) was added to the resulting polymerized solution. After filtering, ether (50 mL) and water (25 mL) were added and the organic phase separated, concentrated at reduced pressure and then dried under vacuum. Polymer yield: 7.29 g. GPC analysis: Mn=1350, Mw=14800, PD=10.94 (PS STD., bimodal distribution).

EXAMPLE 167

Preparation of 10 wt % Y loaded zeolite HY for THF polymerization 50 g of zeolite LZY-82 ($NH_4^+$ ion form of zeolite Y) was slurried into 1 liter distilled water and the pH was adjusted to 4 with nitric acid. 22.0 g yttrium nitrate pentahydrate (calculated to give a final product having ~10 wt % Y) was added and the slurry stirred and warmed for 4 hours. The stirring was stopped and the mixture left to sit overnight to complete the exchange. The solid was collected by filtration and washed with 1 liter distilled water then suction dried. The wet solid was loaded into a horizontal tube furnace and fired as follows in flowing dry air (flow rate 200 mL/min):

Room temperature to 500° C. at 12° C./min.

Hold at 500° C. for 2 hours.

Cool to room temperature over 1 hour and collect white powder.

The cool powder was quickly transferred to a tightly capped sample vial in order to minimize exposure to atmospheric moisture. A small portion of the material was sent for x-ray diffraction analysis and showed that the zeolite crystallinity had been maintained during the ion-exchange and calcination procedure and that there was no presence of a bulk $Y_2O_3$ phase.

EXAMPLE 168

Polymerization of THF with 10 wt % Yttrium Zeolite HY and Acetic Anhydride

In a dry box, the 10% yttrium zeolite HY of Example 167 (10.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After 4 hrs. ether (50 mL) was added to the resulting polymerized solution. After filtering, the organic phase was washed with 5% NaOH (10 mL), separated concentrated at reduced pressure then dried under vacuum. Polymer yield: 6.11 g. GPC analysis: Mn=690, Mw=4120, PD=10.94 (PS STD., bimodal distribution).

EXAMPLE 169

Preparation of Y loaded zeolite mordenite for THF polymerization 10 g of zeolite H-mordenite was slurried into 1 liter distilled water and the pH was adjusted to 4 with nitric acid. 2.20 g yttrium nitrate pentahydrate (calculated to give a final product having ~5 wt % Y) was added and the slurry stirred and warmed for 4 hours. The stirring was stopped and the mixture left to sit overnight to complete the exchange. The solid was collected by filtration and washed with 1 liter distilled water then suction dried. The wet solid was loaded into a horizontal tube furnace and fired as follows in flowing dry air (flow rate 200 mL/min):

Room temperature to 500° C. at 12° C./min.

Hold at 500° C. for 2 hours.

Cool to room temperature over 1 hour and collect white powder.

The cool powder was quickly transferred to a tightly capped sample vial in order to minimize exposure to atmospheric moisture. A small portion of the material was sent for x-ray diffraction analysis and showed that the zeolite crystallinity had been maintained during the ion-exchange and calcination procedure and that there was no presence of a bulk $Y_2O_3$ phase.

EXAMPLE 170

Polymerization of THF with Yttrium Mordenite and Acetic Anhydride

In a dry box, the yttrium mordenite of Example 169 (5.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight ether (50 mL) was added to the resulting polymerized solution. After filtering, ether (50 mL) and water (25 mL) were added and the organic phase separated, concentrated at reduced pressure and then dried under vacuum. Polymer yield: 1.43 g. GPC analysis: Mn=6020, Mw=15500, PD=2.58 (PS STD.).

EXAMPLE 171

Preparation of ~10 wt % Didymium loaded zeolite HY for THF polymerization 50 g of zeolite LZY-82 ($NH_4^+$ ion form of zeolite Y) was slurried into 1 liter distilled water and the pH was adjusted to 4 with nitric acid. 10 g didymium chloride was added and the slurry stirred and warmed for 1 hour. The zeolite was recovered by filtration washed with 1 liter distilled water and then re-slurried into 1 liter fresh distilled water. Another 10 g didymium chloride was added and the pH adjusted to 4 with nitric acid and this slurry was stirred for 1 hour. The stirring was stopped and the mixture left to sit overnight to complete the exchange. The solid was collected by filtration and washed with 1 liter distilled water then suction dried. The wet solid was loaded into a horizontal tube furnace and fired as follows in flowing dry air (flow rate 200 mL/min):

Room temperature to 500° C. at 12° C./min.

Hold at 500° C. for 2 hours.

Cool to room temperature over 1 hour and collect white powder.

The cool powder was quickly transferred to a tightly capped sample vial in order to minimize exposure to atmospheric moisture. The powder was then pressed to 10 tons and the resultant cake sieved through 10–20 mesh to give granulated catalyst.

EXAMPLE 172

Polymerization of THF with 10% Didymium Zeolite HY and Acetic Anhydride

In a dry box, the 10% Didymium zeolite HY of Example 171 (10.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight the polymerized solution was filtered, then ether (25 mL), THF (25 mL) and water (25 mL) were added the organic phase separated concentrated at reduced pressure then dried under vacuum. Polymer yield: 7.56 g. GPC analysis: Mn=1010, Mw=7150, PD=7.08 (PS STD., bimodal distribution).

EXAMPLE 173

Preparation of 5 wt % Sc loaded zeolite HY for THF polymerization 5 g of zeolite LZY-82 ($NH_4^+$ ion form of zeolite Y) was slurried into 1 liter distilled water and the pH was adjusted to 4 with nitric acid. 1.44 g scandium chloride (calculated to give a final product having ~5 wt % Sc) was added and the slurry stirred and warmed for 4 hours. The stirring was stopped and the mixture left to sit overnight to complete the exchange. The solid was collected by filtration and washed with 1 liter distilled water then suction dried. The wet solid was loaded into a horizontal tube Furnace and fired as follows in flowing dry air (flow rate 200 mL/min):

Room temperature to 500° C. at 12° C./min.

Hold at 500° C. for 2 hours.

Cool to room temperature over 1 hour and collect white powder.

The cool powder was quickly transferred to a tightly capped sample vial in order to minimize exposure to atmospheric moisture. A small portion of the material was sent for x-ray diffraction analysis and showed that the zeolite crystallinity had been maintained during the ion-exchange and calcination procedure and that there was no presence of a bulk $Sc_2O_3$ phase.

EXAMPLE 174

Polymerization of THF with 5% Scandium Zeolite HY and Acetic Anhydride

In a dry box, the 5% scandium zeolite HY of Example 173 (3.94 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring overnight the polymerized solution was filtered, then ether (25 mL), THF (25 mL) and water (25 mL) were added the organic phase separated concentrated at reduced pressure then dried under vacuum. Polymer yield: 4.48 g. GPC analysis: Mn=736, Mw=7890, PD=10.72 (PS STD., bimodal distribution).

EXAMPLE 175

Preparation of 10 wt % Y on zeolite NaY pellets 12.5 g yttrium nitrate pentahydrate was dissolved in 1 liter distilled water and the pH adjusted to 4 with nitric acid. 25 g zeolite LZY-52 (NaY) pellets (3 mm dia×3 mm) was added and the mixture allowed to sit overnight. The pellets were then filtered and washed with 1 liter distilled water and suction dried. The pellets were then calcined in flowing dry air (flow rate 200 mL/min):

Room temperature to 500° C. at 12° C./min.

Hold at 500° C. for 2 hours.

Cool to room temperature over 1 hour and collect white powder.

The cool pellets were quickly transferred to a tightly capped sample vial in order to minimize exposure to atmospheric moisture.

EXAMPLE 176

Polymerization of THF with 10% Yttrium Triflate on Zeolite NaY Pellets and Acetic Anhydride In a dry box, the 10% yttrium triflate on zeolite NaY pellets of Example 175 (10.00 g) was added to an oven dried 100 mL round bottom flask equipped with a stirring bar. The flask was sealed with a rubber septum and removed from the dry box. A nitrogen bleed was attached and THF (20.00 mL) and acetic anhydride (1.00 mL) were added. After stirring for 1 hour THF (50 mL) the polymerized solution then filtered. The filtrate was washed with water (25 mL), then ether (50 mL) was added. The organic phase was separated concentrated at reduced pressure then dried under vacuum. Polymer yield: 0.700 g. GPC analysis: Mn=18800, Mw=27100, PD=1.44 (PS STD.).

EXAMPLE 177

Preparation of Yttrium triflate supported on alumina derivatized with diethylmalonate 95 mL ethanol and 5 mL water were mixed and the pH adjusted to 5 with acetic acid. 2 g DETM was added and the mix stirred for 5 minutes. 10 g γ-alumina was added and the slurry stirred further 3 min. The solid was allowed to settle and the supernatant liquid decanted. The recovered solid was then washed with two portions of 25 mL ethanol and suction dried. The solid was finally dried in flowing nitrogen (200 mu/min) by heating to 110° C. and holding at that temperature for 1 hour. The cooled powder was immediately transferred to a nitrogen glove box.

Under a dry nitrogen atmosphere inside a glove box, 0.5 g yttrium triflate was dissolved in 25 mL acetonitrile and 5 g of the alumina powder prepared above was added. The slurry was stirred for 1 hour and then filtered, rinsed with 25 mL acetonitrile and suction dried. The powder was then pumped to dryness in vacuum and stored under nitrogen.

EXAMPLE 178

Polymerization of THF with Yttrium Triflate Supported on Alumina Derivatized with Diethyl Malonate In a dry box, the yttrium triflate supported on diethylmalonate derivatized alumina of Example 177 (5.00 g) was weighed in an oven dried 100 mL RB flask. The flask was sealed with a rubber septum and removed from the dry box. A nitrogen purge was attached and THF (15.00 mL) and acetic anhydride (2.00 mL) added via syringe. After 360 minutes the polymerization was terminated by decanting, followed by concentration at reduced pressure and then drying under vacuum. Polymer yield: 2.53 g. GPC analysis: Mn=8300, Mw=20900, PD=2.52 (PS STD.).

EXAMPLE 179

Preparation of bis(n-cyclopentadienyl) tetrahydrofuran-bis(trifluoromethanesulfonato) zirconium supported on silica derivatized with DETM 95 mL ethanol and 5 mL water were mixed and the pH adjusted to 5 with acetic acid. 2 g DETM was added and the mix stirred for 5 minutes. 10 g silica was added and the slurry stirred a further 3 mins. The solid was allowed to settle and the supernatant liquid decanted. The recovered solid was then washed with two portions of 25 mL ethanol and suction dried. The solid was finally dried in flowing nitrogen (200 mL/min) by heating to 110° C. and holding at that temperature for 1 hour. The cooled powder was immediately transferred to a nitrogen glove box.

Under a dry nitrogen atmosphere inside a glove box, 0.5 g bis(n-cyclopentadienyl)tetrahydrofuran-bis (trifluoromethanesulfonato)zirconium was dissolved in 25 mL acetonitrile and 5 g of the silica powder was added. The slurry was stirred for 1 hour and then filtered, rinsed with 25 mL acetonitrile and suction dried. The powder was then pumped to dryness in vacuum and stored under nitrogen.

EXAMPLE 180

Polymerization of THF with Bis(n-cyclopentadienyl)tetrahydrofuran-bis (trifluoromethanesulfonato)Zirconium Supported on Silica Derivatized with Diethyl Malonate In a dry box, the bis(n-cyclopentadienyl)tetrahydrofuran-bis(trifluoromethane-sulfonato)zirconium supported on silica of Example 179 (5.00 g) was weighed in an oven dried 100 mL RB flask. The flask was sealed with a rubber septum and removed from the dry box. A nitrogen purge was attached and THF (15.00 mL) and acetic anhydride (2.00 mL) were added via syringe. After 360 minutes the polymerization was terminated by decanting, followed by concentration at reduced pressure and then drying under vacuum. Polymer yield: 2.06 g. GPC analysis: Mn=7620, Mw=19000, PD=2.29 (PS STD.).

EXAMPLE 181

Preparation of bis(n-cyclopentadienyl) tetrahydrofuran-bis(trifluoromethanesulfonato) zirconium supported on alumina derivatized with DETM 95 mL ethanol and 5 mL water were mixed and the pH adjusted to 5 with acetic acid. 2 g DETM was added and the mix stirred for 5 minutes. 10 g % λ-alumina was added and the slurry stirred a further 3 mins. The solid was allowed to settle and the supernatant liquid decanted. The recovered solid was then washed with two portions of 25 mL ethanol and suction dried. The solid was finally dried in flowing nitrogen (200 mL/min) by heating to 110° C. and holding at that temperature for 1 hour. The cooled powder was immediately transferred to a nitrogen glove box.

Under a dry nitrogen atmosphere inside a glove box, 0.5 g bis(n-cyclopentadienyl)tetrahydrofuran-bis(trifluoromethanesulfonato)zirconium was dissolved in 25 mL acetonitrile and 5 g of the alumina powder prepared above was added. The slurry was stirred for 1 hour and then filtered, rinsed with 25 mL acetonitrile and suction dried. The powder was then pumped to dryness in vacuum and stored under nitrogen.

EXAMPLE 182

Polymerization of THF with Bis(n-cyclopentdienyl) tetrahydrofuran-bis(trifluoromethanesulfonato) Zirconium Supported on Alumina Derivatized with Diethyl Malonate In a dry box, the bis(n-cyclopentdienyl)tetrahydrofuran-bis(trifluoromethanesulfonato)zirconium supported on alumina of Example 181 (5.00 g) was weighed in an oven dried 100 mL RB flask. The flask was sealed with a rubber septum and removed from the dry box. A nitrogen purge was attached and THF (15.00 mL) and acetic anhydride (2.00 mL) added via syringe. After 360 minutes the polymerization was terminated by decanting, followed by concentration at reduced pressure and then drying under vacuum. Polymer yield: 1.99 g. GPC analysis: Mn=9600, Mw=25800, PD=2.69 (PS STD.).

EXAMPLE 183

Preparation of ~10 wt % Ytterbium triflate supported on silica-alumina 50 g silica-alumina pellets (3.2 mm dia.×3.2 mm) were placed in 250 mL distilled water. The pH was adjusted to 3 with acetic acid and the slurry was stirred for 15 mins. The pellets were collected by filtration and then added to a solution of 190 mL ethanol, 10 mL water in which the pH was adjusted to 5 with acetic acid and then 5 g DETM was added. Stirred for 30 min and then the supernatant liquid was decanted. The pellets were washed with two portions of 25 mL ethanol and then suction dried prior to drying in flowing nitrogen (200 mL/min) at 110° C. for 1 hour. The pellets were then transferred to a nitrogen glove box.

Inside the glove box 10 g ytterbium triflate was dissolved in 100 mL dry acetonitrile and this solution was added to the dry pellets. The slurry then sat overnight under nitrogen before being evaporated to dryness. The recovered solid was washed with three 25 mL portions of dry acetonitrile, suction dried and then dried in flowing nitrogen to 110° C. for 1 hour. The dry pellets were stored under nitrogen in a glove box.

EXAMPLE 184

Depolymerization of Polytetrahydrofuran (Terathane® 1000) with 10% Ytterbium Triflate Supported on Silica-Alumina Polytetrahydrofuran with hydroxyl ends (Terathane® 1000, 300 g, Aldrich) and the 10% ytterbium triflate supported on silica-alumina of Example 183 (10 g) were placed in a 500 mL three neck flask equipped with a stirring bar, Vigreaux column (12") and a fractional distillation head. A nitrogen purge was attached and all other openings were glass stoppered.

The resulting mixture was heated with an oil bath and the resulting water clear distillate fractions collected as follows:

| Fraction | Oil Bath Temp (°C.) | Rxn Temp. (°C.) | Head Temp (°C.) | Weight (g) |
| --- | --- | --- | --- | --- |
| 1 | 180 | 152 | 64 | 70.72 |
| 2 | 198 | 163 | 66 | 112.0 |
| 3 | 196 | 124 | 66 | 59.00 |
| 4 | 202 | 149 | 66 | 55.00 |

Total weight of distillate collected: 296.72 g
% Yield (Recovery): 98.9%
GC analyses of the various fractions confirm the product to be THF

COMPARATIVE EXAMPLE 1

In a dry box, zeolite HY (1.00 g) was added to an oven dry 100 mL RB flask equipped with a stirring bar. The flask was sealed with a rubber septum and removed from the dry box. After the attachment of a nitrogen bleed THF (20.00 mL) was added by syringe. After 45 minutes acetic anhydride (1.00 mL) was added. After filtering off the zeolite catalyst and concentration of the filtrate, no polymer was obtained.

EXAMPLE 185

Polymerization of THF with Ytterbium Triflate and 3-Methyladipic Acid

In a dry box, ytterbium triflate (10.0 g) and 3-methyladipic acid (5.0 g) were added to each of three separate oven dried 100 mL RB flasks equipped with stirring bars. The flasks were sealed with rubber septa and then removed from the dry box. Nitrogen bleeds were attached and THF (20.0 mL) was added to each flask. After 2,4, and 6 hours a polymerization was terminated via the addition of water. (25 mL), ether (25 mL) and THF (50 mL). The resulting organic phases were separated, concentrated at reduced pressure and then dried under vacuum. Polymer yields and GPC analysis:

| Polymerization Time | Polymer Yield (g) | Mn (PS* STD) | Mw | PD |
|---|---|---|---|---|
| 2 hrs. | 2.96 | 8630 | 13800 | 1.61 |
| 4 hrs. | 3.15 | 8170 | 13300 | 1.63 |
| 6 hrs. | 4.79 | 7230 | 12600 | 1.75 |

*Polystyrene standard

EXAMPLE 186

Polymerization of THF with Ytterbium Triflate and Adipic Acid

In a dry box, ytterbium triflate (5.0 g) and adipic acid (1.21 g) were added to an oven dried 100 mL RB flask equipped with a stirring bar. The flask was sealed with rubber septum and then removed from the dry box, a nitrogen bleed was attached and THF (20.0 mL) added. After 60 minutes the polymerization was terminated via the addition of water (25 mL), ether (25 mL) and THF (50 mL). The resulting organic phase was separated, concentrated at reduced pressure and then dried under vacuum. Polymer yield: 7.65 g. GPC analysis (PS STD.): Mn=14000, Mw=39300, PD=2.80, IR analysis (CHCl$_3$, cm$^{-1}$): 2860, 1727 (C=O), 1370, 1100.

EXAMPLE 187

Polymerization of THF with Ytterbium Triflate and Maleic Acid

In a dry box, ytterbium triflate (5.0 g) and maleic acid (1.9 g) were added to an oven dried 100 mL RB flask equipped with a stirring bar. The flask was sealed with rubber septum and then removed from the dry box, a nitrogen bleed was attached and THF (20.0 mL) added. After 60 minutes the polymerization was terminated via the addition of water (25 mL), ether (25 mL) and THF (50 mL). The resulting organic phase was separated, concentrated at reduced pressure and then dried under vacuum. Polymer yield: 3.98 g. GPC analysis (PS STD): Mn=8950, Mw=16800, PD=1.88.

EXAMPLE 188

Polymerization of THF with Ytterbium Triflate and Isophthalic Acid

In a dry box, ytterbium triflate (5.0 g) and isophthalic acid (2.76 g) were added to an oven dried 100 mL RB flask equipped with a stirring bar. The flask was sealed with rubber septum and then removed from the dry box, a nitrogen bleed was attached and THF (20.0 mL) added. After 60 minutes the polymerization was terminated via the addition of water. The polymer was dissolved in methylene chloride. The resulting organic solution was washed with water (2×200 mL), then concentrated at reduced pressure and then dried under vacuum. Polymer yield: 12.24 g. GPC analysis (PS STD): Mn=258000, Mw=559000, PD=2.16.

EXAMPLE 189

Polymerization of THF with Ytterbium Triflate and Terephthalic Acid

In a dry box, ytterbium triflate (5.0 g) and terephthalic acid (2.76 g) were added to an oven dried 100 mL RB flask equipped with a stirring bar. The flask was sealed with rubber septum and then removed from the dry box, a nitrogen bleed was attached and THF (20.0 mL) was added. After 60 minutes the polymerization was terminated via the addition of water. The polymer was dissolved in methylene chloride. The resulting organic solution was washed with water (2×200 mL), then concentrated at reduced pressure and then dried under vacuum. Polymer yield: 3.66 g. GPC analysis (PS STD): Mn=308000, Mw=744000, PD=2.42.

EXAMPLE 190

Polymerization of THF with Ytterbium Triflate and A

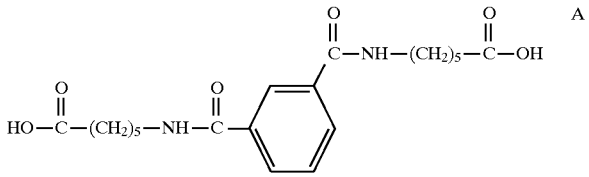

In a dry box, ytterbium triflate (5.0 g) and A (1.5 g) were added to an oven dried 100 mL RB flask equipped with a stirring bar. The flask was sealed with rubber septum and then removed from the dry box, a nitrogen bleed was attached and THF (20.0 mL) added. After 120 minutes the polymerization was terminated via the addition of water, THF and ether. The resulting separated organic solution was washed with sodium bicarbonate (2×25 mL), then concentrated at reduced pressure and dried under vacuum. Polymer yield: 2.37 g.

EXAMPLE 191

Polymerization of THF with Ytterbium Triflate and A

In a dry box, ytterbium triflate (5.0 g) and A (0.5 g) were added to an oven dried 100 mL RB flask equipped with a stirring bar. The flask was sealed with rubber septum and then removed from the dry box, a nitrogen bleed was attached and THF (20.0 mL) was added. After 60 minutes the polymerization was terminated via the addition of water, THF and ether. The resulting separated organic solution was washed with sodium bicarbonate (2×25 mL), then concentrated at reduced pressure and then dried under vacuum. Polymer yield: 1.97 g. GPC analysis (PS STD): Mn=72200, Mw=173000, PD=2.39.

EXAMPLE 192

Polymerization of THF with Ytterbium Triflate and B

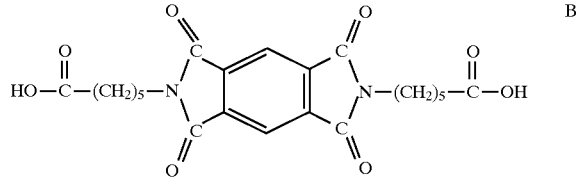

In a dry box, ytterbium triflate (5.0 g) and B (1.5 g) were added to an oven dried 100 mL RB flask equipped with a stirring bar. The flask was sealed with rubber septum and then removed from the dry box, a nitrogen bleed was attached and THF (20.0 mL) added. After 120 minutes the polymerization was terminated via the addition of water, THF and ether. The resulting separated organic solution was washed with sodium bicarbonate (2×25 mL), then concentrated at reduced pressure and then dried under vacuum. Polymer yield: 8.49 g. GPC analysis (PS STD): Mn=127000, Mw=341000, PD=2.67.

EXAMPLE 193

Polymerization of THF with Ytterbium Triflate and 1,2,4-Benzenetricarboxylic Acid In a dry box, ytterbium triflate (5.0 g) and 1,2,4-benzenetricarboxylic acid (2.0 g) were added to an oven dried 100 mL RB flask equipped with a stirring bar. The flask was sealed with rubber septum and then removed from the dry box, a nitrogen bleed was attached and THF (20.0 mL) added. After 21 hours the polymerization was terminated via the addition of water, THF and ether. The resulting separated organic solution was washed with sodium bicarbonate (25 mL) upon which a gelatinous material resulted. HCl was then added and the organic phase separated, then concentrated at reduced pressure and finally dried under vacuum. Polymer yield: 8.91 g. GPC analysis (PS STD): Mn=100000, Mw=227000, PD=2.26.

EXAMPLE 194

Polymerization of THF with Ytterbium Triflate and 1,1'-Ethylenebis(5-oxo-3-pyrrolidecarboxylic Acid)

In a dry box, ytterbium triflate (5.0 g) and 1,1'-ethylenebis (5-oxo-3-pyrrolidecarboxylic acid) (1.0 g) were added to an oven dried 100 mL RB flask equipped with a stirring bar. The flask was sealed with rubber septum and then removed from the dry box, a nitrogen bleed was attached and THF (20.0 mL) added. After 3 hours the polymerization was terminated via the addition of water, THF and ether. The resulting separated organic solution was washed with sodium bicarbonate then the organic phase separated, concentrated at reduced pressure and finally dried under vacuum. Polymer yield: 5.21 g. GPC analysis (PS STD): Mn=73200, Mw=194000, PD=2.65.

EXAMPLE 195

Polymerization of THF with Ytterbium Triflate and Isophthalic Acid and Terephthalic Acid In a dry box, ytterbium triflate (5.0 g), terephthalic acid (2.00 g) and isophthalic acid (0.5 g) were added to an oven dried 100 mL RB flask equipped with a stirring bar. The flask was sealed with rubber septum and then removed from the dry box, a nitrogen bleed was attached and THF (20.0 mL) added. After stirring overnight the polymerization was terminated via the addition of water. The polymer was dissolved in methylene chloride. The resulting organic solution was washed with water (2×200 mL), then concentrated at reduced pressure and then dried under vacuum. Polymer yield: 7.38 g. GPC analysis (PS STD): Mn=42000, Mw=138000, PD=3.30.

EXAMPLE 196

Polymerization of THF with Ytterbium Triflate and N-Acetyl-L-glutamic Acid

In a dry box, ytterbium triflate (15.0 g) and N-acetyl-L-glutamic acid (1.0 g) were added to an oven dried 100 mL RB flask equipped with a stirring bar. The flask was sealed with rubber septum and then removed from the dry box, a nitrogen bleed was attached and THF (20.0 mL) added. After stirring overnight the polymerization was terminated via the addition of water, THF and ether. The resulting organic solution was washed with water, then concentrated at reduced pressure and then dried under vacuum. Polymer yield: 2.82 g. GPC analysis (PS STD): Mn=16600, Mw=80500, PD=4.83.

EXPERIMENT 1

Preparation of (HOCOPh—NHC(O)NH—Ph)$_2$—CH$_2$

In a dry box, MDI (25.0 g) was weighed into a 500 mL RB flask equipped with a stirrer, dimethylacetamide (DMAC, 75 mL) was then added. A solution of 4-aminobenzoic acid (27.8 g) in DMAC (25 mL) was slowly added to the stirred MDI/DMAC solution. The reaction was allowed to stir overnight, then the reaction mixture was poured into diethyl ether. The resulting precipitate was filtered and dried under vacuum at 100° C. In this compound all phenyl rings are para substituted.

EXAMPLE 197

Polymerization of THF with (HO$_2$CPh—NHC(O)NH—Ph)$_2$—CH$_2$ and Ytterbium Triflate In a dry box, ytterbium triflate (5.00 g) and (HO$_2$CPh—NHC(O)NH—Ph)$_2$—CH$_2$ (1.0 g) were added to an oven dried 100 mL RB flask equipped with a stirring bar. The flask was sealed with a rubber septum and removed from the dry box. After the attachment of a nitrogen bleed THF (20.00 mL) was added via syringe. After 18 hrs. the resulting solid mass was dissolved in THF (~800 mL) and water (~10 mL). The resulting mixture was filtered through Celite and then concentrated at reduced pressure to ~200 mL, then poured into a Waring blender containing water (~500 mL). The resulting precipitated polymer was recovered via filtration and dried under vacuum affording 10.30 g of white material.

EXAMPLE 198

Polymerization of THF/3-Me-THF with (HO$_2$CPh—NHC(O)NH—Ph)$_2$—CH$_2$ and Ytterbium Triflate In a dry box, ytterbium triflate (5.00 g) and (HO$_2$CPh—NHC(O)NH—Ph)$_2$—CH$_2$ (1.0 g) were added to an oven dried 100 mL RB flask equipped with a stirring bar. The flask was sealed with a rubber septum and removed from the dry box. After the attachment of a nitrogen bleed THF (15.00 mL) and 3-Me-THF (5.0 mL) were added via syringe. After 18 hrs. the resulting solid mass was dissolved in THF (~800 mL) and water (~10 mL). The resulting mixture was filtered through Celite and then concentrated at reduced pressure to ~200 mL, then poured into a Waring blender containing water (~500 mL). The resulting precipitated polymer was recovered via filtration and dried under vacuum affording 7.38 g of white material.

EXPERIMENT 2

Preparation of (HO$_2$CC(CH$_3$)$_2$CH$_2$O—C(O)NH—Ph)$_2$—CH$_2$

In a dry box, MDI (25.0 g) was weighed into a 500 mL RB flask equipped with a stirrer, dimethylacetamide (DMAC, 70 mL) was then added followed by hydroxypivalic acid (23.8 g). The reaction was allowed to stir overnight, then the reaction mixture was poured into water. The resulting precipitate was filtered and dried under vacuum at 100° C., affording 46.28 g (94.84%) of product. All phenyl rings in this compound are para substituted.

EXAMPLE 199

Polymerization of THF with (HO$_2$CC(CH$_3$))$_2$CH$_2$O—C(O)NH—Ph)$_2$—CH$_2$ and Ytterbium Triflate In a dry box, ytterbium triflate (10.00 g) and (HO$_2$CC(CH$_3$)$_2$CH$_2$O—C(O)NH—Ph)$_2$—CH$_2$ (1.0 g) were added to an oven dried 100 mL RB flask equipped with a stirring bar. The flask was sealed with a rubber septum and removed from the dry box. After the attachment of a nitrogen bleed THF (20.00 mL) was added via syringe. After 16 hrs. the resulting solid mass was repeatedly washed with water, then dried under vacuum affording 6.40 g of white material. NMR and GPC analysis showed the product to be contaminated with a small amount of the starting diacid.

What is claimed is:

1. A process for the polymerization of cyclic ethers, comprising, contacting, at a temperature of about −80° C. to about 130° C., one or more tetrahydrofurans, oxepanes, 1,3-dioxolanes or 1,3,5-trioxanes with a catalytic system consisting essentially of a compound of the formula MZ$_s$.Q$_t$, and an accelerator selected from the group consisting of carboxylic acids whose pKa in water is less than 6, carboxylic anhydrides and acyl halides, wherein:

M is a metal selected from the group consisting of niobium, tungsten, yttrium, the rare earth metals, zirconium, hafnium, molybdenum, tantalum, rhenium, ruthenium, osmium, rhodium, iridium, palladium, platinum, gold, cadmium, germanium, tin, lead, arsenic, antimony and bismuth;

at least one of Z is an anion of the formula R$^5$SO$_3^-$, wherein R$^5$ is perfluoroalkyl containing 1 to 12 carbon atoms or part of a fluorinated polymer wherein the carbon atoms alpha and beta to the sulfonate group are together bonded to at least four fluorine atoms, or tetraphenylborate, and the remainder of Z is oxo or one or more monovalent anions;

s is 2 when M is rhodium, iridium, palladium, platinum, or cadmium;

s is 3 when M is yttrium, a rare earth metal, arsenic, antimony, bismuth, gold, ruthenium, or osmium;

s is 4 when M is zirconium, hafnium, molybdenum, germanium, tin, or lead;

s is 5 when M is rhenium, niobium or tantalum;

s is 6 when M is tungsten;

Q is a neutral ligand;

t is 0 or an integer of 1 to 6;

and provided that each oxo group present as part of Z is considered to account for two of s.

2. The process as recited in claim 1 wherein M is a metal selected from the group consisting of niobium, tungsten, mischmetall, yttrium, a rare earth metal, zirconium, hafnium, molybdenum, tantalum, rhenium, ruthenium, osmium, rhodium, iridium, palladium, platinum, gold, cadmium, germanium, tin, lead, arsenic, antimony and bismuth.

3. The process as recited in claim 2 wherein said cyclic ether comprises the formula wherein:

each R$^1$, R$^2$, R$^3$ and R$^4$ is independently hydrogen or hydrocarbyl containing 1 to 20 carbon atoms; and n is 2 or 4.

4. The process as recited in claim 3 wherein n is 2 and R$^1$, R$^4$ and all of R$^2$ and R$^3$ are hydrogen.

5. The process as recited in claim 4 wherein M is yttrium, a rare earth metal, zirconium, hafnium, niobium, tantalum, molybdenum, tungsten, rhenium, ruthenium, palladium, gold, tin, bismuth or mischmetall.

6. The process as recited in claim 3 wherein n is 2 and R$^1$ and R$^4$ are each hydrogen, one of R$^2$ is hydrogen, the other R$^2$ is methyl, and both R$^3$ are hydrogen.

7. The process as recited in claim 2 wherein R$^5$ is trifluoromethyl or perfluoroalkyl.

8. The process as recited in claim 1 wherein said carboxylic acid is trifluoroacetic acid, formic, acetic, cyanoacetic, nitropropionic, acrylic or methacrylic acid.

9. The process as recited in claim 1 wherein said carboxylic anhydride is acetic anhydride or trifluoroacetic anhydride.

10. A process for the polymerization of cyclic ethers, comprising, contacting, at a temperature of about −80° C. to about 130° C., one or more oxiranes, oxetanes, tetrahydrofurans, oxepanes, 1,3-dioxolanes or 1,3,5-trioxanes with a zeolite which contains a metal cation selected from the group consisting of silver, niobium, tungsten, yttrium, the rare earth metals, molybdenum, tantalum, rhenium, ruthenium, osmium, rhodium, iridium, palladium, platinum, gold, cadmium, germanium, tin, lead, arsenic, antimony and bismuth; and an accelerator selected from the group consisting of carboxylic anhydrides, acyl halides and carboxylic acids whose pKa in water is less than about 6.

11. The process as recited in claim 10 wherein said cyclic ether is one or more tetrahydrofurans, oxepanes, 1,3-dioxolanes, or 1,3,5-trioxanes.

12. The process as recited in claim 11 wherein said cyclic ether comprises the formula:

wherein n is 2 or 4, and each R$^1$, R$^2$, R$^3$ and R$^4$ is independently hydrogen or hydrocarbyl containing 1 to 20 carbon atoms.

13. The process as recited in claim 12 wherein all of R$^1$, R$^2$, R$^3$ and R$^4$ are hydrogen.

14. The process as recited in claim 12 wherein n is 2; and wherein R$^1$, one of R$^2$, both of R$^3$ and R$^4$ are hydrogen and the remaining R$^2$ is alkyl containing 1–4 carbon atoms.

15. The process as recited in claim 10 wherein said metal cation is yttrium, a rare earth metal, zirconium, hafnium, mischmetall, niobium, tantalum, molybdenum, tungsten, rhenium, ruthenium, palladium, gold, tin or bismuth.

16. The process as recited in claim 15 wherein said metal cation is yttrium, ytterbium, dysprosium, erbium, neodymium, lanthanum, mischmetall, or zirconium.

17. The process as recited in claim 10 wherein said accelerator is a carboxylic acid whose pKa in water is about 6 or less.

18. The process as recited in claim 17 wherein said carboxylic acid is selected from the group consisting of formic, acetic, trifluoroacetic, acrylic, methacrylic, cyanoacetic, nitropropionic, and nitrobenzoic.

19. A process for the polymerization of cyclic ethers, comprising, contacting, at a temperature of about −80° C. to about 130° C., one or more oxiranes, oxetanes, tetrahydrofurans, oxepanes, 1,3-dioxolanes, or 1,3,5-trioxanes; with a catalytic system consisting essentially of a heterogeneous catalyst containing a metal perfluoroalkylsulfonate attached to the surface of said catalyst though said metal, and an accelerator; said metal selected from the group consisting of niobium, tungsten, yttrium, the rare earth metals, zirconium, hafnium, molybdenum, tantalum, rhenium, ruthenium, osmium, rhodium, iridium, palladium, platinum, gold, cadmium, germanium, tin, lead, arsenic, antimony and bismuth; said accelerator selected from the group consisting of carboxylic anhydrides, acyl halides, and carboxylic acids whose pKa in water is less than about 6.

20. The process as recited in claim 19 wherein said cyclic ether is one or more of tetrahydrofurans, oxepanes, 1,3-dioxolanes, or 1,3,5-trioxanes.

21. The process as recited in claim 20 wherein said cyclic ether comprises the formula:

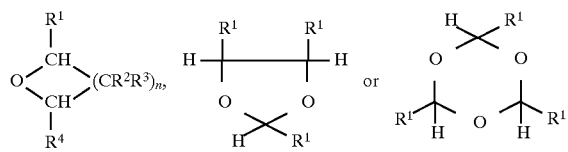

wherein n is 2 or 4, and each $R^1$, $R^2$, $R^3$ and $R^4$ is independently hydrogen or hydrocarbyl containing 1 to 20 carbon atoms.

22. The process as recited in claim 21 wherein all of $R^1$, $R^2$, $R^3$ and $R^4$ are hydrogen.

23. The process as recited in claim 21 wherein n is 2; and wherein $R^1$, one of $R^2$, both of $R^3$ and $R^4$ are hydrogen and the remaining $R^2$ is alkyl containing 1–4 carbon atoms.

24. The process as recited in claim 19 wherein said metal cation is yttrium, a rare earth metal, zirconium, hafnium, mischmetall, niobium, tantalum, molybdenum, tungsten, rhenium, ruthenium, palladium, gold, tin or bismuth.

25. The process as recited in claim 24 wherein said metal cation is yttrium, ytterbium, dysprosium, erbium, neodymium, lanthanum, mischmetall, or zirconium.

26. The process as recited in claim 19 wherein said accelerator is a carboxylic acid whose pKa in water is about 6 or less.

27. The process as recited in claim 19 wherein said heterogeneous catalyst support is alumina, silica, silica-aluminate, carbon or zirconia.

28. A process for the production of poly(ether-esters), comprising, contacting, at a temperature of about −80° C. to about 130° C., a tetrahydrofuran with a polycarboxylic acid of the formula $A(CO_2H)_x$ and a catalyst of the formula $MZ_s \cdot Qt$, wherein:

M is a metal selected from the group consisting of tungsten, niobium, yttrium, a rare earth metal zirconium, hafnium, molybdenum, tantalum, rhenium, ruthenium, osmium, rhodium, iridium, palladium, platinum, silver, gold, cadmium, germanium, tin, lead, arsenic, antimony and bismuth;

Z is an anion of the formula $R^5SO_3^-$, wherein $R^5$ is perfluoroalkyl containing 1 to 12 carbon atoms or part of a fluorinated group wherein the carbon atoms alpha and beta to the sulfonate group are together bonded to at least four fluorine atoms;

s is 1 when M is silver;

s is 2 when M is rhodium, iridium, palladium, platinum, or cadmium;

s is 3 when M is yttrium, a rare earth metal, arsenic, antimony, bismuth, gold, ruthenium, or osmium;

s is 4 when M is zirconium, hafnium, molybdenum, germanium, tin, or lead;

s is 5 when M is rhenium, niobium or tantalum;

s is 6 when M is tungsten;

Q is a neutral ligand;

t is 0 or an integer of 1 to 6; and each A is independently an organic radical having x free valencies;

each x is independently 2, 3, 4, 5 or 6; and provided that:
A is bound to carboxyl groups through a carbon atom;
said polycarboxylic acid has a pKa of about 6 or less;
said polycarboxylic acid does not by itself catalyze polymerization of the tetrahydrofuran; and
the ratio of equivalents of carboxyl groups of said polycarboxylic acid to moles of said catalyst is less than 6.

29. The process of claim 28 wherein x is 2.

30. The process as recited in claim 28 wherein M is a metal selected from the group consisting of yttrium, a rare earth metal zirconium, hafnium, molybdenum, tantalum, rhenium, ruthenium, osmium, rhodium, iridium, palladium, platinum, silver, gold, cadmium, germanium, tin, lead, arsenic, antimony and bismuth.

31. The process as recited in claim 28 wherein the tetrahydrofuran is of Formula I, wherein $R^1$, $R^4$, and all of $R^2$ and $R^3$ are hydrogen

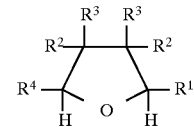

32. The process as recited in claim 28 wherein the tetrahydrofuran is of Formula I, wherein $R^1$ and $R^4$ are hydrogen, one of $R^2$ is hydrogen, the other $R^2$ is methyl, and both of care hydrogen

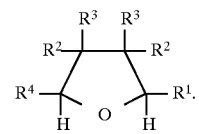

33. The process as recited in claim 28 wherein $R^5$ is trifluoromethyl.

34. The process as recited in claim 28 wherein A is tetramethylene, p-phenylene, or m-phenylene.

35. The process as recited in claim 28 wherein A contains one or more of imide, ester, amide, urethane or urea.

36. The process as recited in claim 28 wherein the tetrahydrofuran is of Formula I wherein all of $R^1$, $R^2$, $R^3$ and $R^4$ are independently hydrogen or a $C_1$ to $C_{20}$ hydrocarbyl

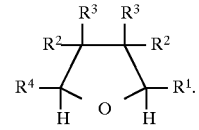

* * * * *